US012643947B2

(12) United States Patent
Kipps et al.

(10) Patent No.: US 12,643,947 B2
(45) Date of Patent: Jun. 2, 2026

(54) ANTI-ROR-2 ANTIBODIES AND METHODS OF USE

(71) Applicant: The Regents of the University of California, Oakland, CA (US)

(72) Inventors: Thomas J. Kipps, San Diego, CA (US); George F. Widhopf, II, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 855 days.

(21) Appl. No.: 17/777,591

(22) PCT Filed: Nov. 18, 2020

(86) PCT No.: PCT/US2020/061130
§ 371 (c)(1),
(2) Date: May 17, 2022

(87) PCT Pub. No.: WO2021/102055
PCT Pub. Date: May 27, 2021

(65) Prior Publication Data
US 2023/0192846 A1     Jun. 22, 2023

Related U.S. Application Data

(60) Provisional application No. 62/936,900, filed on Nov. 18, 2019.

(51) Int. Cl.
| | |
|---|---|
| *C07K 16/28* | (2006.01) |
| *A61K 38/00* | (2006.01) |
| *A61K 40/11* | (2025.01) |
| *A61K 40/15* | (2025.01) |
| *A61K 40/31* | (2025.01) |
| *A61K 40/42* | (2025.01) |
| *A61K 47/68* | (2017.01) |
| *A61P 35/00* | (2006.01) |
| *C07K 14/705* | (2006.01) |
| *C07K 14/725* | (2006.01) |
| *G01N 33/574* | (2006.01) |

(52) U.S. Cl.
CPC .......... *C07K 16/2803* (2013.01); *A61K 40/11* (2025.01); *A61K 40/15* (2025.01); *A61K 40/31* (2025.01); *A61K 40/421* (2025.01); *A61K 47/6849* (2017.08); *A61P 35/00* (2018.01); *C07K 14/7051* (2013.01); *G01N 33/57492* (2013.01); *A61K 38/00* (2013.01); *A61K 2239/50* (2023.05); *C07K 2317/24* (2013.01); *C07K 2317/34* (2013.01); *C07K 2317/524* (2013.01); *C07K 2317/526* (2013.01); *C07K 2317/565* (2013.01); *C07K 2317/622* (2013.01); *C07K 2317/77* (2013.01); *C07K 2317/92* (2013.01); *C07K 2319/02* (2013.01); *C07K 2319/03* (2013.01)

(58) Field of Classification Search
CPC ............ C07K 16/2803; C07K 14/7051; C07K 2317/24; C07K 2317/34; C07K 2317/524; C07K 2317/526; C07K 2317/565; C07K 2317/622; C07K 2317/77; C07K 2317/92; C07K 2319/02; C07K 2319/03; C07K 2317/33; A61K 40/11; A61K 40/15; A61K 40/31; A61K 40/421; A61K 47/6849; A61K 38/00; A61K 2239/50; A61K 2039/505; A61P 35/00; G01N 33/57492; G01N 33/57484
See application file for complete search history.

(56) References Cited

U.S. PATENT DOCUMENTS

2019/0031754 A1     1/2019   Rader et al.

FOREIGN PATENT DOCUMENTS

| | | |
|---|---|---|
| WO | WO-2008/031009 A2 | 3/2008 |
| WO | WO-2008/031009 A3 | 3/2008 |
| WO | WO-2016/166297 A1 | 10/2016 |
| WO | WO-2017/197234 A1 | 11/2017 |
| WO | WO-2017/218707 A2 | 12/2017 |
| WO | WO-2017/218707 A3 | 12/2017 |
| WO | WO-2019/016392 A1 | 1/2019 |

OTHER PUBLICATIONS

International Search Report mailed on Apr. 7, 2021 for PCT Application No. PCT/US2020/061130, filed Nov. 18, 2020, 7 pages.
Written Opinion mailed on Apr. 7, 2021 for PCT Application No. PCT/US2020/061130, filed Nov. 18, 2020, 9 pages.
Partial European Search Report mailed on Nov. 29, 2023, for EP Patent Application No. 20889747.0, 14 pages.

*Primary Examiner* — Misook Yu
*Assistant Examiner* — James Lyle McLellan
(74) *Attorney, Agent, or Firm* — MINTZ, LEVIN, COHN, FERRIS, GLOVSKY AND POPEO, P.C.

(57) ABSTRACT

Provided herein are, inter alia, antibodies (e.g., humanized antibodies, monoclonal antibodies), antibody fragments (e.g., scFvs) and antibody compositions (e.g., chimeric antigen receptors, bispecific antibodies), which bind human tyrosine kinase-like orphan receptor 2 (ROR2) with high efficiency and specificity. The antibodies and antibody compositions provided herein include novel light and heavy chain domain CDRs and framework regions and are, inter alia, useful for diagnosing and treating cancer and other ROR2-related diseases.

13 Claims, 20 Drawing Sheets
Specification includes a Sequence Listing.

FIG. 1

```
                        _____Leader_____
              10        20        30        40        50        60
hROR2   MARGSALPRRPLLCIPAVWAAAALLLSVSRTSGEVEVLDPNDPLGPLDGQDGPIPTLKGY
mROR2   ....WVL.S.VP..AR...T......WTPW.A....DSEAI.T..QP..P.S.L......

_____Ig-Like Domain_____
              70        80        90        100       110       120
hROR2   FLNFLEPVNNITIVQGQTAILHCKVAGNPPPNVRWLKNDAPVVQEPRRITIRKTEYGSRL
mROR2   ..............................................VV...........

130       140       150       160       170       180
hROR2   RIQDLDTTDTGYYQCVATNGMKTITATGVLFVRLGPTHSPNHNFQDDYHEDGFCQPYRGI
mROR2   ......................L...........Y...............DQ.........

_____CRD_____
              190       200       210       220       230       240
hROR2   ACARFIGNRTIYVDSLQMQGEIENRITAAPTMIGTSTHLSDQCSQFAIPSFCHFVFPLCD
mROR2   ..............................................Q..............

250       260       270       280       290       300
hROR2   ARSRTPKPRELCRDECEVLESDLCRQEYTIARSNPLILMRLQLPKCEALPHPESPDAANC
mROR2   .C..A................N......................................

_____Kringle_____
              310       320       330       340       350       360
hROR2   MRIGIPAERLGRYHQCYNGSGMDYRGTASTTKSGHQCQPWALQHPHSHHLSSTDFPELGG
mROR2   ....................A....M..................R....E......

370       380       390       400
hROR2   GHAYCRNPGGQMEGPWCFTQNKNVRMELCDVPSCSPRDSSKMG
mROR2   ..........................V.......P....YG....
```

FIG. 4A
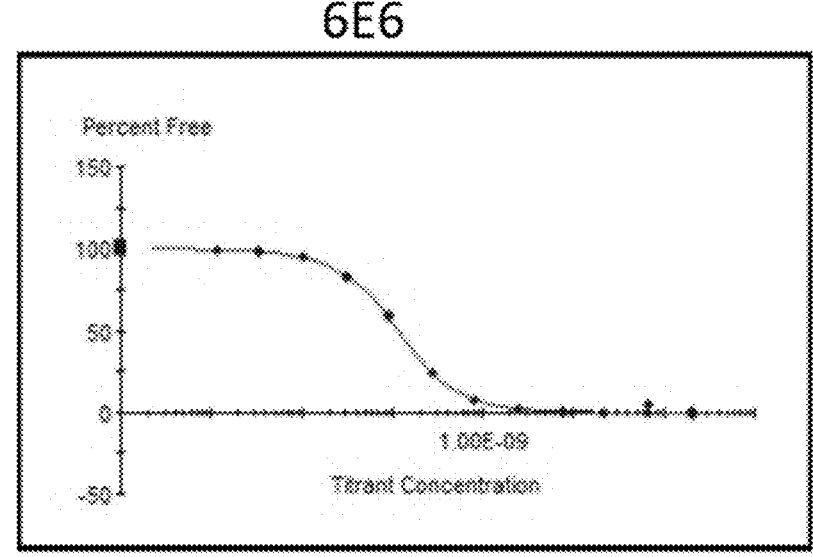
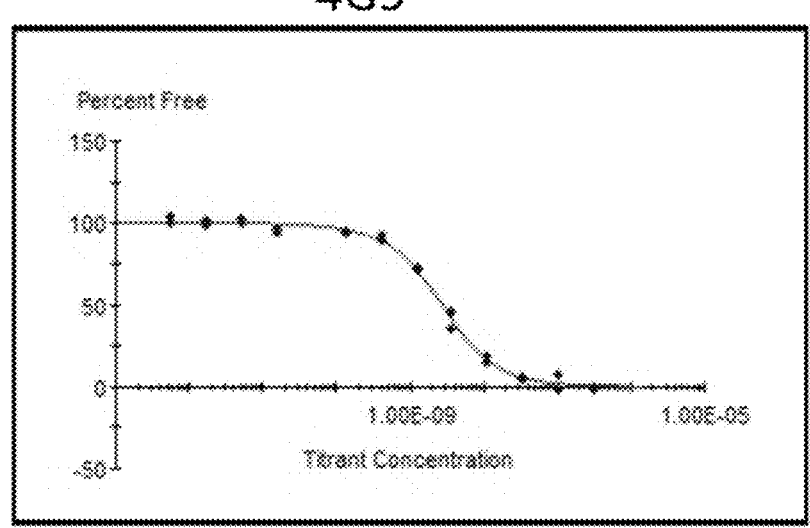

FIG. 4B
6E6
Kd:                    55.59pM
95% confidence interval
Kd High:               69.01pM
Kd Low:                44.53pM
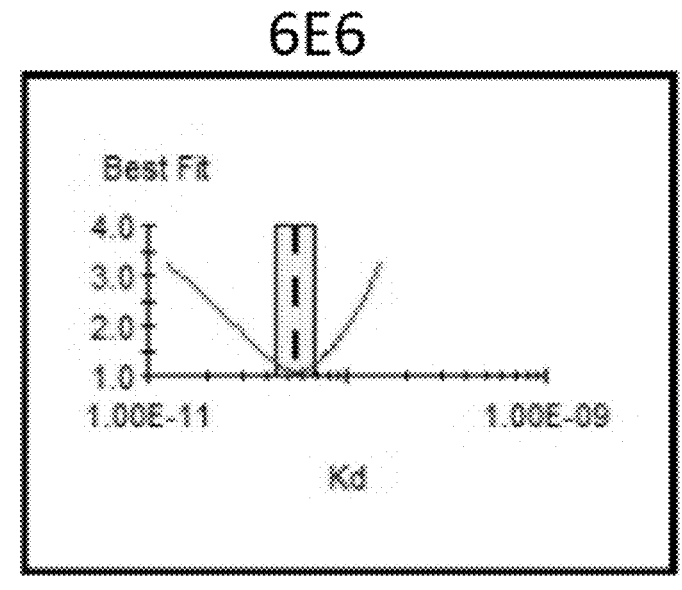
4G9
Kd:                    1.90nM
95% confidence interval
Kd High:               3.24nM
Kd Low:                1.02nM
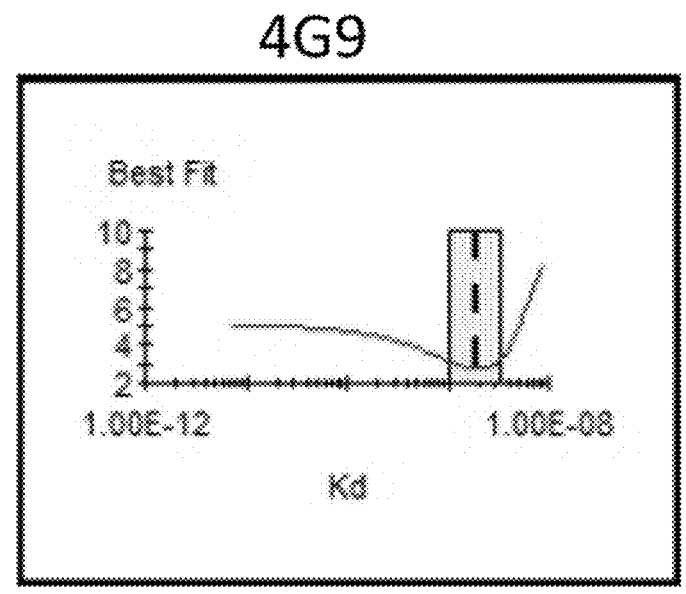

Negative Control Supernatant

■ = human ROR2    ▨ = mouse ROR2

Kd:                        73.71pM
95% confidence interval
Kd High:                   102.03pM
Kd Low:                    58.45pM

ANTI-ROR-2 ANTIBODIES AND METHODS OF USE

CROSS-REFERENCE TO RELATED APPLICATIONS

This application is a U.S. National Phase Application of PCT Application No. PCT/US2020/061130, filed Nov. 18, 2020, which is an International Application of and claims the benefit of priority under 35 U.S.C. § 119(e) to U.S. Provisional Application No. 62/936,900, filed Nov. 18, 2019, each of which is hereby incorporated by reference in its entirety and for all purposes.

STATEMENT AS TO RIGHTS TO INVENTIONS MADE UNDER FEDERALLY SPONSORED RESEARCH AND DEVELOPMENT

This invention was made with government support under CA236361 and CA81534 awarded by the National Institutes of Health. The government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 048537-632N01US_SL_ST25.txt, created on Dec. 24, 2025, 127,649 bytes, machine format IBM-PC, MS Windows operating system, is hereby incorporated by reference.

BACKGROUND

Receptor tyrosine kinase-like orphan receptor 2 (ROR2) is a developmentally restricted receptor for Wnt5a. Human ROR2 is a 943 amino acid single-pass type I membrane protein with a calculated molecular weight of 104.8 kDa. It is highly conserved across several species with a 92% amino acid identity between the mouse and human proteins. ROR2 can repress transcription of Wnt target genes and modulate Wnt signaling by sequestering canonical Wnt ligands, thereby serving as a tumor suppressor in different cell contexts. Recently, ROR2 has been implicated in progression of numerous cancers including breast, ovarian, pancreatic, cervical, gastric, renal, head and neck, bone, skin and prostate. Therefore, there is a need for antibodies, antibody fragments, bispecific antibodies and chimeric antigen receptors that specifically target human ROR2, inhibit its function and thereby serve as effective therapeutics and diagnostics. The compositions and methods provided herein address these and other needs in the art.

BRIEF SUMMARY OF THE INVENTION

In an aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:25, a CDR H2 as set forth in SEQ ID NO:26 and a CDR H3 as set forth in SEQ ID NO:27; and wherein the light chain variable domain includes: a CDR L1 as set forth in SEQ ID NO:28, a CDR L2 as set forth in SEQ ID NO:29, and a CDR L3 as set forth in SEQ ID NO:30.

In an aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:31, a CDR H2 as set forth in SEQ ID NO:32 and a CDR H3 as set forth in SEQ ID NO:33; and wherein the light chain variable domain includes: a CDR L1 as set forth in SEQ ID NO:34, a CDR L2 as set forth in SEQ ID NO:35, and a CDR L3 as set forth in SEQ ID NO:36.

In another aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:37, a CDR H2 as set forth in SEQ ID NO:38 and a CDR H3 as set forth in SEQ ID NO:39; and wherein the light chain variable domain includes: a CDR L1 as set forth in SEQ ID NO:40, a CDR L2 as set forth in SEQ ID NO:41, and a CDR L3 as set forth in SEQ ID NO:42.

In another aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:43, a CDR H2 as set forth in SEQ ID NO:44 and a CDR H3 as set forth in SEQ ID NO:45; and wherein the light chain variable domain includes: a CDR L1 as set forth in SEQ ID NO:46, a CDR L2 as set forth in SEQ ID NO:47, and a CDR L3 as set forth in SEQ ID NO:48.

In an aspect is provided a method of treating cancer in a subject in need thereof, the method including administering to a subject a therapeutically effective amount of an antibody provided herein including embodiments thereof.

In an aspect is provided a method of inhibiting metastasis of a ROR2 expressing cancer in a subject in need thereof, the method including administering to a subject a therapeutically effective amount of an antibody provided herein, including embodiments thereof.

In another aspect is provided a method of detecting a ROR2 expressing cell, the method including (i) contacting a ROR2-expressing cell with an antibody provided herein including embodiments thereof; and (ii) detecting binding of the antibody to a ROR2 protein expressed by the cell.

In another aspect is provided a method of delivering a therapeutic agent to a ROR2 expressing cell, the method including contacting a ROR2 expressing cell with an antibody provided herein including embodiments thereof, wherein the antibody is attached to a therapeutic agent.

In another aspect is provided a method of inhibiting migration of a ROR2-expressing cell, the method including contacting a ROR2 expressing cell with an antibody provided herein including embodiments thereof.

In an aspect is provided a anti-ROR2 antibody, wherein the anti-ROR2 antibody binds the same epitope as an anti-ROR2 antibody including a heavy chain variable domain including: a CDR H1 as set forth in SEQ ID NO:25, a CDR H2 as set forth in SEQ ID NO:26 and a CDR H3 as set forth in SEQ ID NO:27; and a light chain variable domain including: a CDR L1 as set forth in SEQ ID NO:28, a CDR L2 as set forth in SEQ ID NO:29, and a CDR L3 as set forth in SEQ ID NO:30.

In an aspect is provided a anti-ROR2 antibody, wherein the anti-ROR2 antibody binds the same epitope as an anti-ROR2 antibody including a heavy chain variable domain of SEQ ID:2; and a light chain variable domain of SEQ ID NO:4.

In an aspect is provided an anti-ROR2 antibody, wherein the anti-ROR2 antibody binds the same epitope as an anti-ROR2 antibody including a heavy chain variable domain encoded by the nucleic acid sequence of SEQ ID:1; and a light chain variable domain encoded by the nucleic acid sequence of SEQ ID:3.

In an aspect is provided an anti-ROR2 antibody, wherein the anti-ROR2 antibody binds the same epitope as an anti-ROR2 antibody including a heavy chain variable domain including: a CDR H1 as set forth in SEQ ID NO:31, a CDR H2 as set forth in SEQ ID NO:32 and a CDR H3 as set forth in SEQ ID NO:33; and a light chain variable domain including: a CDR L1 as set forth in SEQ ID NO:34, a CDR L2 as set forth in SEQ ID NO:35, and a CDR L3 as set forth in SEQ ID NO:36.

In an aspect is provided an anti-ROR2 antibody, wherein the anti-ROR2 antibody binds the same epitope as an anti-ROR2 antibody including a heavy chain variable domain of SEQ ID:6; and a light chain variable domain of SEQ ID NO:8.

In an aspect is provided an anti-ROR2 antibody, wherein the anti-ROR2 antibody binds the same epitope as an anti-ROR2 antibody including a heavy chain variable domain encoded by the nucleic acid sequence of SEQ ID:5; and a light chain variable domain encoded by the nucleic acid sequence of SEQ ID:7.

In an aspect is provided an anti-ROR2 antibody, wherein the anti-ROR2 antibody binds the same epitope as an anti-ROR2 antibody including a heavy chain variable domain including: a CDR H1 as set forth in SEQ ID NO:37, a CDR H2 as set forth in SEQ ID NO:38 and a CDR H3 as set forth in SEQ ID NO:39; and a light chain variable domain including: a CDR L1 as set forth in SEQ ID NO:40, a CDR L2 as set forth in SEQ ID NO:41, and a CDR L3 as set forth in SEQ ID NO:42.

In an aspect is provided an anti-ROR2 antibody, wherein the anti-ROR2 antibody binds the same epitope as an anti-ROR2 antibody including a heavy chain variable domain of SEQ ID:10; and a light chain variable domain of SEQ ID NO:12.

In an aspect is provided an anti-ROR2 antibody, wherein the anti-ROR2 antibody binds the same epitope as an anti-ROR2 antibody including a heavy chain variable domain encoded by the nucleic acid sequence of SEQ ID:9; and a light chain variable domain encoded by the nucleic acid sequence of SEQ ID:11.

In an aspect is provided an anti-ROR2 antibody, wherein said anti-ROR2 antibody binds the same epitope as an anti-ROR2 antibody including a heavy chain variable domain including: a CDR H1 as set forth in SEQ ID NO:43, a CDR H2 as set forth in SEQ ID NO:44 and a CDR H3 as set forth in SEQ ID NO:45; and a light chain variable domain including: a CDR L1 as set forth in SEQ ID NO:46, a CDR L2 as set forth in SEQ ID NO:47, and a CDR L3 as set forth in SEQ ID NO:48.

In an aspect is provided an anti-ROR2 antibody, wherein the anti-ROR2 antibody binds the same epitope as an anti-ROR2 antibody including a heavy chain variable domain of SEQ ID:14; and a light chain variable domain of SEQ ID NO:16.

In an aspect is provided an anti-ROR2 antibody, wherein the anti-ROR2 antibody binds the same epitope as an anti-ROR2 antibody including a heavy chain variable domain encoded by the nucleic acid sequence of SEQ ID:13; and a light chain variable domain encoded by the nucleic acid sequence of SEQ ID:15.

In another aspect is provided a chimeric antigen receptor including: (i) an antibody region including: (a) a light chain variable domain including a CDR L1 as set forth in SEQ ID NO: 28, a CDR L2 as set forth in SEQ ID NO:29 and a CDR L3 as set forth in SEQ ID NO:30; and (b) a heavy chain variable region domain including a CDR H1 as set forth in SEQ ID NO:25, a CDR H2 as set forth in SEQ ID NO:26, and a CDR H3 as set forth in SEQ ID NO:27; and (ii) a transmembrane domain.

In an aspect is provided a chimeric antigen receptor including: (i) an antibody region including: (a) a light chain variable domain including a CDR L1 as set forth in SEQ ID NO:34, a CDR L2 as set forth in SEQ ID NO:35 and a CDR L3 as set forth in SEQ ID NO:36; and (b) a heavy chain variable region domain including a CDR H1 as set forth in SEQ ID NO:31, a CDR H2 as set forth in SEQ ID NO:32, and a CDR H3 as set forth in SEQ ID NO:33; and (ii) a transmembrane domain.

In an aspect is provided a chimeric antigen receptor including: (i) an antibody region including: (a) a light chain variable domain including a CDR L1 as set forth in SEQ ID NO:40, a CDR L2 as set forth in SEQ ID NO:41 and a CDR L3 as set forth in SEQ ID NO:42; and (b) a heavy chain variable region domain including a CDR H1 as set forth in SEQ ID NO:37, a CDR H2 as set forth in SEQ ID NO:38, and a CDR H3 as set forth in SEQ ID NO:39; and (ii) a transmembrane domain.

In an aspect is provided a chimeric antigen receptor including: (i) an antibody region including: (a) a light chain variable domain including a CDR L1 as set forth in SEQ ID NO:46, a CDR L2 as set forth in SEQ ID NO:47 and a CDR L3 as set forth in SEQ ID NO:48; and (b) a heavy chain variable region domain including a CDR H1 as set forth in SEQ ID NO:43, a CDR H2 as set forth in SEQ ID NO:44, and a CDR H3 as set forth in SEQ ID NO:45; and (ii) a transmembrane domain.

In another aspect is provided a method of treating cancer in a subject in need thereof the method including, administering a therapeutically effective amount of a chimeric antigen receptor provided herein including embodiments thereof to a subject.

In another aspect is provided an anti-receptor tyrosine kinase-like orphan receptor 2 (ROR2) antibody, capable of binding an extracellular domain of ROR2 including an amino acid sequence of SEQ ID NO:22.

BRIEF DESCRIPTION OF THE DRAWINGS

FIG. 1. Comparison of the extracellular regions of human and mouse ROR2. Alignment of the amino acid sequences of the extracellular region of human (upper sequence; SEQ ID NO:18) and mouse (lower sequence: SEQ ID NO:20) ROR2 are shown. Dots indicate homology at that position, whereas differences are designated by the single letter amino acid codons. The Ig-like, CRD and kringle domains are labeled and indicated by lines above the sequence.

Figure 2A:
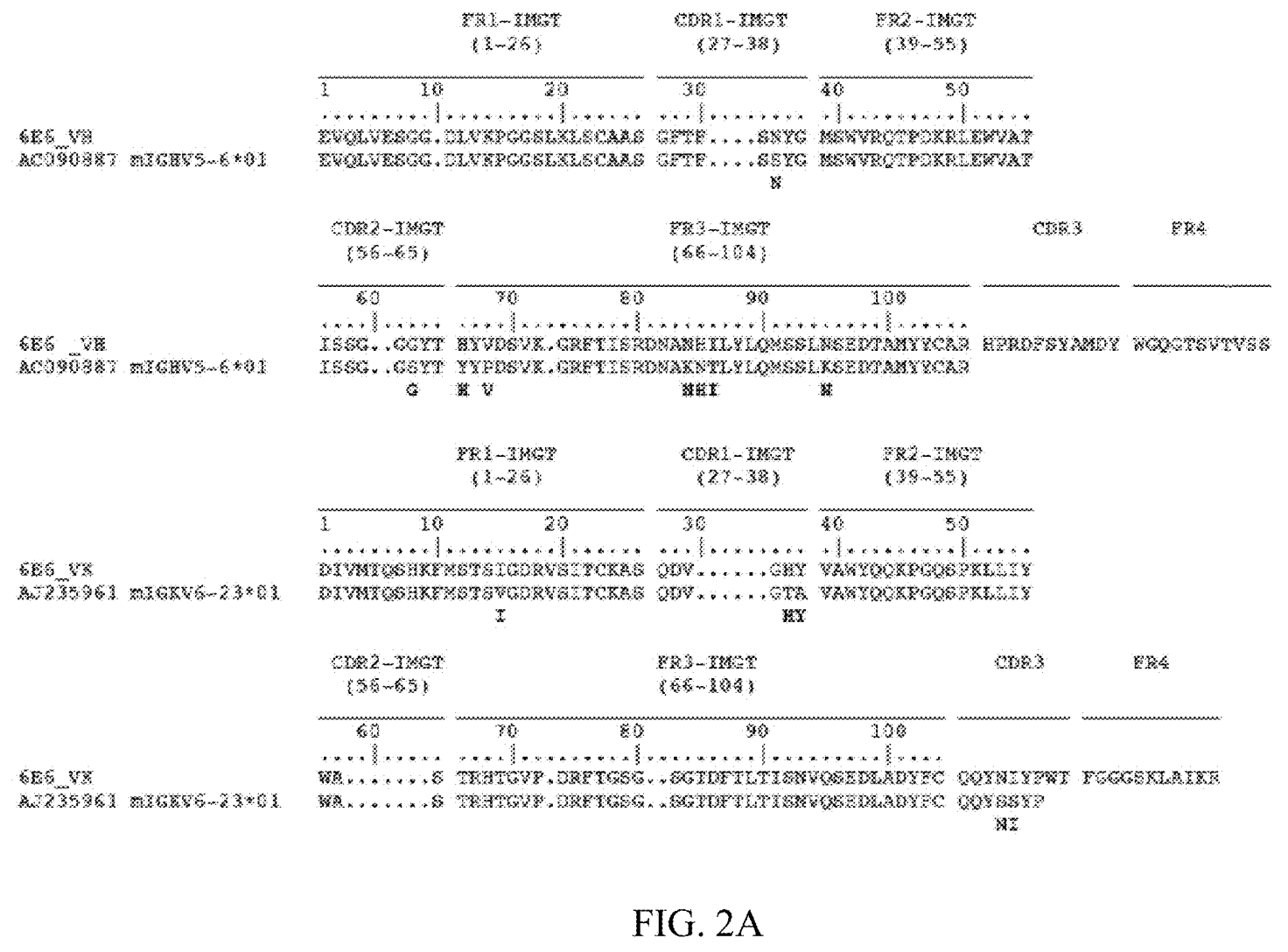
Figure 2B:
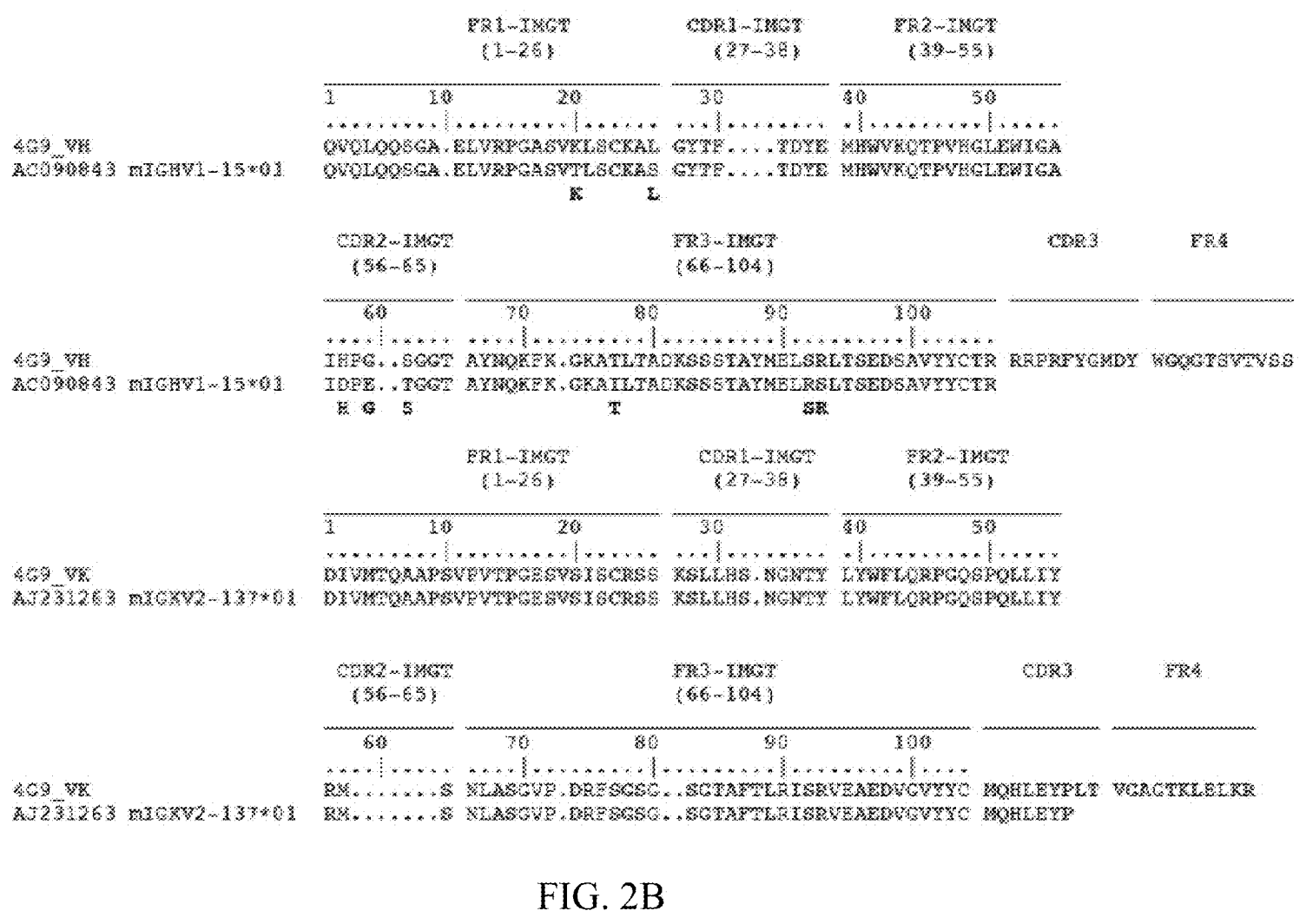
Figure 2C:
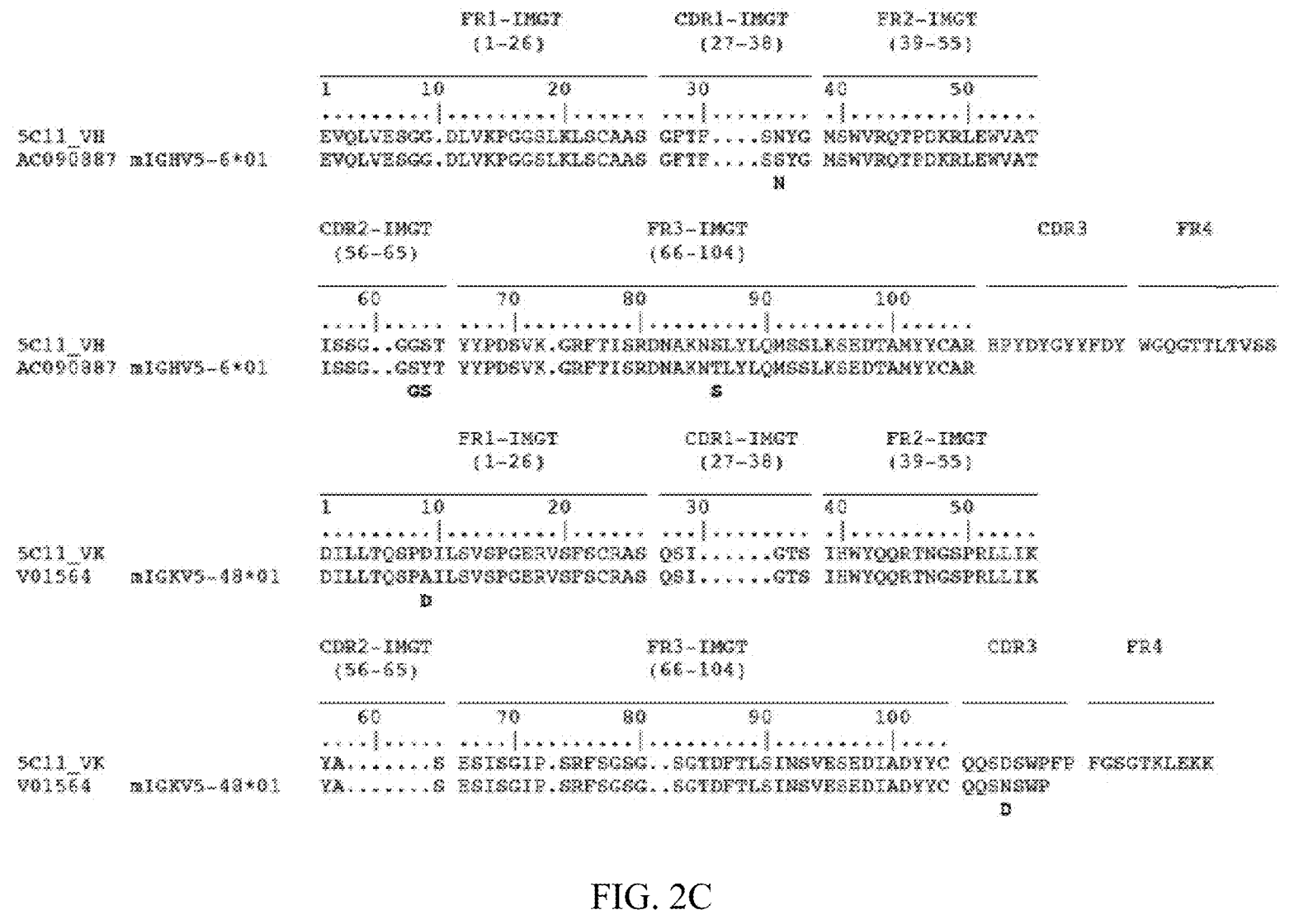
Figure 2D:
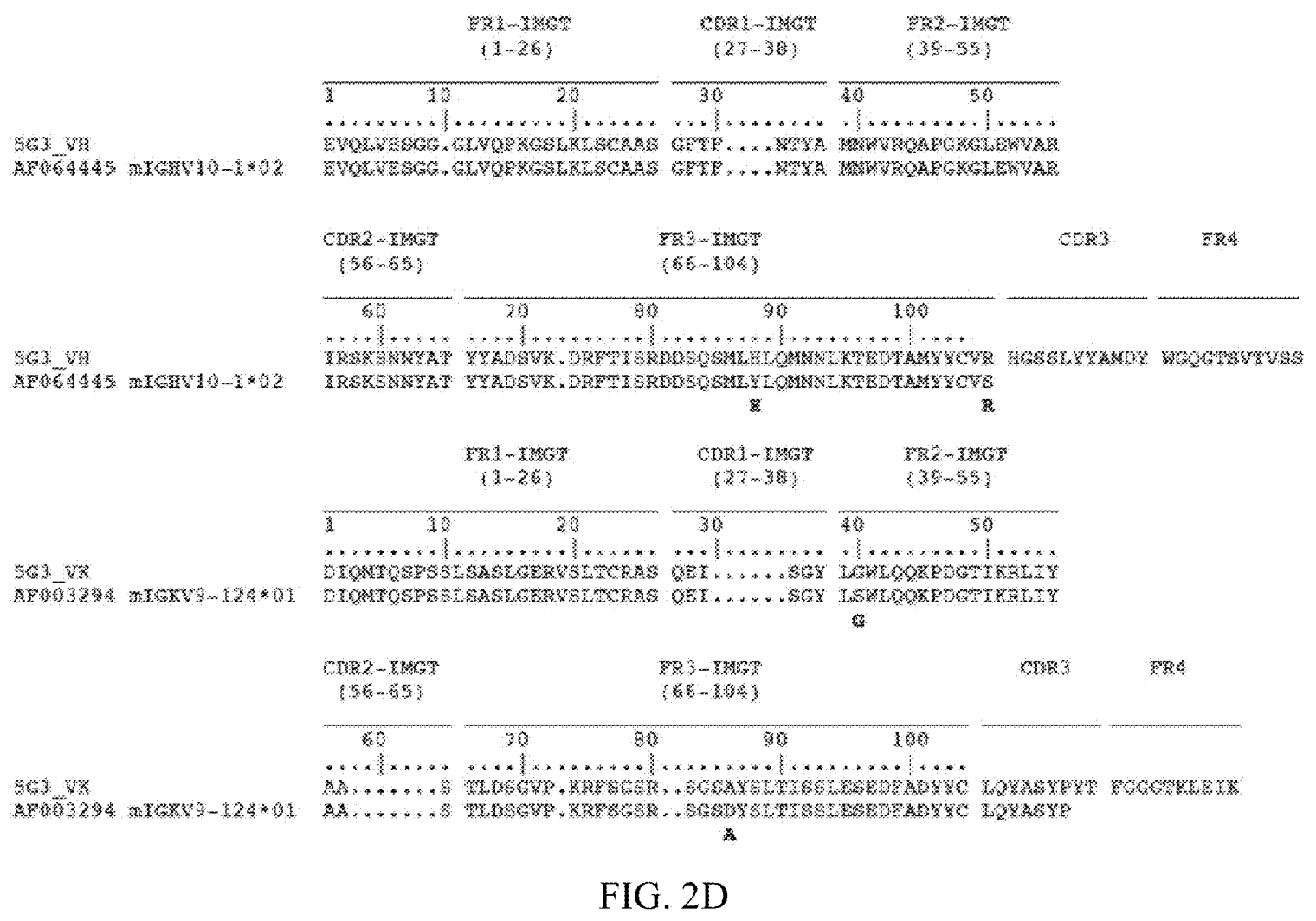

FIGS. 2A-2D. Amino acid sequence and alignment to the closest mouse IGHV (upper sequence) or IGKV (lower sequence) germline gene depicted for each of the four mouse anti-human ROR2 hybridomas, designated (FIG. 2A) 6E6, (FIG. 2B) 4G9, (FIG. 2C) 5C11 and (FIG. 2D) 5G3. For each alignment the upper sequence depicts the amino acid sequence of the heavy or light chain variable region beginning at the first codon of the first framework region and ending with the last codon of the fourth framework region. The lower sequence depicts the amino acid sequence of the heavy or light chain variable region of the most homologous mouse IGHV or IGKV germline gene. The framework (FR) and complementarity determining (CDR) regions are marked above the sequences, and the differences between the two sequences are noted below the aligned sequences, and are designated as single letter amino acid codons in bold font. The first and second sequence alignments in FIG. 2A include the amino acid sequences of 6E6 VH (upper sequence, SEQ ID NO:2) and AC090887 mIGHV5-6*0) 1 (lower sequence, SEQ ID NO:115). The third and fourth sequence alignments in FIG. 2A include the amino acid sequences of 6E6 VK (upper sequence, SEQ ID NO:4) and AJ235961 mIGKV6-23*0) 1 (lower sequence, SEQ ID NO:116). The first and second sequence alignments in FIG. 2B include the amino acid sequences of 4G9 VH (upper sequence, SEQ ID NO:6) and AC090843 mIGHV1-15*0) 1 (lower sequence, SEQ ID NO:117). The third and fourth sequence alignments in FIG. 2B include the amino acid sequences of 4G9 VK (upper sequence, SEQ ID NO:8) and AJ231263 mIGKV2-137*0) 1 (lower sequence, SEQ ID NO:118). The first and second sequence alignments in FIG. 2C include the amino acid sequences of 5C11 VH (upper sequence. SEQ ID NO:10) and AC090887 mIGHV5-6*01 (lower sequence, SEQ ID NO:115). The third and fourth sequence alignments in FIG. 2C include the amino acid sequences of 5C11 VK (upper sequence, SEQ ID NO:12) and V01564 mIGKV5-48*01 (lower sequence. SEQ ID NO:119). The first and second sequence alignments in FIG. 2D include the amino acid sequences of 5G3 VH (upper sequence. SEQ ID NO:14) and AF064445 mIGHV10-1*02 (lower sequence. SEQ ID NO:120). The third and fourth sequence alignments in FIG. 2D include the amino acid sequences of 5G3 VK (upper sequence. SEQ ID NO:16) and AF003294 mIGKV9-124*01 (lower sequence. SEQ ID NO:121).

FIGS. 4A and 4B. Affinity measurement of binding of the 6E6 and 4G9 mAb to recombinant ROR2 protein. (FIG. 4A) Analysis was performed using a KinExA 3200) instrument. The proportion of anti-human ROR2 mAb bound to particles coated with ROR2 protein (y-axis) in the presence of increasing molar (M) concentration of soluble ROR2 competitor (x-axis) is shown for 6E6 (upper panel) and 4G9 (lower panel). (FIG. 4B) Illustration of the 95% confidence interval for the measured Kd of 6E6 (upper panel) and 4G9 (lower panel) for binding to human ROR2.

(FIG. 7A) Binding of the 6E6 and 4G9 mAb to human ROR was assessed by flow cytometric staining and analysis of several cell lines known to express ROR2. Cells were stained on ice for 20 minutes with 10 μg/ml of 6E6 or 4G9 anti-human ROR2-Alexa647 conjugated mAb (shaded histograms) or equal amounts of isotype matched control mAb (open histograms), washed and analyzed. Histograms depict the relative fluorescence intensity (x axis) of viable cells as determined by light scatter characteristics. (FIG. 7B) Specificity was validated by the absence of binding to HCT116 colorectal cancer cells and HEK293 cells in which ROR2 expression was eliminated using CRISPR-cas9, compared to parental cell lines.

(FIG. 10A) Histograms depict the relative fluorescence intensity (x axis) of viable cells as determined by light scatter characteristics. Shaded histograms depict stained cells incubated at 37° C. for 120 min. dashed histograms depict stained cells incubated at 4° C. for 120 min, and open histograms depict unstained cells incubated at 37° C. for 120 min. Increased relative fluorescence is noted for both 6E6 (upper panel) and 4G9 (lower panel) pHrodo-conjugated mAb for K562 cells that express ROR2, but not ROR2 negative JEKO cells, as compared to stained cells incubated at 4° C. for 120 min or unstained cells incubated at 37° C. for 120 min. (FIG. 10B) Graphic representation of the increase of the mean fluorescence (y-axis) of 6E6 or 4G9 pHrodo conjugated mAb on K562 cells over time (x-axis). AMFI is the mean fluorescence intensity of K562 cells stained with either pHrodo conjugated mAb incubated at 37° C. *minus* the mean fluorescence intensity of an aliquot of the same stained cells incubated at 4° C. for the equivalent amount of time.

(FIG. 11A) Histograms display the average number of invading cells in each of three chambers of MCF7 cells or MCF7-ROR2 cells treated with mouse IgG (gray bars). 6E6 mAb (white bars) or 4G9 (black bars), normalized to MCF7 treated with control mIgG. Data are shown as mean+/−SD (n=3). (FIG. 11B) Representative photomicrographs of invasive cells from MCF7 cells (upper panels) or MCF7-ROR2 cells (lower panels) treated with either 25 μg/ml of control antibody (left panels) 6E6 anti-ROR2 mAb (center panels) or 4G9 anti-human ROR2 mAb.

(FIG. 12A) The proportion of the 6E6 anti-human ROR2 scFv bound to particles coated with recombinant ROR2 protein (y-axis) in the presence of increasing molar (M) concentration of soluble ROR2 competitor (x-axis) is shown. (FIG. 12B) Illustration of the 95% confidence interval for the measured Kd of 6E6 scFv for binding to recombinant human ROR2.

DETAILED DESCRIPTION

Figure 3:
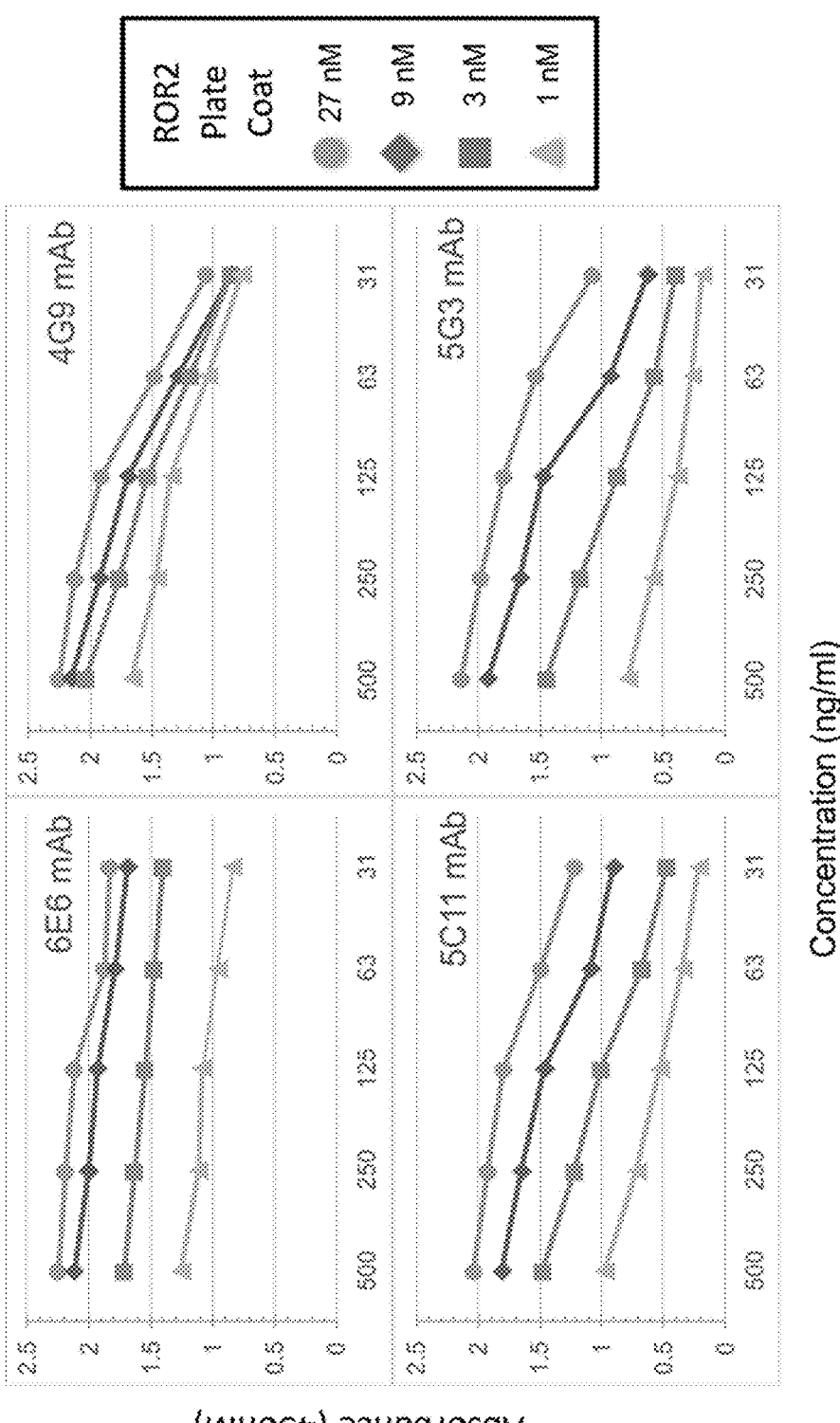
FIG. 3. Assessment of binding of anti-ROR2 mAb to recombinant human ROR2 at varying amounts of immobilized protein and concentrations of soluble mAb. Wells were coated overnight with recombinant human ROR2-extracellular domain (ROR2-ECD), at 27, 9, 3 and 1 nM, washed and blocked with sample buffer (1×BBS+1% BSA) at 37° C. for 90 minutes. Serial dilutions ranging from 500-31 ng/ml of 6E6, 4G9, 5C11 or 5G3 mAb were added to wells, incubated at ambient temperature for 60 minutes, washed and detected with HRP-conjugated goat anti-mouse IgG and developed with TMB microwell peroxidase substrate. Development was terminated by addition of IM O-phosphoric acid and absorbance read at 450 nM on a Spectra-Max340 Microplate Reader. Absorbance values are plotted on the ordinate relative to mAb concentration (ng/ml) on the abscissa. Higher absorbance values at lower plate coat concentration and lower amounts of soluble mAb indicate a relative higher binding affinity for 6E6 and 4G9 compared to 5C11 and 5G3

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994): Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to nucleotides (e.g., deoxyribo-nucleotides or ribonucleotides) and polymers thereof in either single-, double- or multiple-stranded form, or comple-ments thereof; or nucleosides (e.g., deoxyribonucleosides or ribonucleosides). In embodiments, "nucleic acid" does not include nucleosides. The terms "polynucleotide," "oligo-nucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a polynucle-otide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phos-phothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodi-amidate, phosphorothioate (also known as phosphothioate having double bonded sulfur replacing oxygen in the phos-phate), phosphorodithioate, phosphonocarboxylic acids, phosphonocarboxylates, phosphonoacetic acid, phosphono-formic acid, methyl phosphonate, boron phosphonate, or O-methylphosphoroamidite linkages (see Eckstein, OLIGO-NUCLEOTIDES AND ANALOGUES: A PRACTICAL APPROACH, Oxford University Press) as well as modifi-cations to the nucleotide bases such as in 5-methyl cytidine or pseudouridine.; and peptide nucleic acid backbones and linkages. Other analog nucleic acids include those with positive backbones: non-ionic backbones, modified sugars, and non-ribose backbones (e.g. phosphorodiamidate mor-pholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifica-tions of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phos-phodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alpha-betical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (match-ing) nucleotide of guanosine is cytosine. Thus, a comple-ment may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the sec-ond nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., ROR-1) in other proteins with different numbering systems. For example, by performing a simple sequence alignment with a protein (e.g., ROR-1) the identity and location of residues corresponding to specific positions of the protein are identified in other protein sequences aligning to the protein. For example, a selected residue in a selected protein corresponds to glutamic acid at position 138 when the selected residue occupies the same essential spatial or other structural relationship as a glutamic acid at position 138. In some embodiments, where a selected protein is aligned for maximum homology with a protein, the position in the aligned selected protein aligning with glutamic acid 138 is the to correspond to glutamic acid 138. Instead of a primary sequence alignment, a three dimensional structural alignment can also be used, e.g., where the structure of the selected protein is aligned for maximum correspondence with the glutamic acid at position 138, and the overall structures compared. In this case, an amino acid that occupies the same essential position as glutamic acid 138 in the structural model is the to correspond to the glutamic acid 138 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V);

6) Phenylalanine (F), Tyrosine (Y), Tryptophan (W);

7) Serine(S), Threonine (T); and

8) Cysteine (C), Methionine (M)

(see. e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see. e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2: 482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0)). For amino acid sequences, a scoring matrix is used to calculate the cumulative score. Extension of the word hits in each direction are halted when: the cumulative alignment score falls off by the quantity X from its maximum achieved value: the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see. e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). Within each light or heavy chain variable region, there are three short segments (averaging 10) amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, monospecific $Fab_2$, bispecific $Fab_2$, trispecific $Fab_3$, monovalent IgGs, scFv, bispecific antibodies, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The terms "FR L1", "FR L2", "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1", "FR H2", "FR H3" and "FR H4" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FR H4.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)). The term "antibody" as referred to herein further includes antibody variants such as single domain antibodies. Thus, in embodiments an antibody includes a single monomeric variable antibody domain. Thus, in embodiments, the antibody, includes a variable light chain (VL) domain or a variable heavy chain (VH) domain. In embodiments, the antibody is a variable light chain (VL) domain or a variable heavy chain (VH) domain.

For preparation of monoclonal or polyclonal antibodies, any technique known in the art can be used (see, e.g., Kohler & Milstein, Nature 256:495-497 (1975); Kozbor et al.,

*Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or over-lapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, mono-clonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morri-son, Nature 368:812-13 (1994); Fishwild et al., Nature Biotechnology 14:845-51 (1996); Neuberger, Nature Bio-technology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Trau-necker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360: WO 92/200373; and EP 03089).

Methods for humanizing or primatizing non-human anti-bodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoven et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially per-formed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immu-nol., 44:65-92 (1988), Verhoeven et al., Science 239:1534-1536 (1988) and Presta, Curr. Op. Struct. Biol. 2:593-596 (1992), Padlan, Molec. Immun., 28:489-498 (1991); Padlan, Molec. Immun., 31 (3): 169-217 (1994)), by substituting rodent CDRs or CDR sequences for the corresponding sequences of a human antibody. Accordingly, such human-ized antibodies are chimeric antibodies (U.S. Pat. No. 4,816, 567), wherein substantially less than an intact human vari-able domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence cod-ing for humanized immunoglobulin framework regions and a second sequence set coding for the desired immunoglobu-lin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.: or (b) the variable region, or a portion thereof, is altered, replaced or exchanged with a variable region having a different or altered antigen speci-ficity. The preferred antibodies of, and for use according to the invention include humanized and/or chimeric monoclo-nal antibodies.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor or antibody, antibody variant, antibody region or fragment thereof.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2$^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to to an antibody.

The term "ROR2 protein" or "ROR2" as used herein includes any of the recombinant or naturally-occurring forms of Receptor tyrosine kinase-like orphan receptor 2, also known as Tyrosine-protein kinase transmembrane receptor ROR2, Neurotrophic tyrosine kinase receptor-related 2, or variants or homologs thereof that maintain ROR2 activity (e.g. within at least 50%, 80%, 90%, 95%, 96%, 97%, 98%, 99% or 100% activity compared to ROR2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ROR2 protein. In embodiments, the ROR2 protein is substantially identical to the protein identified by SEQ ID NO:18. In embodiments, the ROR2 protein is substantially identical to the protein identified by the UniProt reference number Q01974 or a variant or homolog having substantial identity thereto. In embodiments, the ROR2 protein is substantially identical to the protein identified by the UniProt reference number A1L4F5 or a variant or homolog having substantial identity thereto. In embodiments, the ROR2 protein is substantially identical to the protein identified by the UniProt reference number Q8C3W2 or a variant or homolog having substantial identity thereto.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "gene" means the segment of DNA involved in producing a protein: it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See. e.g., Ford et al. (2001) *Gene Therapy* 8:1-4 and Prochiantz (2007) *Nat. Methods* 4:119-20.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

When the label or detectable moiety is a radioactive metal or paramagnetic ion, the agent may be reacted with another long-tailed reagent having a long tail with one or more chelating groups attached to the long tail for binding to these ions. The long tail may be a polymer such as a polylysine, polysaccharide, or other derivatized or derivatizable chain having pendant groups to which the metals or ions may be added for binding. Examples of chelating groups that may be used according to the disclosure include, but are not limited to, ethylenediaminetetraacetic acid (EDTA), diethylenetri-aminepentaacetic acid (DTPA), DOTA, NOTA, NETA, TETA, porphyrins, polyamines, crown ethers, bis-thiosemi-carbazones, polyoximes, and like groups. The chelate is normally linked to the PSMA antibody or functional anti-body fragment by a group, which enables the formation of a bond to the molecule with minimal loss of immunoreac-tivity and minimal aggregation and/or internal cross-linking. The same chelates, when complexed with non-radioactive metals, such as manganese, iron and gadolinium are useful for MRI, when used along with the antibodies and carriers described herein. Macrocyclic chelates such as NOTA, DOTA, and TETA are of use with a variety of metals and radiometals including, but not limited to, radionuclides of gallium, yttrium and copper, respectively. Other ring-type chelates such as macrocyclic polyethers, which are of inter-est for stably binding nuclides, such as $^{223}$Ra for RAIT may be used. In certain embodiments, chelating moieties may be used to attach a PET imaging agent, such as an Al-$^{18}$F complex, to a targeting molecule for use in PET analysis.

"Contacting" is used in accordance with its plain ordinary meaning and refers to the process of allowing at least two distinct species (e.g. antibodies and antigens) to become sufficiently proximal to react, interact, or physically touch. It should be appreciated: however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composi-tion as described herein to interact with a cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Pro-karyotic cells include but are not limited to bacteria. Eukary-otic cells include, but are not limited to, yeast cells and cells derived from plants and animals, for example mammalian, insect (e.g., *spodoptera*) and human cells.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electro-phoresis or high performance liquid chromatography. A protein that is the predominant species present in a prepa-ration is substantially purified.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Simi-larly, a heterologous protein indicates that the protein com-prises two or more subsequences that are not found in the same relationship to each other in nature (e.g., a fusion protein).

The term "exogenous" refers to a molecule or substance (e.g., a compound, nucleic acid or protein) that originates from outside a given cell or organism. For example, an "exogenous promoter" as referred to herein is a promoter that does not originate from the cell or organism it is expressed by. Conversely, the term "endogenous" or "endogenous promoter" refers to a molecule or substance that is native to, or originates within, a given cell or organism.

As defined herein, the term "inhibition", "inhibit", "inhib-iting" and the like in reference to cell proliferation (e.g., cancer cell proliferation) means negatively affecting (e.g., decreasing proliferation) or killing the cell. In some embodi-ments, inhibition refers to reduction of a disease or symp-toms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. ROR2 protein). Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

As defined herein, the term "inhibition", "inhibit", "inhib-iting" and the like in reference to a protein-inhibitor inter-action means negatively affecting (e.g. decreasing) the activ-ity or function of the protein (e.g. ROR2 protein) relative to the activity or function of the protein in the absence of the inhibitor. In embodiments inhibition means negatively affecting (e.g. decreasing) the concentration or levels of ROR2 relative to the concentration or level of the protein in the absence of the inhibitor. In embodiments inhibition refers to reduction of a disease or symptoms of disease. In embodiments, inhibition refers to a reduction in the activity of ROR2. Thus, inhibition includes, at least in part, partially or totally blocking stimulation, decreasing, preventing, or delaying activation, or inactivating, desensitizing, or down-regulating signal transduction or enzymatic activity or the amount of ROR2. In embodiments, inhibition refers to a reduction of activity of ROR2 resulting from a direct interaction (e.g. an inhibitor binds to ROR2). In embodiments, inhibition refers to a reduction of activity of ROR2 from an indirect interaction (e.g. an inhibitor binds to a protein that activates ROR2, thereby preventing target protein activation).

Thus, the terms "inhibitor," "repressor" or "antagonist" or "downregulator" interchangeably refer to a substance capable of detectably decreasing the expression or activity of a given gene or protein (e.g. ROR2 protein). The antagonist can decrease ROR2 expression or activity 10%, 20%, 30%, 40%, 50%, 60%, 70%, 80%, 90% or more in comparison to a control in the absence of the antagonist. In certain instances, ROR2 expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human: cow: dog: cat: a rodent, e.g., guinea pig, rat, mouse: rabbit: or a bird: reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with the compounds or methods provided herein. The disease may be a cancer. The cancer may refer to a solid tumor malignancy. Solid tumor malignancies include malignant tumors that may be devoid of fluids or cysts. For example, the solid tumor malignancy may include breast cancer, ovarian cancer, pancreatic cancer, cervical cancer, gastric cancer, renal cancer, head and neck cancer, bone cancer, skin cancer or prostate cancer. In some further instances, "cancer" refers to human cancers and carcinomas, sarcomas, adenocarcinomas, lymphomas, leukemias, including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including acute myeloid leukemia (AML), ALL, and CML), or multiple myeloma.

As used herein, the term "cancer" refers to all types of cancer, neoplasm or malignant tumors found in mammals (e.g., humans), including leukemia, carcinomas and sarcomas. Exemplary cancers that may be treated with a compound or method provided herein include breast cancer, colon cancer, kidney cancer, leukemia, lung cancer, melanoma, ovarian cancer, prostate cancer, pancreatic cancer, brain cancer, liver cancer, gastric cancer or a sarcoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic: (2) the type of cell involved: myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia. Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma. Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, or carcinoma *villosum*.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g. a protein associated disease, a cancer associated with ROR2 activity, ROR2 associated cancer, ROR2 associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease. For example, a cancer associated with ROR2 activity or function or a ROR2 associated disease (e.g., cancer, inflammatory disease, autoimmune disease, or infectious disease), may be treated with a ROR2 modulator or ROR2 inhibitor, in the instance where increased ROR2 activity or function (e.g. signaling pathway activity) causes the disease (e.g., cancer, inflammatory disease, autoimmune disease, or infectious disease). For example, an inflammatory disease associated with ROR2 activity or function or an ROR2 associated inflammatory disease, may be treated with an ROR2 modulator or ROR2 inhibitor, in the instance where increased ROR2 activity or function (e.g. signaling pathway activity) causes the disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

A "therapeutic agent" as referred to herein, is a composition useful in treating or preventing a disease such as cancer (e.g., leukemia). In embodiments, the therapeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

An "anticancer agent" as used herein refers to a molecule (e.g. compound, peptide, protein, nucleic acid, 0103) used to treat cancer through destruction or inhibition of cancer cells or tissues. Anticancer agents may be selective for certain cancers or certain tissues. In embodiments, anticancer agents herein may include epigenetic inhibitors and multi-kinase inhibit "Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil: abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stemcell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-nl; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin;

streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10) (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA) Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), 30) KAR-2 (Hungarian Academy of Sciences), BSF-223651 (BASF, i.e. ILX-651 and LU-223651). SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A. CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University). Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine. i.e. MF-569). Narcosine (also known as NSC-5366). Nascapine. D-24851 (Asta *Medica*). A-105972 (Abbott). Hemiasterlin. 3-BAABU (Cytoskeleton/Mt. Sinai School of Medicine. i.e. MF-191). TMPN (Arizona State University), Vanadocene acetylacetonate. T-138026 (Tularik), Monsatrol, Inanocine (i.e. NSC-698666), 3-IAABE (Cytoskeleton/Mt. Sinai School of Medicine). A-204197 (Abbott). T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (*Asta medica*), D-68144 (*Asta medica*), Diazonamide A, A-293620 (Abbott), NPI-2350) (Nereus), Taccalonolide A, TUB-245 (Aventis), A-259754 (Abbott), Diozostatin, (–)-Phenylahistin (i.e. NSCL-96F037), D-68838 (*Asta medica*), D-68836 (*Asta medica*), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995: as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Anti-ROR2 Antibodies

Provided herein are, inter alia, antibodies (e.g., humanized antibodies, monoclonal antibodies), antibody fragments (e.g., scFvs) and antibody compositions (e.g., chimeric antigen receptors, bispecific antibodies), which bind human tyrosine kinase-like orphan receptor 2 (ROR2) with high efficiency and specificity. The antibodies and antibody compositions provided herein include novel light and heavy chain domain CDRs and framework regions and have been identified to bind extracellular domains of human ROR2. For example, the antibodies provided herein including embodiments thereof, may bind the Kringle or the Ig-like domain of ROR2 with high affinity and specificity. Further, Applicants have characterized the amino acid residues in the ROR2 extracellular domains, which are important for binding of antibodies as described herein including embodiments thereof. Antibodies specifically binding the epitope described herein including embodiments thereof, are useful for binding human ROR2 with high effectivity and affinity and inhibiting ROR2 signaling in cells expressing ROR2. The antibodies provided herein including embodiments thereof, may be used for diagnostic and therapeutic purposes in cancer and other ROR2-related diseases. The variable light chain and the variable heavy chain domains provided herein may, inter alia, form part of an anti-ROR2 chimeric antigen receptor or an anti-ROR2 bispecific antibody. Furthermore, due to their internalization properties, some of the anti-ROR2 antibodies provided herein may be attached to therapeutic moieties and used as antibody-drug conjugates (ADC), or they may be attached to a detectable moiety and used for diagnostic purposes. The antibodies provided herein including embodiments thereof, have an ability to inhibit migration of ROR2 expressing metastatic cells and therefore are capable of mitigating the risk of metastasis in patients with ROR2-expressing cancer cells Exemplary anti-ROR2 antibodies provided herein are referred to by clone names (e.g., 6E6, 4G9, 5C11 and 5G3). In embodiments, the anti-ROR2 antibody is antibody 6E6. In embodiments, the antibody 6E6 has a heavy chain variable domain of SEQ ID NO:2 and a light variable domain of SEQ ID NO:4. In embodiments, the antibody 6E6 has a heavy chain variable domain and a light chain variable domain, wherein the heavy chain variable domain includes: a CDR H1 as set forth in SEQ ID NO:25, a CDR H2 as set forth in SEQ ID NO:26 and a CDR H3 as set forth in SEQ ID NO:27; and wherein the light chain variable domain includes: a CDR L1 as set forth in SEQ ID NO:28, a CDR L2 as set forth in SEQ ID NO:29, and a CDR L3 as set forth in SEQ ID NO:30. In embodiments, the anti-ROR2 antibody is antibody 4G9. In embodiments, the antibody 4G9 has a heavy chain variable domain of SEQ ID NO:6 and a light variable domain of SEQ ID NO:8. In embodiments, the antibody 4G9 has a heavy chain variable domain and a light chain variable domain, wherein the heavy chain variable domain includes: a CDR H1 as set forth in SEQ ID NO:31, a CDR H2 as set forth in SEQ ID NO:32 and a CDR H3 as set forth in SEQ ID NO:33; and wherein said light chain variable domain includes: a CDR L1 as set forth in SEQ ID NO:34, a CDR L2 as set forth in SEQ ID NO:35, and a CDR L3 as set forth in SEQ ID NO:36. In embodiments, the anti-ROR2 antibody is antibody 5C11. In embodiments, the antibody 5C11 and has a heavy chain variable domain of SEQ ID NO:10 and a light variable domain of SEQ ID NO:12. In embodiments, the antibody 5C11 has a heavy chain variable domain and a light chain variable domain, wherein the heavy chain variable domain includes: a CDR H1 as set forth in SEQ ID NO:37, a CDR H2 as set forth in SEQ ID NO:38 and a CDR H3 as set forth in SEQ ID NO:39; and wherein said light chain variable domain includes: a CDR L1 as set forth in SEQ ID NO:40, a CDR L2 as set forth in SEQ ID NO:41, and a CDR L3 as set forth in SEQ ID NO:42. In embodiments, the anti-ROR2 antibody is antibody 5G3. In embodiments, the antibody 5G3 has a heavy chain variable domain of SEQ ID NO:14 and a light variable domain of SEQ ID NO:16. In embodiments, the antibody 5G3 has a heavy chain variable domain and a light chain variable domain, wherein the heavy chain variable domain includes: a CDR H1 as set forth in SEQ ID NO:43, a CDR H2 as set forth in SEQ ID NO:44 and a CDR H3 as set forth in SEQ ID NO:45; and wherein said light chain variable domain includes: a CDR L1 as set forth in SEQ ID NO:46, a CDR L2 as set forth in SEQ ID NO:47, and a CDR L3 as set forth in SEQ ID NO:48.

In an aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:25, a CDR H2 as set forth in SEQ ID NO:26 and a CDR H3 as set forth in SEQ ID NO:27; and wherein the light chain 30) variable domain includes: a CDR L1 as set forth in SEQ ID NO:28, a CDR L2 as set forth in SEQ ID NO:29, and a CDR L3 as set forth in SEQ ID NO:30.

As described above, a "light chain variable (VL) domain" as provided herein refers to the variable region of the light chain of an antibody, an antibody variant or fragment thereof. Likewise, the "heavy chain variable (VH) domain" as provided herein refers to the variable region of the heavy chain of an antibody, an antibody variant or fragment thereof. The light chain variable domain and the heavy chain variable domain together form the paratope, which binds an antigen (epitope). The paratope or antigen-binding site is formed at the N-terminus of an antibody, an antibody variant or fragment thereof. In embodiments, the light chain variable (VL) domain includes CDR L1, CDR L2, CDR L3 and FR L1, FR L2, FR L3 and FR L4 (framework regions) of an antibody light chain. In embodiments, the heavy chain variable (VH) domain includes CDR H1, CDR H2, CDR H3 and FR H1, FR H2, FR H3 and FR H4 (framework regions) of an antibody heavy chain. In embodiments, the light chain variable (VL) domain and a light chain constant (CL) domain form part of an antibody light chain. In embodiments, the heavy chain variable (VH) domain and a heavy chain constant (CH1) domain form part of an antibody heavy chain. In embodiments, the heavy chain variable (VH) domain and one or more heavy chain constant (CH1, CH2, or CH3) domains form part of an antibody heavy chain. Thus, in embodiments, the light chain variable (VL) domain forms part of an antibody. In embodiments, the heavy chain variable (VH) domain forms part of an antibody. In embodiments, the light chain variable (VL) domain forms part of a therapeutic antibody. In embodiments, the heavy chain variable (VH) domain forms part of a therapeutic antibody. In embodiments, the light chain variable (VL) domain forms part of a human antibody. In embodiments, the heavy chain variable (VH) domain forms part of a human antibody. In embodiments, the light chain variable (VL) domain forms part of a humanized antibody. In embodiments, the heavy chain variable (VH) domain forms part of a humanized antibody. In embodiments, the light chain variable (VL) domain forms part of a chimeric antibody. In embodiments, the heavy chain variable (VH) domain forms part of a chimeric antibody. In embodiments, the light chain variable (VL) domain forms part of an antibody fragment. In embodiments, the heavy chain variable (VH) domain forms part of an antibody fragment. In embodiments, the light chain variable (VL) domain forms part of an antibody variant. In embodiments, the heavy chain variable (VH) domain forms part of an antibody variant. In embodiments, the light chain variable (VL) domain forms part of a Fab. In embodiments, the heavy chain variable (VH) domain forms part of a Fab. In embodiments, the light chain variable (VL) domain forms part of a scFv. In embodiments, the heavy chain variable (VH) domain forms part of a scFv In embodiments, the heavy chain variable domain includes the sequence of SEQ ID NO:2. In embodiments, the heavy chain variable domain is the sequence of SEQ ID NO:2. In embodiments, the light chain variable domain includes the sequence of SEQ ID NO:4. In embodiments, the light chain variable domain is the sequence of SEQ ID NO:4.

In embodiments, the heavy chain variable domain includes a FR H1 as set forth in SEQ ID NO:49, a FR H2 as set forth in SEQ ID NO:50, a FR H3 as set forth in SEQ ID NO:51 and a FR H4 as set forth in SEQ ID NO:52. In embodiments, the light chain variable domain includes a FR L1 as set forth in SEQ ID NO:53, a FR L2 as set forth in SEQ ID NO:54, a FR L3 as set forth in SEQ ID NO:55 and a FR L4 as set forth in SEQ ID NO:56.

In embodiments, the antibody is capable of binding a ROR2 protein. In embodiments, the ROR2 protein is a human ROR2 protein. In embodiments, the antibody binds a ROR2 protein. In embodiments, the ROR2 protein includes the amino acid sequence of SEQ ID NO:18. In embodiments, the antibody is capable of binding an extracellular domain of the ROR2 protein. In embodiments, the antibody binds an extracellular domain of the ROR2 protein. In embodiments, the extracellular domain includes the amino acid sequence of SEQ ID NO:22. In embodiments, the extracellular domain is a Kringle domain. In embodiments the Kringle domain includes the amino acid sequence of SEQ ID NO:113.

In embodiments, the ROR2 protein includes a histidine at a position corresponding to position 349 or an aspartic acid at a position corresponding to position 354 of SEQ ID NO:22. In embodiments, the ROR2 protein includes a histidine at a position corresponding to position 349 and an aspartic acid at a position corresponding to position 354 of SEQ ID NO:22. In embodiments, the ROR2 protein includes a histidine at a position corresponding to position 349 or an aspartic acid at a position corresponding to position 354 of SEQ ID NO:18. In embodiments, the ROR2 protein includes a histidine at a position corresponding to position 349 and an aspartic acid at a position corresponding to position 354 of SEQ ID NO:18.

In embodiments, the antibody does not bind an arginine at a position corresponding to position 349 of SEQ ID NO:20. In embodiments, the antibody does not bind a glutamic acid at a position corresponding to position 354 of SEQ ID NO:20. In embodiments, the antibody does not bind an arginine at a position corresponding to position 349 of SEQ ID NO:24. In embodiments, the antibody does not bind a glutamic acid at a position corresponding to position 354 of SEQ ID NO:24.

The ability of an antibody to bind a specific epitope (e.g., a ROR2 protein, a Kringle domain or Ig-like domain of ROR2) can be described by the equilibrium dissociation constant ($K_D$). The equilibrium dissociation constant ($K_D$) as defined herein is the ratio of the dissociation rate (K-off) and the association rate (K-on) of an antibody to a ROR2 protein. It is described by the following formula: $K_D$=K-off/K-on.

In embodiments, the antibody binds the ROR2 protein with an equilibrium dissociation constant ($K_D$) from 0.01 nM to 10 nM. In embodiments, the antibody binds the ROR2 protein with a $K_D$ from 0).1 nM to 10 nM. In embodiments, the antibody binds the ROR2 protein with a $K_D$ from 0.2 nM to 10 nM. In embodiments, the antibody binds the ROR2 protein with a $K_D$ from 0).3 nM to 10 nM. In embodiments, the antibody binds the ROR2 protein with a $K_D$ from 0).4 nM to 10 nM. In embodiments, the antibody binds the ROR2 protein with a $K_D$ from 0.5 nM to 10 nM. In embodiments, the antibody binds the ROR2 protein with a $K_D$ from 0.6 nM to 10 nM. In embodiments, the antibody binds the ROR2 protein with a $K_D$ from 0.7 nM to 10 nM. In embodiments, the antibody binds the ROR2 protein with a $K_D$ from 0.8 nM to 10 nM. In embodiments, the antibody binds the ROR2 protein with a $K_D$ from 0.9 nM to 1 nM. In embodiments, the antibody binds the ROR2 protein with a $K_D$ from 1 nM to 10 nM. In embodiments, the antibody binds the ROR2 protein with an equilibrium dissociation constant ($K_D$) from 1.1 nM to 10 nM. In embodiments, the antibody binds the ROR2 protein with a $K_D$ from 1.2 nM to 10 nM. In embodiments, the antibody binds the ROR2 protein with a $K_D$ from 1.3 nM to 10 nM. In embodiments, the antibody binds the ROR2 protein with a $K_D$ from 1.4 nM to 10 nM. In embodiments, the antibody binds the ROR2 protein with a $K_D$ from 1.5 nM to 10) nM. In embodiments, the antibody binds the ROR2 protein with a $K_D$ from 1.6 nM to 10 nM. In embodiments, the antibody binds the ROR2 protein with a $K_D$ from 1.7 nM to 10 nM. In embodiments, the antibody binds the ROR2 protein with a $K_D$ from 1.8 nM to 10 nM. In embodiments, the antibody binds the ROR2 protein with a $K_D$ from 1.9 nM to 10 nM. In embodiments, the antibody binds the ROR2 protein with a $K_D$ from 2 nM to 10 nM. In embodiments, the antibody binds the ROR2 protein with an equilibrium dissociation constant ($K_D$) from 2.1 nM to 10 nM. In embodiments, the antibody binds the ROR2 protein with a $K_D$ from 2.2 nM to 10 nM. In embodiments, the antibody binds the ROR2 protein with a $K_D$ from 2.3 nM to 10 nM. In embodiments, the antibody binds the ROR2 protein with a $K_D$ from 2.4 nM to 10 nM. In embodiments, the antibody binds the ROR2 protein with a $K_D$ from 2.5 nM to 10) nM. In embodiments, the antibody binds the ROR2 protein with a $K_D$ from 2.6 nM to 10 nM. In embodiments, the antibody binds the ROR2 protein with a $K_D$ from 2.7 nM to 10 nM. In embodiments, the antibody binds the ROR2 protein with a $K_D$ from 2.8 nM to 10 nM. In embodiments, the antibody binds the ROR2 protein with a $K_D$ from 2.9 nM to 10 nM. In embodiments, the antibody binds the ROR2 protein with a $K_D$ from 3 nM to 10 nM. In embodiments, the antibody binds the ROR2 protein with an equilibrium dissociation constant ($K_D$) from 4.1 nM to 10 nM. In embodiments, the antibody binds the ROR2 protein with a $K_D$ from 4.2 nM to 10 nM. In embodiments, the antibody binds the ROR2 protein with a $K_D$ from 4.3 nM to 10 nM. In embodiments, the antibody binds the ROR2 protein with a $K_D$ from 4.4 nM to 10 nM. In embodiments, the antibody binds the ROR2 protein with a $K_D$ from 4.5 nM to 10 nM. In embodiments, the antibody binds the ROR2 protein with a $K_D$ from 4.6 nM to 10 nM. In embodiments, the antibody binds the ROR2 protein with a $K_D$ from 4.7 nM to 10 nM. In embodiments, the antibody binds the ROR2 protein with a $K_D$ from 4.8 nM to 10 nM. In embodiments, the antibody binds the ROR2 protein with a $K_D$ from 4.9 nM to 10 nM. In embodiments, the antibody binds the ROR2 protein with a $K_D$ from 5 nM to 10 nM. In embodiments, the antibody binds the ROR2 protein with an equilibrium dissociation constant ($K_D$) from 5.1 nM to 10 nM. In embodiments, the antibody binds the ROR2 protein with a $K_D$ from 5.2 nM to 10 nM. In embodiments, the antibody binds the ROR2 protein with a $K_D$ from 5.3 nM to 10 nM. In embodiments, the antibody binds the ROR2 protein with a $K_D$ from 5.4 nM to 10 nM. In embodiments, the antibody binds the ROR2 protein with a $K_D$ from 5.5 nM to 10 nM. In embodiments, the antibody binds the ROR2 protein with a $K_D$ from 5.6 nM to 10 nM. In embodiments, the antibody binds the ROR2 protein with a $K_D$ from 5.7 nM to 10 nM. In embodiments, the antibody binds the ROR2 protein with a $K_D$ from 5.8 nM to 10 nM. In embodiments, the antibody binds the ROR2 protein with a $K_D$ from 5.9 nM to 10 nM. In embodiments, the antibody binds the ROR2 protein with a $K_D$ from 6 nM to 10 nM. In embodiments, the antibody binds the ROR2 protein with an equilibrium dissociation constant ($K_D$) from 6.1 nM to 10 nM. In embodiments, the antibody binds the ROR2 protein with a $K_D$ from 6.2 nM to 10 nM. In embodiments, the antibody binds the ROR2 protein with a $K_D$ from 6.3 nM to 10 nM. In embodiments, the antibody binds the ROR2 protein with a $K_D$ from 6.4 nM to 10 nM. In embodiments, the antibody binds the ROR2 protein with a $K_D$ from 6.5 nM to 10 nM. In embodiments, the antibody binds the ROR2 protein with a Ko from 6.6 nM to 10 nM. In embodiments, the antibody binds the ROR2 protein with a $K_D$ from 6.7 nM to 10 nM. In embodiments, the antibody binds the ROR2 protein with a $K_D$ from 6.8 nM to 10 nM. In embodiments, the antibody binds the ROR2 protein with a $K_D$ from 6.9 nM to 10 nM. In embodiments, the antibody binds the ROR2 protein with a $K_D$ from 7 nM to 10 nM. In embodiments, the antibody binds the ROR2 protein with an equilibrium dissociation constant ($K_D$) from 7.1 nM to 10 nM. In embodiments, the antibody binds the ROR2 protein with a $K_D$ from 7.2 nM to 10 nM. In embodiments, the antibody binds the ROR2 protein with a $K_D$ from 7.3 nM to 10 nM. In embodiments, the antibody binds the ROR2 protein with a $K_D$ from 7.4 nM to 10 nM. In embodiments, the antibody binds the ROR2 protein with a $K_D$ from 7.5 nM to 10 nM. In embodiments, the antibody binds the ROR2 protein with a $K_D$ from 7.6 nM to 10 nM. In embodiments, the antibody binds the ROR2 protein with a $K_D$ from 7.7 nM to 10 nM. In embodiments, the antibody binds the ROR2 protein with a $K_D$ from 7.8 nM to 10 nM. In embodiments, the antibody binds the ROR2 protein with a $K_D$ from 7.9 nM to 10 nM. In embodiments, the antibody binds the ROR2 protein with a $K_D$ from 8 nM to 10 nM. In embodiments, the antibody binds the ROR2 protein with an equilibrium dissociation constant ($K_D$) from 8.1 nM to 10 nM. In embodiments, the antibody binds the ROR2 protein with a $K_D$ from 8.2 nM to 10 nM. In embodiments, the antibody binds the ROR2 protein with a $K_D$ from 8.3 nM to 10 nM. In embodiments, the antibody binds the ROR2 protein with a $K_D$ from 8.4 nM to 10 nM. In embodiments, the antibody binds the ROR2 protein with a $K_D$ from 8.5 nM to 10) nM. In embodiments, the antibody binds the ROR2 protein with a $K_D$ from 8.6 nM to 10 nM. In embodiments, the antibody binds the ROR2 protein with a $K_D$ from 8.7 nM to 10 nM. In embodiments, the antibody binds the ROR2 protein with a $K_D$ from 8.8 nM to 10 nM. In embodiments, the antibody binds the ROR2 protein with a $K_D$ from 8.9 nM to 10 nM. In embodiments, the antibody binds the ROR2 protein with a $K_D$ from 9 nM to 10 nM. In embodiments, the antibody binds the ROR2 protein with an equilibrium dissociation constant ($K_D$) from 9.1 nM to 10 nM. In embodiments, the antibody binds the ROR2 protein with a $K_D$ from 9.2 nM to 10 nM. In embodiments, the antibody binds the ROR2 protein with a $K_D$ from 9.3 nM to 10 nM. In embodiments, the antibody binds the ROR2 protein with a $K_D$ from 9.4 nM to 10 nM. In embodiments, the antibody binds the ROR2 protein with a $K_D$ from 9.5 nM to 10 nM. In embodiments, the antibody binds the ROR2 protein with a $K_D$ from 9.6 nM to 10 nM. In embodiments, the antibody binds the ROR2 protein with a $K_D$ from 9.7 nM to 10 nM. In embodiments, the antibody binds the ROR2 protein with a $K_D$ from 9.8 nM to 10 nM. In embodiments, the antibody binds the ROR2 protein with a $K_D$ from 9.9 nM to 10 nM.

In embodiments, the antibody binds the ROR2 protein with a $K_D$ from 0.01 nM to 9.9 nM. In embodiments, the antibody binds the ROR2 protein with a $K_D$ from 0.01 nM to 9.8 nM. In embodiments, the antibody binds the ROR2 protein with a $K_D$ from 0.01 nM to 9.7 nM. In embodiments, the antibody binds the ROR2 protein with a $K_D$ from 0.01 nM to 9.6 nM. In embodiments, the antibody binds the ROR2 protein with a $K_D$ from 0.01 nM to 9.5 nM. In embodiments, the antibody binds the ROR2 protein with a $K_D$ from 0.01 nM to 9.4 nM. In embodiments, the antibody binds the ROR2 protein with a $K_D$ from 0.01 nM to 9.3 nM. In embodiments, the antibody binds the ROR2 protein with a $K_D$ from 0.01 nM to 9.2 nM. In embodiments, the antibody binds the ROR2 protein with a $K_D$ from 0.01 nM to 9.1 nM. In embodiments, the antibody binds the ROR2 protein with a $K_D$ from 0.01 nM to 9 nM. In embodiments, the antibody binds the ROR2 protein with a $K_D$ from 0.01 nM to 8.9 nM. In embodiments, the antibody binds the ROR2 protein with a $K_D$ from 0.01 nM to 8.8 nM. In embodiments, the antibody binds the ROR2 protein with a $K_D$ from 0.01 nM to 8.7 nM. In embodiments, the antibody binds the ROR2 protein with a $K_D$ from 0.01 nM to 8.6 nM. In embodiments, the antibody binds the ROR2 protein with a $K_D$ from 0.01 nM to 8.5 nM. In embodiments, the antibody binds the ROR2 protein with a $K_D$ from 0.01 nM to 8.4 nM. In embodiments, the antibody binds the ROR2 protein with a $K_D$ from 0.01 nM to 8.3 nM. In embodiments, the antibody binds the ROR2 protein with a $K_D$ from 0.01 nM to 8.2 nM. In embodiments, the antibody binds the ROR2 protein with a $K_D$ from 0.01 nM to 8.1 nM. In embodiments, the antibody binds the ROR2 protein with a $K_D$ from 0.01 nM to 8 nM. In embodiments, the antibody binds the ROR2 protein with a $K_D$ from 0.01 nM to 7.9 nM. In embodiments, the antibody binds the ROR2 protein with a $K_D$ from 0.01 nM to 7.8 nM. In embodiments, the antibody binds the ROR2 protein with a $K_D$ from 0.01 nM to 7.7 nM. In embodiments, the antibody binds the ROR2 protein with a $K_D$ from 0.01 nM to 7.6 nM. In embodiments, the antibody binds the ROR2 protein with a $K_D$ from 0.01 nM to 7.5 nM. In embodiments, the antibody binds the ROR2 protein with a $K_D$ from 0.01 nM to 7.4 nM. In embodiments, the antibody binds the ROR2 protein with a $K_D$ from 0.01 nM to 7.3 nM. In embodiments, the antibody binds the ROR2 protein with a $K_D$ from 0.01 nM to 7.2 nM. In embodiments, the antibody binds the ROR2 protein with a $K_D$ from 0.01 nM to 7.1 nM. In embodiments, the antibody binds the ROR2 protein with a $K_D$ from 0.01 nM to 7 nM. In embodiments, the antibody binds the ROR2 protein with a $K_D$ from 0.01 nM to 6.9 nM. In embodiments, the antibody binds the ROR2 protein with a $K_D$ from 0.01 nM to 6.8 nM. In embodiments, the antibody binds the ROR2 protein with a $K_D$ from 0.01 nM to 6.7 nM. In embodiments, the antibody binds the ROR2 protein with a $K_D$ from 0.01 nM to 6.6 nM. In embodiments, the antibody binds the ROR2 protein with a $K_D$ from 0.01 nM to 6.5 nM. In embodiments, the antibody binds the ROR2 protein with a $K_D$ from 0.01 nM to 6.4 nM. In embodiments, the antibody binds the ROR2 protein with a $K_D$ from 0.01 nM to 6.3 nM. In embodiments, the antibody binds the ROR2 protein with a $K_D$ from 0.01 nM to 6.2 nM. In embodiments, the antibody binds the ROR2 protein with a $K_D$ from 0.01 nM to 6.1 nM. In embodiments, the antibody binds the ROR2 protein with a $K_D$ from 0.01 nM to 6 nM. In embodiments, the antibody binds the ROR2 protein with a $K_D$ from 0.01 nM to 5.9 nM. In embodiments, the antibody binds the ROR2 protein with a $K_D$ from 0.01 nM to 5.8 nM. In embodiments, the antibody binds the ROR2 protein with a $K_D$ from 0.01 nM to 5.7 nM. In embodiments, the antibody binds the ROR2 protein with a $K_D$ from 0.01 nM to 5.6 nM. In embodiments, the antibody binds the ROR2 protein with a $K_D$ from 0.01 nM to 5.5 nM. In embodiments, the antibody binds the ROR2 protein with a $K_D$ from 0.01 nM to 5.4 nM. In embodiments, the antibody binds the ROR2 protein with a $K_D$ from 0.01 nM to 5.3 nM. In embodiments, the antibody binds the ROR2 protein with a $K_D$ from 0.01 nM to 5.2 nM. In embodiments, the antibody binds the ROR2 protein with a $K_D$ from 0.01 nM to 5.1 nM. In embodiments, the antibody binds the ROR2 protein with a $K_D$ from 0.01 nM to 5 nM. In embodiments, the antibody binds the ROR2 protein with a $K_D$ from 0.01 nM to 4.9 nM. In embodiments, the antibody binds the ROR2 protein with a $K_D$ from 0.01 nM to 4.8 nM. In embodiments, the antibody binds the ROR2 protein with a $K_D$ from 0.01 nM to 4.7 nM. In embodiments, the antibody binds the ROR2 protein with a $K_D$ from 0.01 nM to 4.6 nM. In embodiments, the antibody binds the ROR2 protein with a $K_D$ from 0.01 nM to 4.5 nM.

In embodiments, the antibody binds the ROR2 protein with a $K_D$ from 0.01 nM to 4.4 nM. In embodiments, the antibody binds the ROR2 protein with a $K_D$ from 0.01 nM to 4.3 nM. In embodiments, the antibody binds the ROR2 protein with a $K_D$ from 0.01 nM to 4.2 nM. In embodiments, the antibody binds the ROR2 protein with a $K_D$ from 0.01 nM to 4.1 nM. In embodiments, the antibody binds the ROR2 protein with a $K_D$ from 0.01 nM to 4 nM. In embodiments, the antibody binds the ROR2 protein with a $K_D$ from 0.01 nM to 3.9 nM. In embodiments, the antibody binds the ROR2 protein with a $K_D$ from 0.01 nM to 3.8 nM. In embodiments, the antibody binds the ROR2 protein with a $K_D$ from 0.01 nM to 3.7 nM. In embodiments, the antibody binds the ROR2 protein with a $K_D$ from 0.01 nM to 3.6 nM. In embodiments, the antibody binds the ROR2 protein with a $K_D$ from 0.01 nM to 3.5 nM. In embodiments, the antibody binds the ROR2 protein with a $K_D$ from 0.01 nM to 3.4 nM. In embodiments, the antibody binds the ROR2 protein with a $K_D$ from 0.01 nM to 3.3 nM. In embodiments, the antibody binds the ROR2 protein with a $K_D$ from 0.01 nM to 3.2 nM. In embodiments, the antibody binds the ROR2 protein with a $K_D$ from 0.01 nM to 3.1 nM. In embodiments, the antibody binds the ROR2 protein with a $K_D$ from 0.01 nM to 3 nM. In embodiments, the antibody binds the ROR2 protein with a $K_D$ from 0.01 nM to 2.9 nM. In embodiments, the antibody binds the ROR2 protein with a $K_D$ from 0.01 nM to 2.8 nM. In embodiments, the antibody binds the ROR2 protein with a $K_D$ from 0.01 nM to 2.7 nM. In embodiments, the antibody binds the ROR2 protein with a $K_D$ from 0.01 nM to 2.6 nM. In embodiments, the antibody binds the ROR2 protein with a $K_D$ from 0.01 nM to 2.5 nM. In embodiments, the antibody binds the ROR2 protein with a $K_D$ from 0.01 nM to 2.4 nM. In embodiments, the antibody binds the ROR2 protein with a $K_D$ from 0.01 nM to 2.3 nM. In embodiments, the antibody binds the ROR2 protein with a $K_D$ from 0.01 nM to 2.2 nM. In embodiments, the antibody binds the ROR2 protein with a $K_D$ from 0.01 nM to 2.1 nM. In embodiments, the antibody binds the ROR2 protein with a $K_D$ from 0.01 nM to 2 nM. In embodiments, the antibody binds the ROR2 protein with a $K_D$ from 0.01 nM to 1.9 nM. In embodiments, the antibody binds the ROR2 protein with a $K_D$ from 0.01 nM to 1.8 nM. In embodiments, the antibody binds the ROR2 protein with a $K_D$ from 0.01 nM to 1.7 nM. In embodiments, the antibody binds the ROR2 protein with a $K_D$ from 0.01 nM to 1.6 nM. In embodiments, the antibody binds the ROR2 protein with a $K_D$ from 0.01 nM to 1.5 nM. In embodiments, the antibody binds the ROR2 protein with a $K_D$ from 0.01 nM to 1.4 nM. In embodiments, the antibody binds the ROR2 protein with a $K_D$ from 0.01 nM to 1.3 nM. In embodiments, the antibody binds the ROR2 protein with a $K_D$ from 0.01 nM to 1.2 nM. In embodiments, the antibody binds the ROR2 protein with a $K_D$ from 0.01 nM to 1.1 nM. In embodiments, the antibody binds the ROR2 protein with a $K_D$ from 0.01 nM to 0.9 nM. In embodiments, the antibody binds the ROR2 protein with a $K_D$ from 0.01 nM to 0.8 nM. In embodiments, the antibody binds the ROR2 protein with a $K_D$ from 0.01 nM to 0.7 nM. In embodiments, the antibody binds the ROR2 protein with a $K_D$ from 0.01 nM to 0.6 nM. In embodiments, the antibody binds the ROR2 protein with a $K_D$ from 0.01 nM to 0.5 nM. In embodiments, the antibody binds the ROR2 protein with a $K_D$ from 0.01 nM to 0.4 nM. In embodiments, the antibody binds the ROR2 protein with a $K_D$ from 0.01 nM to 0.3 nM. In embodiments, the antibody binds the ROR2 protein with a $K_D$ from 0.01 nM to 0.2 nM. In embodiments, the antibody binds the ROR2 protein with a $K_D$ from 0.01 nM to 0.1 nM.

In embodiments, the antibody binds the ROR2 protein with a a $K_D$ of 0.01, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 nM.

In embodiments, the antibody binds the ROR2 protein with a $K_D$ of about 0.06 nM. In embodiments, the antibody is antibody 6E6 and binds a ROR2 protein with a $K_D$ of 0.01 nM to 10 nM. In embodiments, the antibody 6E6 binds a ROR2 protein with a $K_D$ of 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 nM. In embodiments, the antibody is antibody 6E6 and binds a ROR2 protein with a $K_D$ of 0.06 nM.

In embodiments, the antibody is attached to a therapeutic agent. In embodiments, the antibody is attached to a diagnostic agent. In embodiments, the diagnostic agent is a detectable moiety.

In one embodiment, the antibody has a heavy chain variable domain of SEQ ID NO:2 and a light chain variable domain of SEQ ID NO:4. In one embodiment, the antibody includes (i) a heavy chain variable domain including a CDR H1 as set forth in SEQ ID NO:25, a CDR H2 as set forth in SEQ ID NO:26: a CDR H3 as set forth in SEQ ID NO:27; a FR H1 as set forth in SEQ ID NO:49, a FR H2 as set forth in SEQ ID NO:50, a FR H3 as set forth in SEQ ID NO:51 and a FR H4 as set forth in SEQ ID NO:52; and (ii) a light chain variable domain including a CDR L1 as set forth in SEQ ID NO:28, a CDR L2 as set forth in SEQ ID NO:29, a CDR L3 as set forth in SEQ ID NO:30; a FR L1 as set forth in SEQ ID NO:53, a FR L2 as set forth in SEQ ID NO:54, a FR L3 as set forth in SEQ ID NO:55 and a FR L4 as set forth in SEQ ID NO:56. In one further embodiment, the antibody is antibody 6E6.

In an aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:31, a CDR H2 as set forth in SEQ ID NO:32 and a CDR H3 as set forth in SEQ ID NO:33; and wherein the light chain variable domain includes: a CDR L1 as set forth in SEQ ID NO:34, a CDR L2 as set forth in SEQ ID NO:35, and a CDR L3 as set forth in SEQ ID NO:36.

In embodiments, the heavy chain variable domain includes the sequence of SEQ ID NO:6. In embodiments, the heavy chain variable domain is the sequence of SEQ ID NO:6. In embodiments, the light chain variable domain includes the sequence of SEQ ID NO:8. In embodiments, the light chain variable domain is the sequence of SEQ ID NO:8.

In embodiments, the heavy chain variable domain includes a FR H1 as set forth in SEQ ID NO:57, a FR H2 as set forth in SEQ ID NO:58, a FR H3 as set forth in SEQ ID NO:59 and a FR H4 as set forth in SEQ ID NO:60. In embodiments, the light chain variable domain includes a FR L1 as set forth in SEQ ID NO:61, a FR L2 as set forth in SEQ ID NO:62, a FR L3 as set forth in SEQ ID NO:63 and a FR L4 as set forth in SEQ ID NO:64.

In embodiments, the antibody is capable of binding a ROR2 protein. In embodiments, the the ROR2 protein is a human ROR2 protein. In embodiments, the antibody binds a ROR2 protein. In embodiments, the ROR2 protein includes the amino acid sequence of SEQ ID NO:18. In embodiments, the antibody is capable of binding an extracellular domain of the ROR2 protein. In embodiments, the antibody binds an extracellular domain of the ROR2 protein. In embodiments, the extracellular domain includes the amino acid sequence of SEQ ID NO:22. In embodiments, the extracellular domain is an Ig-like domain. In embodiments, the Ig-like domain includes the amino acid sequence of SEQ ID NO:114.

In embodiments, the ROR2 protein includes a methionine at a position corresponding to position 386 of SEQ ID NO:22. In embodiments, the ROR2 protein includes a methionine at a position corresponding to position 386 of SEQ ID NO:18.

In embodiments, the antibody does not bind a valine at a position corresponding to position 349 of SEQ ID NO:20. In embodiments, the antibody does not bind a valine at a position corresponding to position 349 of SEQ ID NO:24.

In embodiments, the antibody binds the ROR2 protein with a $K_D$ from 0.2 nM to 5 nM. In embodiments, the antibody binds the ROR2 protein with a $K_D$ from 0.6 nM to 5 nM. In embodiments, the antibody binds the ROR2 protein with a $K_D$ from 1 nM to 5 nM. In embodiments, the antibody binds the ROR2 protein with a $K_D$ from 1.4 nM to 5 nM. In embodiments, the antibody binds the ROR2 protein with a $K_D$ from 1.8 nM to 5 nM. In embodiments, the antibody binds the ROR2 protein with a $K_D$ from 2.2 nM to 5 nM. In embodiments, the antibody binds the ROR2 protein with a $K_D$ from 2.6 nM to 5 nM. In embodiments, the antibody binds the ROR2 protein with a $K_D$ from 3 nM to 5 nM. In embodiments, the antibody binds the ROR2 protein with a $K_D$ from 3.4 nM to 5 nM. In embodiments, the antibody binds the ROR2 protein with a $K_D$ from 3.8 nM to nM. In embodiments, the antibody binds the ROR2 protein with a $K_D$ from 4.2 nM to 5 nM. In embodiments, the antibody binds the ROR2 protein with a $K_D$ from 4.6 nM to 5 nM.

In embodiments, the antibody binds the ROR2 protein with a $K_D$ from 0.2 nM to 4.6 nM. In embodiments, the antibody binds the ROR2 protein with a $K_D$ from 0.2 nM to 4.2 nM. In embodiments, the antibody binds the ROR2 protein with a $K_D$ from 0.2 nM to 3.8 nM. In embodiments, the antibody binds the ROR2 protein with a $K_D$ from 0.2 nM to 3.4 nM. In embodiments, the antibody binds the ROR2 protein with a $K_D$ from 0.2 nM to 3 nM. In embodiments, the antibody binds the ROR2 protein with a $K_D$ from 0.2 nM to 2.6 nM. In embodiments, the antibody binds the ROR2 protein with a $K_D$ from 0.2 nM to 2.2 nM. In embodiments, the antibody binds the ROR2 protein with a $K_D$ from 0.2 nM to 1.8 nM. In embodiments, the antibody binds the ROR2 protein with a $K_D$ from 0.2 nM to 1.4 nM. In embodiments, the antibody binds the ROR2 protein with a $K_D$ from 0.2 nM to 1 nM. In embodiments, the antibody binds the ROR2 protein with a $K_D$ from 0.2 nM to 0.6 nM.

In embodiments, the antibody binds the ROR2 protein with a $K_D$ from 0.1 nM to 10 nM. In embodiments, the antibody binds the ROR2 protein with a $K_D$ from 0.5 nM to 10 nM. In embodiments, the antibody binds the ROR2 protein with a $K_D$ from 1 nM to 10 nM. In embodiments, the antibody binds the ROR2 protein with a $K_D$ from 1.5 nM to 10 nM. In embodiments, the antibody binds the ROR2 protein with a $K_D$ from 2 nM to 10 nM. In embodiments, the antibody binds the ROR2 protein with a $K_D$ from 2.5 nM to 10 nM. In embodiments, the antibody binds the ROR2 protein with a $K_D$ from 3 nM to 10 nM. In embodiments, the antibody binds the ROR2 protein with a $K_D$ from 3.5 nM to 10 nM. In embodiments, the antibody binds the ROR2 protein with a $K_D$ from 4 nM to 10 nM. In embodiments, the antibody binds the ROR2 protein with a $K_D$ from 4.5 nM to 10 nM. In embodiments, the antibody binds the ROR2 protein with a $K_D$ from 5 nM to 10 nM. In embodiments, the antibody binds the ROR2 protein with a $K_D$ from 5.5 nM to 10 nM. In embodiments, the antibody binds the ROR2 protein with a $K_D$ from 6 nM to 10 nM. In embodiments, the antibody binds the ROR2 protein with a $K_D$ from 6.5 nM to 10 nM. In embodiments, the antibody binds the ROR2 protein with a $K_D$ from 7 nM to 10 nM. In embodiments, the antibody binds the ROR2 protein with a $K_D$ from 7.5 nM to 10 nM. In embodiments, the antibody binds the ROR2 protein with a $K_D$ from 8 nM to 10 nM. In embodiments, the antibody binds the ROR2 protein with a $K_D$ from 8.5 nM to 10 nM. In embodiments, the antibody binds the ROR2 protein with a $K_D$ from 9 nM to 10 nM.

In embodiments, the antibody binds the ROR2 protein with a $K_D$ from 0.1 nM to 9.5 nM. In embodiments, the antibody binds the ROR2 protein with a $K_D$ from 0.1 nM to 9 nM. In embodiments, the antibody binds the ROR2 protein with a $K_D$ from 0.1 nM to 8.5 nM. In embodiments, the antibody binds the ROR2 protein with a $K_D$ from 0.1 nM to 8 nM. In embodiments, the antibody binds the ROR2 protein with a $K_D$ from 0.1 nM to 7.5 nM. In embodiments, the antibody binds the ROR2 protein with a $K_D$ from 0.1 nM to 7 nM. In embodiments, the antibody binds the ROR2 protein with a $K_D$ from 0.1 nM to 6.5 nM. In embodiments, the antibody binds the ROR2 protein with a $K_D$ from 0.1 nM to 6 nM. In embodiments, the antibody binds the ROR2 protein with a $K_D$ from 0.1 nM to 5.5 nM. In embodiments, the antibody binds the ROR2 protein with a $K_D$ from 0.1 nM to 5 nM. In embodiments, the antibody binds the ROR2 protein with a $K_D$ from 0.1 nM to 4.5 nM. In embodiments, the antibody binds the ROR2 protein with a $K_D$ from 0.1 nM to 4 nM. In embodiments, the antibody binds the ROR2 protein with a $K_D$ from 0.1 nM to 3.5 nM. In embodiments, the antibody binds the ROR2 protein with a $K_D$ from 0.1 nM to 3 nM. In embodiments, the antibody binds the ROR2 protein with a $K_D$ from 0.1 nM to 2.5 nM. In embodiments, the antibody binds the ROR2 protein with a $K_D$ from 0.1 nM to 2 nM. In embodiments, the antibody binds the ROR2 protein with a $K_D$ from 0.1 nM to 1.5 nM. In embodiments, the antibody binds the ROR2 protein with a $K_D$ from 0.1 nM to 1 nM.

In embodiments, the antibody binds the ROR2 protein with a a $K_D$ of 0.1, 0.4, 0.8, 1.2, 1.6, 2, 2.4, 2.8, 3.2, 3.6, 4, 4.4, 4.8, 5.2, 5.6, 6, 6.4, 6.8, 7.2, 7.6, 8, 8.4, 8.8, 9.2, 9.6, or 10 nM.

In embodiments, the antibody binds the ROR2 protein with a $K_D$ of about 1.9 nM. In embodiments, the antibody is antibody 4G9 and binds a ROR2 protein with a $K_D$ of 0.1 nM to 10 nM. In embodiments, the antibody 4G9 binds a ROR2 protein with a $K_D$ of 0.1, 0.4, 0.8, 1.2, 1.6, 2, 2.4, 2.8, 3.2, 3.6, 4, 4.4, 4.8, 5.2, 5.6, 6, 6.4, 6.8, 7.2, 7.6, 8, 8.4, 8.8, 9.2, 9.6, or 10 nM. In embodiments, the antibody is antibody 4G9 and binds a ROR2 protein with a $K_D$ of 1.9 nM.

In embodiments, the antibody is attached to a therapeutic agent. In embodiments, the antibody is attached to a diagnostic agent. In embodiments, the diagnostic agent is a detectable moiety.

In one embodiment, the antibody has a heavy chain variable domain of SEQ ID NO:6 and a light chain variable domain of SEQ ID NO:8. In one embodiment, the antibody includes (i) a heavy chain variable domain including a CDR H1 as set forth in SEQ ID NO:31, a CDR H2 as set forth in SEQ ID NO:32: a CDR H3 as set forth in SEQ ID NO:33: a FR H1 as set forth in SEQ ID NO:57, a FR H2 as set forth in SEQ ID NO:58, a FR H3 as set forth in SEQ ID NO:59 and a FR H4 as set forth in SEQ ID NO:60; and (ii) a light chain variable domain including a CDR L1 as set forth in SEQ ID NO:34, a CDR L2 as set forth in SEQ ID NO:35, a CDR L3 as set forth in SEQ ID NO:36; a FR L1 as set forth in SEQ ID NO:61, a FR L2 as set forth in SEQ ID NO:62, a FR L3 as set forth in SEQ ID NO:63 and a FR L4 as set forth in SEQ ID NO:64. In one further embodiment, the antibody is antibody 4G9.

In an aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:37, a CDR H2 as set forth in SEQ ID NO:38 and a CDR H3 as set forth in SEQ ID NO:39; and wherein the light chain variable domain includes: a CDR L1 as set forth in SEQ ID NO:40, a CDR L2 as set forth in SEQ ID NO:41, and a CDR L3 as set forth in SEQ ID NO:42.

In embodiments, the heavy chain variable domain includes the sequence of SEQ ID NO:10. In embodiments, the heavy chain variable domain is the sequence of SEQ ID NO:10. In embodiments, the light chain variable domain includes the sequence of SEQ ID NO:12. In embodiments, the light chain variable domain is the sequence of SEQ ID NO:12.

In embodiments, the heavy chain variable domain includes a FR H1 as set forth in SEQ ID NO:65, a FR H2 as set forth in SEQ ID NO:66, a FR H3 as set forth in SEQ ID NO:67 and a FR H4 as set forth in SEQ ID NO:68. In embodiments, the light chain variable domain includes a FR L1 as set forth in SEQ ID NO:69, a FR L2 as set forth in SEQ ID NO:70, a FR L3 as set forth in SEQ ID NO:71 and a FR L4 as set forth in SEQ ID NO:72.

In embodiments, the antibody is capable of binding a ROR2 protein. In embodiments, the the ROR2 protein is a human ROR2 protein. In embodiments, the antibody binds a ROR2 protein. In embodiments, the ROR2 protein includes the amino acid sequence of SEQ ID NO:18. In embodiments, the antibody is capable of binding an extracellular domain of the ROR2 protein. In embodiments, the antibody binds an extracellular domain of the ROR2 protein. In embodiments, the extracellular domain includes the amino acid sequence of SEQ ID NO:22. In embodiments, the extracellular domain is a Kringle domain. In embodiments the Kringle domain includes the amino acid sequence of SEQ ID NO:113.

In embodiments, the ROR2 protein includes a histidine at a position corresponding to position 349, an aspartic acid at a position corresponding to position 354, or a methionine at a position corresponding to position 386 of SEQ ID NO:22. In embodiments, the ROR2 protein includes a histidine at a position corresponding to position 349, an aspartic acid at a position corresponding to position 354, and a methionine at a position corresponding to position 386 of SEQ ID NO:22. In embodiments, the ROR2 protein includes a histidine at a position corresponding to position 349, an aspartic acid at a position corresponding to position 354, or a methionine at a position corresponding to position 386 of SEQ ID NO:18. In embodiments, the ROR2 protein includes a histidine at a position corresponding to position 349, an aspartic acid at a position corresponding to position 354, and a methionine at a position corresponding to position 386 of SEQ ID NO:18.

In embodiments, the antibody does not bind an arginine at a position corresponding to position 349 of SEQ ID NO:20. In embodiments, the antibody does not bind a glutamic acid at a position corresponding to position 354 of SEQ ID NO:20. In embodiments, the antibody does not bind a valine at a position corresponding to position 386 of SEQ ID NO:20. In embodiments, the antibody does not bind an arginine at a position corresponding to position 349 of SEQ ID NO:24. In embodiments, the antibody does not bind a glutamic acid at a position corresponding to position 354 of SEQ ID NO:24. In embodiments, the antibody does not bind a valine at a position corresponding to position 386 of SEQ ID NO:24.

In embodiments, the antibody binds the ROR2 protein with a $K_D$ from 10 nM to 150 nM. In embodiments, the antibody binds the ROR2 protein with a $K_D$ from 20 nM to 150 nM. In embodiments, the antibody binds the ROR2 protein with a $K_D$ from 30 nM to 150 nM. In embodiments, the antibody binds the ROR2 protein with a $K_D$ from 40 nM to 150 nM. In embodiments, the antibody binds the ROR2 protein with a $K_D$ from 50 nM to 150 nM. In embodiments, the antibody binds the ROR2 protein with a $K_D$ from 60 nM to 150 nM. In embodiments, the antibody binds the ROR2 protein with a $K_D$ from 70 nM to 150 nM. In embodiments, the antibody binds the ROR2 protein with a $K_D$ from 80 nM to 150 nM. In embodiments, the antibody binds the ROR2 protein with a $K_D$ from 90 nM to 150 nM. In embodiments, the antibody binds the ROR2 protein with a $K_D$ from 100 nM to 150 nM. In embodiments, the antibody binds the ROR2 protein with a $K_D$ from 110 nM to 150 nM. In embodiments, the antibody binds the ROR2 protein with a $K_D$ from 120 nM to 150 nM. In embodiments, the antibody binds the ROR2 protein with a $K_D$ from 130 nM to 150 nM. In embodiments, the antibody binds the ROR2 protein with a $K_D$ from 140 nM to 150 nM.

In embodiments, the antibody binds the ROR2 protein with a $K_D$ from 10 nM to 140 nM. In embodiments, the antibody binds the ROR2 protein with a $K_D$ from 10 nM to 130 nM. In embodiments, the antibody binds the ROR2 protein with a $K_D$ from 10 nM to 120 nM. In embodiments, the antibody binds the ROR2 protein with a $K_D$ from 10 nM to 110 nM. In embodiments, the antibody binds the ROR2 protein with a $K_D$ from 10 nM to 100 nM. In embodiments, the antibody binds the ROR2 protein with a $K_D$ from 10 nM to 90 nM. In embodiments, the antibody binds the ROR2 protein with a $K_D$ from 10 nM to 80 nM. In embodiments, the antibody binds the ROR2 protein with a $K_D$ from 10 nM to 70 nM. In embodiments, the antibody binds the ROR2 protein with a $K_D$ from 10 nM to 60 nM. In embodiments, the antibody binds the ROR2 protein with a $K_D$ from 10 nM to 50 nM. In embodiments, the antibody binds the ROR2 protein with a $K_D$ from 10 nM to 40 nM. In embodiments, the antibody binds the ROR2 protein with a $K_D$ from 10 nM to 30 nM. In embodiments, the antibody binds the ROR2 protein with a $K_D$ from 10 nM to 20 nM. In embodiments, the antibody binds the ROR2 protein with a a $K_D$ of 10, 20, 30, 40, 50, 60, 70, 80, 90, 100, 110, 120, 130, 140 or 150 nM.

In embodiments, the antibody is 5C11 and binds a ROR2 protein with a $K_D$ of 10, 20, 30, 40, 50, 60, 70, 80, 90, 100, 110, 120, 130, 140 or 150 nM.

In embodiments, the antibody is attached to a therapeutic agent. In embodiments, the antibody is attached to a diagnostic agent. In embodiments, the diagnostic agent is a detectable moiety.

In one embodiment, the antibody has a heavy chain variable domain of SEQ ID NO:10 and a light chain variable domain of SEQ ID NO:12. In one embodiment, the antibody includes (i) a heavy chain variable domain including a CDR H1 as set forth in SEQ ID NO:37, a CDR H2 as set forth in SEQ ID NO:38: a CDR H3 as set forth in SEQ ID NO:39; a FR H1 as set forth in SEQ ID NO:65, a FR H2 as set forth in SEQ ID NO:66, a FR H3 as set forth in SEQ ID NO:67 and a FR H4 as set forth in SEQ ID NO:68; and (ii) a light chain variable domain including a CDR L1 as set forth in SEQ ID NO:40, a CDR L2 as set forth in SEQ ID NO:41, a CDR L3 as set forth in SEQ ID NO:42: a FR L1 as set forth in SEQ ID NO:69, a FR L2 as set forth in SEQ ID NO:70, a FR L3 as set forth in SEQ ID NO:71 and a FR L4 as set forth in SEQ ID NO:72. In one further embodiment, the antibody is antibody 5C11.

In an aspect is provided an anti-tyrosine kinase-like orphan receptor 2 (ROR2) antibody including a heavy chain variable domain and a light chain variable domain, wherein the heavy chain variable domain includes: a CDR H1 as set forth in SEQ ID NO:43, a CDR H2 as set forth in SEQ ID NO:44 and a CDR H3 as set forth in SEQ ID NO:45; and wherein the light chain variable domain includes: a CDR L1 as set forth in SEQ ID NO:46, a CDR L2 as set forth in SEQ ID NO:47, and a CDR L3 as set forth in SEQ ID NO:48.

In embodiments, the heavy chain variable domain includes the sequence of SEQ ID NO:14. In embodiments, the heavy chain variable domain is the sequence of SEQ ID NO:14. In embodiments, the light chain variable domain includes the sequence of SEQ ID NO:16. In embodiments, the light chain variable domain is the sequence of SEQ ID NO:16.

In embodiments, the heavy chain variable domain includes a FR H1 as set forth in SEQ ID NO:73, a FR H2 as set forth in SEQ ID NO:74, a FR H3 as set forth in SEQ ID NO:75 and a FR H4 as set forth in SEQ ID NO:76. In embodiments, the light chain variable domain includes a FR L1 as set forth in SEQ ID NO:77, a FR L2 as set forth in SEQ ID NO:78, a FR L3 as set forth in SEQ ID NO:79 and a FR L4 as set forth in SEQ ID NO:80.

In embodiments, the antibody is capable of binding a ROR2 protein. In embodiments, the ROR2 protein is a human ROR2 protein. In embodiments, the antibody binds a ROR2 protein. In embodiments, the ROR2 protein includes the amino acid sequence of SEQ ID NO:18. In embodiments, the antibody is capable of binding an extracellular domain of the ROR2 protein. In embodiments, the antibody binds an extracellular domain of the ROR2 protein. In embodiments, the extracellular domain includes the amino acid sequence of SEQ ID NO:22. In embodiments, the extracellular domain is an Ig-like domain. In embodiments, the Ig-like domain includes includes the amino acid sequence of SEQ ID NO:114.

In embodiments, the antibody binds the ROR2 protein with a $K_D$ from 10 nM to 150 nM. In embodiments, the antibody binds the ROR2 protein with a $K_D$ from 20 nM to 150 nM. In embodiments, the antibody binds the ROR2 protein with a $K_D$ from 30 nM to 150 nM. In embodiments, the antibody binds the ROR2 protein with a $K_D$ from 40 nM to 150 nM. In embodiments, the antibody binds the ROR2 protein with a $K_D$ from 50 nM to 150 nM. In embodiments, the antibody binds the ROR2 protein with a $K_D$ from 60 nM to 150 nM. In embodiments, the antibody binds the ROR2 protein with a $K_D$ from 70 nM to 150 nM. In embodiments, the antibody binds the ROR2 protein with a $K_D$ from 80 nM to 150 nM. In embodiments, the antibody binds the ROR2 protein with a $K_D$ from 90 nM to 150 nM. In embodiments, the antibody binds the ROR2 protein with a $K_D$ from 100 nM to 150 nM. In embodiments, the antibody binds the ROR2 protein with a $K_D$ from 110 nM to 150 nM. In embodiments, the antibody binds the ROR2 protein with a $K_D$ from 120 nM to 150 nM. In embodiments, the antibody binds the ROR2 protein with a $K_D$ from 130 nM to 150 nM. In embodiments, the antibody binds the ROR2 protein with a $K_D$ from 140 nM to 150 nM.

In embodiments, the antibody binds the ROR2 protein with a $K_D$ from 10 nM to 140 nM. In embodiments, the antibody binds the ROR2 protein with a $K_D$ from 10 nM to 130 nM. In embodiments, the antibody binds the ROR2 protein with a $K_D$ from 10 nM to 120 nM. In embodiments, the antibody binds the ROR2 protein with a $K_D$ from 10 nM to 110 nM. In embodiments, the antibody binds the ROR2 protein with a $K_D$ from 10 nM to 100 nM. In embodiments, the antibody binds the ROR2 protein with a $K_D$ from 10 nM to 90 nM. In embodiments, the antibody binds the ROR2 protein with a $K_D$ from 10 nM to 80 nM. In embodiments, the antibody binds the ROR2 protein with a $K_D$ from 10 nM to 70 nM. In embodiments, the antibody binds the ROR2 protein with a $K_D$ from 10 nM to 60 nM. In embodiments, the antibody binds the ROR2 protein with a $K_D$ from 10 nM to 50 nM. In embodiments, the antibody binds the ROR2 protein with a $K_D$ from 10 nM to 40 nM. In embodiments, the antibody binds the ROR2 protein with a $K_D$ from 10 nM to 30 nM. In embodiments, the antibody binds the ROR2 protein with a $K_D$ from 10 nM to 20 nM. In embodiments, the antibody binds the ROR2 protein with a a $K_D$ of 10, 20, 30, 40, 50, 60, 70, 80, 90, 100, 110, 120, 130, 140 or 150 nM.

In embodiments, the antibody is 5G3 and binds a ROR2 protein with a $K_D$ of 10, 20, 30, 40, 50, 60, 70, 80, 90, 100, 110, 120, 130, 140 or 150 nM.

In embodiments, the antibody is attached to a therapeutic agent. In embodiments, the antibody is attached to a diagnostic agent. In embodiments, the diagnostic agent is a detectable moiety.

In one embodiment, the antibody has a heavy chain variable domain of SEQ ID NO:14 and a light chain variable domain of SEQ ID NO:16. In one embodiment, the antibody includes (i) a heavy chain variable domain including a CDR H1 as set forth in SEQ ID NO:43, a CDR H2 as set forth in SEQ ID NO:44: a CDR H3 as set forth in SEQ ID NO:45: a FR H1 as set forth in SEQ ID NO:73, a FR H2 as set forth in SEQ ID NO:74, a FR H3 as set forth in SEQ ID NO:75 and a FR H4 as set forth in SEQ ID NO:76; and (ii) a light chain variable domain including a CDR L1 as set forth in SEQ ID NO:46, a CDR L2 as set forth in SEQ ID NO:47, a CDR L3 as set forth in SEQ ID NO:48: a FR L1 as set forth in SEQ ID NO:77, a FR L2 as set forth in SEQ ID NO:78, a FR L3 as set forth in SEQ ID NO:79 and a FR L4 as set forth in SEQ ID NO:80. In one further embodiment, the antibody is antibody 5G3.

The antibodies provided herein including embodiments thereof (e.g., antibody 6e6, 4G9, 5C11 or 5G3), may be humanized antibodies. Thus, in embodiments, the antibody is a humanized antibody. In embodiments, the antibody is a chimeric antibody. In embodiments, antibody is a Fab' fragment. In embodiments, the antibody is an IgG. In embodiments, the antibody is an IgG. The anti-ROR2 antibody provided herein may be an IgG1, IgG2, IgG3 or IgG4. In embodiments, the antibody is an IgG1. In embodiments, the antibody is an IgG2. In embodiments, the antibody is an IgG2a. In embodiments, the antibody is an IgG3. In embodiments, the antibody is an IgG4.

In embodiments, the antibody does not bind a mouse ROR2 protein. In embodiments, the antibody does not bind a mouse ROR2 protein identified by the UniProt reference number Q9Z138. In embodiments, the antibody provided herein does not bind a protein comprising the amino acid sequence of SEQ ID NO:20. In embodiments, the antibody provided herein does not bind a protein comprising the amino acid sequence of SEQ ID NO:24. In embodiments, the antibody provided herein does not bind the protein of SEQ ID NO:20 or SEQ ID NO:24. In embodiments, the antibody provided herein does not bind the protein of SEQ ID NO:20. In embodiments, the antibody provided herein does not bind the protein of SEQ ID NO:24.

In an aspect is provided the ROR2 protein bound by the antibodies provided herein including embodiments thereof (e.g., antibody 6e6, 4G9, 5C11 or 5G3) may be expressed by a cell (e.g., cancer cell). Thus, in embodiments, the ROR2 protein is expressed on a cell. In embodiments, the cell is a cancer cell. In embodiments, the cancer cell is cancer is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell. In embodiments, the cancer cell is a breast cancer cell. In embodiments, the cancer cell is an ovarian cancer cell. In embodiments, the cancer cell is a pancreatic cancer cell. In embodiments, the cancer cell is cancer is a cervical cancer cell. In embodiments, the cancer cell is cancer is a gastric cancer cell. In embodiments, the cancer cell is cancer is a renal cancer cell. In embodiments, the cancer cell is cancer is a head and neck cancer cell. In embodiments, the cancer cell is a cancer is bone cancer cell. In embodiments, the cancer cell is cancer is a skin cancer cell. In embodiments, the cancer cell is cancer is a prostate cancer cell.

In embodiments, the antibody provided herein (e.g., antibody 6E6, 4G9, 5C11 or 5G3) does not bind a ROR2-negative cell. A "ROR2-negative cell" as provided herein is a cell that does not express a detectable amount of a ROR2 protein relative to a standard control. In embodiments, the expression level of a ROR2-negative cell is undetectable using methods conventionally known in the art to a detect protein expression in a cell (e.g., immunofluorescent detection, protein biochemistry, RNA expression level). In embodiments, the expression level of a ROR2-negative cell is 1000, 500, 100, 50, 25, 20, 10, 5, or 1.5 times lower than the expression level of a standard control (e.g., a cell expressing detectable levels of ROR2 using conventional methods). No limiting examples of ROR2-negative cells include a peripheral blood mononuclear cell (PBMC) from a healthy subject.

Any of the variable light chain domain or the variable heavy chain of the antibodies provided herein may form part of an scFv. Thus, in embodiments, the antibody is a single chain antibody (scFv). In embodiments, the light chain variable domain and the heavy chain variable domain form part of a scFv. In embodiments, a linker forms part of the scFv. In embodiments, the linker includes the sequence of SEQ ID NO:82. In embodiments, a leader peptide forms part of the scFv. In embodiments, the leader peptide includes the sequence of SEQ ID NO:81. In embodiments, the scFv further includes a heavy chain constant region (CH2-CH3). In embodiments, the heavy chain constant region includes the sequence of SEQ ID NO:84.

In embodiments, the scFv includes the sequence of SEQ ID NO:85. In embodiments, the scFv is the sequence of SEQ ID NO:85.

In embodiments, the scFv binds the ROR2 protein with an equilibrium dissociation constant ($K_D$) from 0.01 nM to 10 nM. In embodiments, the scFv binds the ROR2 protein with a $K_D$ from 0.1 nM to 10 nM. In embodiments, the scFv binds the ROR2 protein with a $K_D$ from 0.2 nM to 10 nM. In embodiments, the scFv binds the ROR2 protein with a $K_D$ from 0.3 nM to 10 nM. In embodiments, the scFv binds the ROR2 protein with a $K_D$ from 0.4 nM to 10 nM. In embodiments, the scFv binds the ROR2 protein with a $K_D$ from 0.5 nM to 10 nM. In embodiments, the scFv binds the ROR2 protein with a $K_D$ from 0.6 nM to 10 nM. In embodiments, the scFv binds the ROR2 protein with a $K_D$ from 0.7 nM to 10 nM. In embodiments, the scFv binds the ROR2 protein with a $K_D$ from 0.8 nM to 10 nM. In embodiments, the scFv binds the ROR2 protein with a $K_D$ from 0.9 nM to 1 nM. In embodiments, the scFv binds the ROR2 protein with a $K_D$ from 1 nM to 10 nM. In embodiments, the scFv binds the ROR2 protein with a $K_D$ from 1.1 nM to 10 nM. In embodiments, the scFv binds the ROR2 protein with a $K_D$ from 1.2 nM to 10 nM. In embodiments, the scFv binds the ROR2 protein with a $K_D$ from 1.3 nM to 10 nM. In embodiments, the scFv binds the ROR2 protein with a $K_D$ from 1.4 nM to 10 nM. In embodiments, the scFv binds the ROR2 protein with a $K_D$ from 1.5 nM to 10 nM. In embodiments, the scFv binds the ROR2 protein with a $K_D$ from 1.6 nM to 10 nM. In embodiments, the scFv binds the ROR2 protein with a $K_D$ from 1.7 nM to 10 nM. In embodiments, the scFv binds the ROR2 protein with a $K_D$ from 1.8 nM to 10 nM. In embodiments, the scFv binds the ROR2 protein with a $K_D$ from 1.9 nM to 10 nM. In embodiments, the scFv binds the ROR2 protein with a $K_D$ from 2 nM to 10 nM. In embodiments, the scFv binds the ROR2 protein with a $K_D$ from 2.1 nM to 10 nM. In embodiments, the scFv binds the ROR2 protein with a $K_D$ from 2.2 nM to 10 nM. In embodiments, the scFv binds the ROR2 protein with a $K_D$ from 2.3 nM to 10 nM. In embodiments, the scFv binds the ROR2 protein with a $K_D$ from 2.4 nM to 10 nM. In embodiments, the scFv binds the ROR2 protein with a $K_D$ from 2.5 nM to 10 nM. In embodiments, the scFv binds the ROR2 protein with a $K_D$ from 2.6 nM to 10 nM. In embodiments, the scFv binds the ROR2 protein with a $K_D$ from 2.7 nM to 10 nM. In embodiments, the scFv binds the ROR2 protein with a $K_D$ from 2.8 nM to 10 nM. In embodiments, the scFv binds the ROR2 protein with a $K_D$ from 2.9 nM to 10 nM. In embodiments, the scFv binds the ROR2 protein with a $K_D$ from 3 nM to 10 nM. In embodiments, the scFv binds the ROR2 protein with a $K_D$ from 3.1 nM to 10 nM. In embodiments, the scFv binds the ROR2 protein with a $K_D$ from 3.2 nM to 10 nM. In embodiments, the scFv binds the ROR2 protein with a $K_D$ from 3.3 nM to 10 nM. In embodiments, the scFv binds the ROR2 protein with a $K_D$ from 3.4 nM to 10 nM. In embodiments, the scFv binds the ROR2 protein with a $K_D$ from 3.5 nM to 10 nM. In embodiments, the scFv binds the ROR2 protein with a $K_D$ from 3.6 nM to 10 nM. In embodiments, the scFv binds the ROR2 protein with a $K_D$ from 3.7 nM to 10 nM. In embodiments, the scFv binds the ROR2 protein with a $K_D$ from 3.8 nM to 10 nM. In embodiments, the scFv binds the ROR2 protein with a $K_D$ from 3.9 nM to 10 nM. In embodiments, the scFv binds the ROR2 protein with a $K_D$ from 4 nM to 10 nM. In embodiments, the scFv binds the ROR2 protein with a $K_D$ from 4.1 nM to 10 nM. In embodiments, the scFv binds the ROR2 protein with a $K_D$ from 4.2 nM to 10 nM. In embodiments, the scFv binds the ROR2 protein with a $K_D$ from 4.3 nM to 10 nM. In embodiments, the scFv binds the ROR2 protein with a $K_D$ from 4.4 nM to 10 nM. In embodiments, the scFv binds the ROR2 protein with a $K_D$ from 4.5 nM to 10 nM. In embodiments, the scFv binds the ROR2 protein with a $K_D$ from 4.6 nM to 10 nM. In embodiments, the scFv binds the ROR2 protein with a $K_D$ from 4.7 nM to 10 nM. In embodiments, the scFv binds the ROR2 protein with a $K_D$ from 4.8 nM to 10 nM. In embodiments, the scFv binds the ROR2 protein with a $K_D$ from 4.9 nM to 10 nM. In embodiments, the scFv binds the ROR2 protein with a $K_D$ from 5 nM to 10 nM. In embodiments, the scFv binds the ROR2 protein with a $K_D$ from 5.1 nM to 10 nM. In embodiments, the scFv binds the ROR2 protein with a $K_D$ from 5.2 nM to 10 nM. In embodiments, the scFv binds the ROR2 protein with a $K_D$ from 5.3 nM to 10 nM. In embodiments, the scFv binds the ROR2 protein with a $K_D$ from 5.4 nM to 10 nM. In embodiments, the scFv binds the ROR2 protein with a $K_D$ from 5.5 nM to 10 nM. In embodiments, the scFv binds the ROR2 protein with a $K_D$ from 5.6 nM to 10 nM. In embodiments, the scFv binds the ROR2 protein with a $K_D$ from 5.7 nM to 10 nM. In embodiments, the scFv binds the ROR2 protein with a $K_D$ from 5.8 nM to 10 nM. In embodiments, the scFv binds the ROR2 protein with a $K_D$ from 5.9 nM to 10 nM. In embodiments, the scFv binds the ROR2 protein with a $K_D$ from 6 nM to 10 nM. In embodiments, the scFv binds the ROR2 protein with a $K_D$ from 6.1 nM to 10 nM. In embodiments, the scFv binds the ROR2 protein with a $K_D$ from 6.2 nM to 10 nM. In embodiments, the scFv binds the ROR2 protein with a $K_D$ from 6.3 nM to 10 nM. In embodiments, the scFv binds the ROR2 protein with a $K_D$ from 6.4 nM to 10 nM. In embodiments, the scFv binds the ROR2 protein with a $K_D$ from 6.5 nM to 10 nM. In embodiments, the scFv binds the ROR2 protein with a $K_D$ from 6.6 nM to 10 nM. In embodiments, the scFv binds the ROR2 protein with a $K_D$ from 6.7 nM to 10 nM. In embodiments, the scFv binds the ROR2 protein with a $K_D$ from 6.8 nM to 10 nM. In embodiments, the scFv binds the ROR2 protein with a $K_D$ from 6.9 nM to 10 nM. In embodiments, the scFv binds the ROR2 protein with a $K_D$ from 7 nM to 10 nM. In embodiments, the scFv binds the ROR2 protein with a $K_D$ from 7.1 nM to 10 nM. In embodiments, the scFv binds the ROR2 protein with a $K_D$ from 7.2 nM to 10 nM. In embodiments, the scFv binds the ROR2 protein with a $K_D$ from 7.3 nM to 10 nM. In embodiments, the scFv binds the ROR2 protein with a $K_D$ from 7.4 nM to 10 nM. In embodiments, the scFv binds the ROR2 protein with a $K_D$ from 7.5 nM to 10 nM. In embodiments, the scFv binds the ROR2 protein with a $K_D$ from 7.6 nM to 10 nM. In embodiments, the scFv binds the ROR2 protein with a $K_D$ from 7.7 nM to 10 nM. In embodiments, the scFv binds the ROR2 protein with a $K_D$ from 7.8 nM to 10 nM. In embodiments, the scFv binds the ROR2 protein with a $K_D$ from 7.9 nM to 10 nM. In embodiments, the scFv binds the ROR2 protein with a $K_D$ from 8 nM to 10 nM. In embodiments, the scFv binds the ROR2 protein with a $K_D$ from 8.1 nM to 10 nM. In embodiments, the scFv binds the ROR2 protein with a $K_D$ from 8.2 nM to 10 nM. In embodiments, the scFv binds the ROR2 protein with a $K_D$ from 8.3 nM to 10 nM. In embodiments, the scFv binds the ROR2 protein with a $K_D$ from 8.4 nM to 10 nM. In embodiments, the scFv binds the ROR2 protein with a $K_D$ from 8.5 nM to 10 nM. In embodiments, the scFv binds the ROR2 protein with a $K_D$ from 8.6 nM to 10 nM. In embodiments, the scFv binds the ROR2 protein with a $K_D$ from 8.7 nM to 10 nM. In embodiments, the scFv binds the ROR2 protein with a $K_D$ from 8.8 nM to 10 nM. In embodiments, the scFv binds the ROR2 protein with a $K_D$ from 8.9 nM to 10 nM. In embodiments, the scFv binds the ROR2 protein with a $K_D$ from 9 nM to 10 nM. In embodiments, the scFv binds the ROR2 protein with a $K_D$ from 9.1 nM to 10 nM. In embodiments, the scFv binds the ROR2 protein with a $K_D$ from 9.2 nM to 10 nM. In embodiments, the scFv binds the ROR2 protein with a $K_D$ from 9.3 nM to 10 nM. In embodiments, the scFv binds the ROR2 protein with a $K_D$ from 9.4 nM to 10 nM. In embodiments, the scFv binds the ROR2 protein with a $K_D$ from 9.5 nM to 10 nM. In embodiments, the scFv binds the ROR2 protein with a $K_D$ from 9.6 nM to 10 nM. In embodiments, the scFv binds the ROR2 protein with a $K_D$ from 9.7 nM to 10 nM. In embodiments, the scFv binds the ROR2 protein with a $K_D$ from 9.8 nM to 10 nM. In embodiments, the scFv binds the ROR2 protein with a $K_D$ from 9.9 nM to 10 nM.

In embodiments, the scFv binds the ROR2 protein with a $K_D$ from 0.01 nM to 9.9 nM. In embodiments, the scFv binds the ROR2 protein with a $K_D$ from 0.01 nM to 9.8 nM. In embodiments, the scFv binds the ROR2 protein with a $K_D$ from 0.01 nM to 9.7 nM. In embodiments, the scFv binds the ROR2 protein with a $K_D$ from 0.01 nM to 9.6 nM. In embodiments, the scFv binds the ROR2 protein with a $K_D$ from 0.01 nM to 9.5 nM. In embodiments, the scFv binds the ROR2 protein with a $K_D$ from 0.01 nM to 9.4 nM. In embodiments, the scFv binds the ROR2 protein with a $K_D$ from 0.01 nM to 9.3 nM. In embodiments, the scFv binds the ROR2 protein with a $K_D$ from 0.01 nM to 9.2 nM. In embodiments, the scFv binds the ROR2 protein with a $K_D$ from 0.01 nM to 9.1 nM. In embodiments, the scFv binds the ROR2 protein with a $K_D$ from 0.01 nM to 9 nM. In embodiments, the scFv binds the ROR2 protein with a $K_D$ from 0.01 nM to 8.9 nM. In embodiments, the scFv binds the ROR2 protein with a $K_D$ from 0.01 nM to 8.8 nM. In embodiments, the scFv binds the ROR2 protein with a $K_D$ from 0.01 nM to 8.7 nM. In embodiments, the scFv binds the ROR2 protein with a $K_D$ from 0.01 nM to 8.6 nM. In embodiments, the scFv binds the ROR2 protein with a $K_D$ from 0.01 nM to 8.5 nM. In embodiments, the scFv binds the ROR2 protein with a $K_D$ from 0.01 nM to 8.4 nM. In embodiments, the scFv binds the ROR2 protein with a $K_D$ from 0.01 nM to 8.3 nM. In embodiments, the scFv binds the ROR2 protein with a $K_D$ from 0.01 nM to 8.2 nM. In embodiments, the scFv binds the ROR2 protein with a $K_D$ from 0.01 nM to 8.1 nM. In embodiments, the scFv binds the ROR2 protein with a $K_D$ from 0.01 nM to 8 nM. In embodiments, the scFv binds the ROR2 protein with a $K_D$ from 0.01 nM to 7.9 nM. In embodiments, the scFv binds the ROR2 protein with a $K_D$ from 0.01 nM to 7.8 nM. In embodiments, the scFv binds the ROR2 protein with a $K_D$ from 0.01 nM to 7.7 nM. In embodiments, the scFv binds the ROR2 protein with a $K_D$ from 0.01 nM to 7.6 nM. In embodiments, the scFv binds the ROR2 protein with a $K_D$ from 0.01 nM to 7.5 nM. In embodiments, the scFv binds the ROR2 protein with a $K_D$ from 0.01 nM to 7.4 nM. In embodiments, the scFv binds the ROR2 protein with a $K_D$ from 0.01 nM to 7.3 nM. In embodiments, the scFv binds the ROR2 protein with a $K_D$ from 0.01 nM to 7.2 nM. In embodiments, the scFv binds the ROR2 protein with a $K_D$ from 0.01 nM to 7.1 nM. In embodiments, the scFv binds the ROR2 protein with a $K_D$ from 0.01 nM to 7 nM. In embodiments, the scFv binds the ROR2 protein with a $K_D$ from 0.01 nM to 6.9 nM. In embodiments, the scFv binds the ROR2 protein with a $K_D$ from 0.01 nM to 6.8 nM. In embodiments, the scFv binds the ROR2 protein with a $K_D$ from 0.01 nM to 6.7 nM. In embodiments, the scFv binds the ROR2 protein with a $K_D$ from 0.01 nM to 6.6 nM. In embodiments, the scFv binds the ROR2 protein with a $K_D$ from 0.01 nM to 6.5 nM. In embodiments, the scFv binds the ROR2 protein with a $K_D$ from 0.01 nM to 6.4 nM. In embodiments, the scFv binds the ROR2 protein with a $K_D$ from 0.01 nM to 6.3 nM. In embodiments, the scFv binds the ROR2 protein with a $K_D$ from 0.01 nM to 6.2 nM. In embodiments, the scFv binds the ROR2 protein with a $K_D$ from 0.01 nM to 6.1 nM. In embodiments, the scFv binds the ROR2 protein with a $K_D$ from 0.01 nM to 6 nM. In embodiments, the scFv binds the ROR2 protein with a $K_D$ from 0.01 nM to 5.9 nM. In embodiments, the scFv binds the ROR2 protein with a $K_D$ from 0.01 nM to 5.8 nM. In embodiments, the scFv binds the ROR2 protein with a $K_D$ from 0.01 nM to 5.7 nM. In embodiments, the scFv binds the ROR2 protein with a $K_D$ from 0.01 nM to 5.6 nM. In embodiments, the scFv binds the ROR2 protein with a $K_D$ from 0.01 nM to 5.5 nM. In embodiments, the scFv binds the ROR2 protein with a $K_D$ from 0.01 nM to 5.4 nM. In embodiments, the scFv binds the ROR2 protein with a $K_D$ from 0.01 nM to 5.3 nM. In embodiments, the scFv binds the ROR2 protein with a $K_D$ from 0.01 nM to 5.2 nM. In embodiments, the scFv binds the ROR2 protein with a $K_D$ from 0.01 nM to 5.1 nM. In embodiments, the scFv binds the ROR2 protein with a $K_D$ from 0.01 nM to 5 nM. In embodiments, the scFv binds the ROR2 protein with a $K_D$ from 0.01 nM to 4.9 nM. In embodiments, the scFv binds the ROR2 protein with a $K_D$ from 0.01 nM to 4.8 nM. In embodiments, the scFv binds the ROR2 protein with a $K_D$ from 0.01 nM to 4.7 nM. In embodiments, the scFv binds the ROR2 protein with a $K_D$ from 0.01 nM to 4.6 nM. In embodiments, the scFv binds the ROR2 protein with a $K_D$ from 0.01 nM to 4.5 nM. In embodiments, the scFv binds the ROR2 protein with a $K_D$ from 0.01 nM to 4.4 nM. In embodiments, the scFv binds the ROR2 protein with a $K_D$ from 0.01 nM to 4.3 nM. In embodiments, the scFv binds the ROR2 protein with a $K_D$ from 0.01 nM to 4.2 nM. In embodiments, the scFv binds the ROR2 protein with a $K_D$ from 0.01 nM to 4.1 nM. In embodiments, the scFv binds the ROR2 protein with a $K_D$ from 0.01 nM to 4 nM. In embodiments, the scFv binds the ROR2 protein with a $K_D$ from 0.01 nM to 3.9 nM. In embodiments, the scFv binds the ROR2 protein with a $K_D$ from 0.01 nM to 3.8 nM. In embodiments, the scFv binds the ROR2 protein with a $K_D$ from 0.01 nM to 3.7 nM. In embodiments, the scFv binds the ROR2 protein with a $K_D$ from 0.01 nM to 3.6 nM. In embodiments, the scFv binds the ROR2 protein with a $K_D$ from 0.01 nM to 3.5 nM. In embodiments, the scFv binds the ROR2 protein with a $K_D$ from 0.01 nM to 3.4 nM. In embodiments, the scFv binds the ROR2 protein with a $K_D$ from 0.01 nM to 3.3 nM. In embodiments, the scFv binds the ROR2 protein with a $K_D$ from 0.01 nM to 3.2 nM. In embodiments, the scFv binds the ROR2 protein with a $K_D$ from 0.01 nM to 3.1 nM. In embodiments, the scFv binds the ROR2 protein with a $K_D$ from 0.01 nM to 3 nM. In embodiments, the scFv binds the ROR2 protein with a $K_D$ from 0.01 nM to 2.9 nM. In embodiments, the scFv binds the ROR2 protein with a $K_D$ from 0.01 nM to 2.8 nM. In embodiments, the scFv binds the ROR2 protein with a $K_D$ from 0.01 nM to 2.7 nM. In embodiments, the scFv binds the ROR2 protein with a $K_D$ from 0.01 nM to 2.6 nM. In embodiments, the scFv binds the ROR2 protein with a $K_D$ from 0.01 nM to 2.5 nM. In embodiments, the scFv binds the ROR2 protein with a $K_D$ from 0.01 nM to 2.4 nM. In embodiments, the scFv binds the ROR2 protein with a $K_D$ from 0.01 nM to 2.3 nM. In embodiments, the scFv binds the ROR2 protein with a $K_D$ from 0.01 nM to 2.2 nM. In embodiments, the scFv binds the ROR2 protein with a $K_D$ from 0.01 nM to 2.1 nM. In embodiments, the scFv binds the ROR2 protein with a $K_D$ from 0.01 nM to 2 nM. In embodiments, the scFv binds the ROR2 protein with a $K_D$ from 0.01 nM to 1.9 nM. In embodiments, the scFv binds the ROR2 protein with a $K_D$ from 0.01 nM to 1.8 nM. In embodiments, the scFv binds the ROR2 protein with a $K_D$ from 0.01 nM to 1.7 nM. In embodiments, the scFv binds the ROR2 protein with a $K_D$ from 0.01 nM to 1.6 nM. In embodiments, the scFv binds the ROR2 protein with a $K_D$ from 0.01 nM to 1.5 nM. In embodiments, the scFv binds the ROR2 protein with a $K_D$ from 0.01 nM to 1.4 nM. In embodiments, the scFv binds the ROR2 protein with a $K_D$ from 0.01 nM to 1.3 nM. In embodiments, the scFv binds the ROR2 protein with a $K_D$ from 0.01 nM to 1.2 nM. In embodiments, the scFv binds the ROR2 protein with a $K_D$ from 0.01 nM to 1.1 nM. In embodiments, the scFv binds the ROR2 protein with a $K_D$ from 0.01 nM to 0.9 nM. In embodiments, the scFv binds the ROR2 protein with a $K_D$ from 0.01 nM to 0.8 nM. In embodiments, the scFv binds the ROR2 protein with a $K_D$ from 0.01 nM to 0.7 nM. In embodiments, the scFv binds the ROR2 protein with a $K_D$ from 0.01 nM to 0.6 nM. In embodiments, the scFv binds the ROR2 protein with a $K_D$ from 0.01 nM to 0.5 nM. In embodiments, the scFv binds the ROR2 protein with a $K_D$ from 0.01 nM to 0.4 nM. In embodiments, the scFv binds the ROR2 protein with a $K_D$ from 0.01 nM to 0.3 nM. In embodiments, the scFv binds the ROR2 protein with a $K_D$ from 0.01 nM to 0.2 nM. In embodiments, the scFv binds the ROR2 protein with a $K_D$ from 0.01 nM to 0.1 nM.

In embodiments, the scFv binds the ROR2 protein with a a $K_D$ of 0.01, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 nM.

In embodiments, the scFv binds the ROR2 protein with a $K_D$ of about 0.07 nM. In embodiments, the scFv is 6E6 scFv and binds a ROR2 protein with a $K_D$ of 0.01 nM to 10 nM. In embodiments, the 6E6 scFv binds a ROR2 protein with a $K_D$ of 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 nM. In embodiments, the scFv is 6E6 scFv and binds a ROR2 protein with a $K_D$ of 0.07 nM.

In one embodiment, the scFv includes from the N-terminus to the C-terminus: a leader peptide of SEQ ID NO:81, a light chain variable domain of SEQ ID NO:4, a linker domain of SEQ ID NO:82, a heavy chain variable domain of SEQ ID NO:2, a spacer of SEQ ID NO:83, and a constant heavy chain domain (CH2-CH3) of SEQ ID NO:84. In one further embodiment, the scFv is the 6E6 scFv.

In embodiments, the scFv includes the sequence of SEQ ID NO:86. In embodiments, the scFv is the sequence of SEQ ID NO:86.

In embodiments, the scFv binds the ROR2 protein with a $K_D$ from 0.01 nM to 150 nM. In embodiments, the scFv binds the ROR2 protein with a $K_D$ from 1 nM to 150 nM. In embodiments, the scFv binds the ROR2 protein with a $K_D$ from 10 nM to 150 nM. In embodiments, the scFv binds the ROR2 protein with a $K_D$ from 20 nM to 150 nM. In embodiments, the scFv binds the ROR2 protein with a $K_D$ from 30 nM to 150 nM. In embodiments, the scFv binds the ROR2 protein with a $K_D$ from 40 nM to 150 nM. In embodiments, the scFv binds the ROR2 protein with a $K_D$ from 50 nM to 150 nM. In embodiments, the scFv binds the ROR2 protein with a $K_D$ from 60 nM to 150 nM. In embodiments, the scFv binds the ROR2 protein with a $K_D$ from 70 nM to 150 nM. In embodiments, the scFv binds the ROR2 protein with a $K_D$ from 80 nM to 150 nM. In embodiments, the scFv binds the ROR2 protein with a $K_D$ from 90 nM to 150 nM. In embodiments, the scFv binds the ROR2 protein with a $K_D$ from 100 nM to 150 nM. In embodiments, the scFv binds the ROR2 protein with a $K_D$ from 110 nM to 150 nM. In embodiments, the scFv binds the ROR2 protein with a $K_D$ from 120 nM to 150 nM. In embodiments, the scFv binds the ROR2 protein with a $K_D$ from 130 nM to 150 nM. In embodiments, the scFv binds the ROR2 protein with a $K_D$ from 140 nM to 150 nM.

In embodiments, the scFv binds the ROR2 protein with a $K_D$ from 0.01 nM to 140 nM. In embodiments, the scFv binds the ROR2 protein with a $K_D$ from 1 nM to 140 nM. In embodiments, the scFv binds the ROR2 protein with a $K_D$ from 10 nM to 140 nM. In embodiments, the scFv binds the ROR2 protein with a $K_D$ from 10 nM to 130 nM. In embodiments, the scFv binds the ROR2 protein with a $K_D$ from 10 nM to 120 nM. In embodiments, the scFv binds the ROR2 protein with a $K_D$ from 10 nM to 110 nM. In embodiments, the scFv binds the ROR2 protein with a $K_D$ from 10 nM to 100 nM. In embodiments, the scFv binds the ROR2 protein with a $K_D$ from 10 nM to 90 nM. In embodiments, the scFv binds the ROR2 protein with a $K_D$ from 10 nM to 80 nM. In embodiments, the scFv binds the ROR2 protein with a $K_D$ from 10 nM to 70 nM. In embodiments, the scFv binds the ROR2 protein with a $K_D$ from 10 nM to 60 nM. In embodiments, the scFv binds the ROR2 protein with a $K_D$ from 10 nM to 50 nM. In embodiments, the scFv binds the ROR2 protein with a $K_D$ from 10 nM to 40 nM. In embodiments, the scFv binds the ROR2 protein with a $K_D$ from 10 nM to 30 nM. In embodiments, the scFv binds the ROR2 protein with a $K_D$ from 10 nM to 20 nM. In embodiments, the scFv binds the ROR2 protein with a a $K_D$ of 10, 20, 30, 40, 50, 60, 70, 80, 90, 100, 110, 120, 130, 140 or 150 nM.

In embodiments, the scFv is 4G9 scFv and binds a ROR2 protein with a $K_D$ of 0.01, 1, 10, 20, 30, 40, 50, 60, 70, 80, 90, 100, 110, 120, 130, 140 or 150 nM.

In one embodiment, the scFv includes from the N-terminus to the C-terminus: a leader peptide of SEQ ID NO:81: a light chain variable domain of SEQ ID NO:8, a linker domain of SEQ ID NO:82, a heavy chain variable domain of SEQ ID NO:6, a spacer of SEQ ID NO:83, and and a constant heavy chain domain (CH2-CH3) of SEQ ID NO:84. In one further embodiment, the scFv is 4G9 scFv.

In embodiments, the scFv is capable of binding a ROR2 protein. In embodiments, the the ROR2 protein is a human ROR2 protein. In embodiments, the scFv binds a ROR2 protein. In embodiments, the ROR2 protein includes the amino acid sequence of SEQ ID NO:18. In embodiments, the scFv is capable of binding an extracellular domain of the ROR2 protein. In embodiments, the scFv binds an extracellular domain of the ROR2 protein. In embodiments, the extracellular domain includes the amino acid sequence of SEQ ID NO:22. In embodiments, the extracellular domain is a Kringle domain. In embodiments the Kringle domain includes the amino acid sequence of SEQ ID NO:113. In embodiments, the extracellular domain is an Ig-like domain. In embodiments the Ig-like domain includes the amino acid sequence of SEQ ID NO:114.

In embodiments, the scFv does not bind a mouse ROR2 protein. In embodiments, the scFv does not bind a mouse ROR2 protein identified by the UniProt reference number Q9Z138. In embodiments, the scFv provided herein does not bind a protein comprising the amino acid sequence of SEQ ID NO:20. In embodiments, the scFv provided herein does not bind a protein comprising the amino acid sequence of SEQ ID NO:24. In embodiments, the scFv provided herein does not bind the protein of SEQ ID NO:20 or SEQ ID NO:24. In embodiments, the scFv provided herein does not bind the protein of SEQ ID NO:20. In embodiments, the scFv provided herein does not bind the protein of SEQ ID NO:24

In another aspect an anti-ROR2 antibody is provided. The anti-ROR2 antibody binds the same epitope as an anti-ROR2 antibody including a heavy chain variable domain including: a CDR H1 as set forth in SEQ ID NO:25, a CDR H2 as set forth in SEQ ID NO:26 and a CDR H3 as set forth in SEQ ID NO:27; and a light chain variable domain including: a CDR L1 as set forth in SEQ ID NO:28, a CDR L2 as set forth in SEQ ID NO:29, and a CDR L3 as set forth in SEQ ID NO:30. In embodiments, the heavy chain variable domain includes the sequence of SEQ ID NO:2. In embodiments, the light chain variable domain includes the sequence of SEQ ID NO:4.

In an aspect is provided an anti-ROR2 antibody. The anti-ROR2 antibody binds the same epitope as an anti-ROR2 antibody including a heavy chain variable domain of SEQ ID:2; and a light chain variable domain of SEQ ID NO:4.

In an aspect is provided an anti-ROR2 antibody. The anti-ROR2 antibody binds the same epitope as an anti-ROR2 antibody including a heavy chain variable domain encoded by the nucleic acid sequence of SEQ ID:1; and a light chain variable domain encoded by the nucleic acid sequence of SEQ ID:3.

In an aspect is provided an anti-ROR2 antibody. The anti-ROR2 antibody binds the same epitope as an anti-ROR2 antibody including a heavy chain variable domain including: a CDR H1 as set forth in SEQ ID NO:31, a CDR H2 as set forth in SEQ ID NO:32 and a CDR H3 as set forth in SEQ ID NO:33; and a light chain variable domain including: a CDR L1 as set forth in SEQ ID NO:34, a CDR L2 as set forth in SEQ ID NO:35, and a CDR L3 as set forth in SEQ ID NO:36. In embodiments, the heavy chain variable domain includes the sequence of SEQ ID:6. In embodiments, the light chain variable domain includes the sequence of SEQ ID NO:8.

In an aspect an anti-ROR2 antibody is provided. The anti-ROR2 antibody binds the same epitope as an anti-ROR2 antibody including a heavy chain variable domain of SEQ ID:6; and a light chain variable domain of SEQ ID NO:8.

In an aspect an anti-ROR2 antibody is provided. The anti-ROR2 antibody binds the same epitope as an anti-ROR2 antibody including a heavy chain variable domain encoded by the nucleic acid sequence of SEQ ID:5; and a light chain variable domain encoded by the nucleic acid sequence of SEQ ID:7.

In an aspect is provided an anti-ROR2 antibody. The anti-ROR2 antibody binds the same epitope as an anti-ROR2 antibody including a heavy chain variable domain of SEQ ID:10; and a light chain variable domain of SEQ ID NO:12.

In an aspect is provided an anti-ROR2 antibody. The anti-ROR2 antibody binds the same epitope as an anti-ROR2 antibody including a heavy chain variable domain encoded by the nucleic acid sequence of SEQ ID:9; and a light chain variable domain encoded by the nucleic acid sequence of SEQ ID:11.

In an aspect is provided an anti-ROR2 antibody. The anti-ROR2 antibody binds the same epitope as an anti-ROR2 antibody including a heavy chain variable domain including: a CDR H1 as set forth in SEQ ID NO:43, a CDR H2 as set forth in SEQ ID NO:44 and a CDR H3 as set forth in SEQ ID NO:45; and a light chain variable domain including: a CDR L1 as set forth in SEQ ID NO:46, a CDR L2 as set forth in SEQ ID NO:47, and a CDR L3 as set forth in SEQ ID NO:48. In embodiments, the heavy chain variable domain includes the sequence of SEQ ID:14. In embodiments, the light chain variable domain includes the sequence of SEQ ID NO:16.

In an aspect is provided an anti-ROR2 antibody. The anti-ROR2 antibody binds the same epitope as an anti- ROR2 antibody including a heavy chain variable domain of SEQ ID:14; and a light chain variable domain of SEQ ID NO:16.

In an aspect is provided an anti-ROR2 antibody. The anti-ROR2 antibody binds the same epitope as an anti-ROR2 antibody including a heavy chain variable domain encoded by the nucleic acid sequence of SEQ ID:13; and a light chain variable domain encoded by the nucleic acid sequence of SEQ ID:15.

In embodiments, the antibody is capable of binding a ROR2 protein. In embodiments, the the ROR2 protein is a human ROR2 protein. In embodiments, the antibody binds a ROR2 protein. In embodiments, the ROR2 protein includes the amino acid sequence of SEQ ID NO:18. In embodiments, the antibody is capable of binding an extracellular domain of the ROR2 protein. In embodiments, the antibody binds an extracellular domain of the ROR2 protein. In embodiments, the extracellular domain includes the amino acid sequence of SEQ ID NO:22. In embodiments, the extracellular domain is a Kringle domain. In embodiments the Kringle domain includes the amino acid sequence of SEQ ID NO:113. In embodiments, the extracellular domain is an Ig-like domain. In embodiments, the Ig-like domain includes includes the amino acid sequence of SEQ ID NO:114.

In embodiments, the ROR2 protein includes a histidine at a position corresponding to position 349, an aspartic acid at a position corresponding to position 354, or a methionine at a position corresponding to position 386 of SEQ ID NO:22. In embodiments, the ROR2 protein includes a histidine at a position corresponding to position 349, an aspartic acid at a position corresponding to position 354, and a methionine at a position corresponding to position 386 of SEQ ID NO:22. In embodiments, the ROR2 protein includes a histidine at a position corresponding to position 349, an aspartic acid at a position corresponding to position 354, or a methionine at a position corresponding to position 386 of SEQ ID NO:18. In embodiments, the ROR2 protein includes a histidine at a position corresponding to position 349, an aspartic acid at a position corresponding to position 354, and a methionine at a position corresponding to position 386 of SEQ ID NO:18.

In embodiments, the ROR2 protein includes a methionine at a position corresponding to position 386 of SEQ ID NO:22. In embodiments, the ROR2 protein includes a histidine at a position corresponding to position 349 of SEQ ID NO:22. In embodiments, the ROR2 protein includes an aspartic acid at a position corresponding to position 354 of SEQ ID NO:22. In embodiments, the ROR2 protein includes a methionine at a position corresponding to position 386 of SEQ ID NO:18. In embodiments, the ROR2 protein includes a histidine at a position corresponding to position 349 of SEQ ID NO:18. In embodiments, the ROR2 protein includes an aspartic acid at a position corresponding to position 354 of SEQ ID NO:18.

In embodiments, the antibody is capable of binding a ROR2 protein. In embodiments, the the ROR2 protein is a human ROR2 protein. In embodiments, the antibody binds a ROR2 protein. In embodiments, the ROR2 protein includes the amino acid sequence of SEQ ID NO:18. In embodiments, the antibody is capable of binding an extracellular domain of the ROR2 protein. In embodiments, the antibody binds an extracellular domain of the ROR2 protein. In embodiments, the extracellular domain includes the amino acid sequence of SEQ ID NO:22. In embodiments, the extracellular domain is an Ig-like domain. In embodiments, the Ig-like domain includes residues corresponding to positions 79 to 147 of SEQ ID NO:22.

In embodiments, the antibody is attached to a therapeutic agent. In embodiments, the antibody is attached to a diagnostic agent. In embodiments, the diagnostic agent is a detectable moiety.

In embodiments, the antibody binds the ROR2 protein with a $K_D$ from 0.01 nM to 150 nM. In embodiments, the antibody binds the ROR2 protein with a $K_D$ from 1 nM to 150 nM. In embodiments, the antibody binds the ROR2 protein with a $K_D$ from 10 nM to 150 nM. In embodiments, the antibody binds the ROR2 protein with a $K_D$ from 20 nM to 150 nM. In embodiments, the antibody binds the ROR2 protein with a $K_D$ from 30 nM to 150 nM. In embodiments, the antibody binds the ROR2 protein with a $K_D$ from 40 nM to 150 nM. In embodiments, the antibody binds the ROR2 protein with a $K_D$ from 50 nM to 150 nM. In embodiments, the antibody binds the ROR2 protein with a $K_D$ from 60 nM to 150 nM. In embodiments, the antibody binds the ROR2 protein with a $K_D$ from 70 nM to 150 nM. In embodiments, the antibody binds the ROR2 protein with a $K_D$ from 80 nM to 150 nM. In embodiments, the antibody binds the ROR2 protein with a $K_D$ from 90 nM to 150 nM. In embodiments, the antibody binds the ROR2 protein with a $K_D$ from 100 nM to 150 nM. In embodiments, the antibody binds the ROR2 protein with a $K_D$ from 110 nM to 150 nM. In embodiments, the antibody binds the ROR2 protein with a $K_D$ from 120 nM to 150 nM. In embodiments, the antibody binds the ROR2 protein with a $K_D$ from 130 nM to 150 nM. In embodiments, the antibody binds the ROR2 protein with a $K_D$ from 140 nM to 150 nM.

In embodiments, the antibody binds the ROR2 protein with a $K_D$ from 0.01 nM to 140) nM. In embodiments, the antibody binds the ROR2 protein with a $K_D$ from 0.01 nM to 140 nM. In embodiments, the antibody binds the ROR2 protein with a $K_D$ from 0.01 nM to 130 nM. In embodiments, the antibody binds the ROR2 protein with a $K_D$ from 0.01 nM to 120 nM. In embodiments, the antibody binds the ROR2 protein with a $K_D$ from 0.01 nM to 110 nM. In embodiments, the antibody binds the ROR2 protein with a $K_D$ from 0.01 nM to 100 nM. In embodiments, the antibody binds the ROR2 protein with a $K_D$ from 0.01 nM to 90 nM. In embodiments, the antibody binds the ROR2 protein with a $K_D$ from 0.01 nM to 80 nM. In embodiments, the antibody binds the ROR2 protein with a $K_D$ from 0.01 nM to 70 nM. In embodiments, the antibody binds the ROR2 protein with a $K_D$ from 0.01 nM to 60 nM. In embodiments, the antibody binds the ROR2 protein with a $K_D$ from 0.01 nM to 50 nM. In embodiments, the antibody binds the ROR2 protein with a $K_D$ from 0.01 nM to 40 nM. In embodiments, the antibody binds the ROR2 protein with a $K_D$ from 0.01 nM to 30 nM. In embodiments, the antibody binds the ROR2 protein with a $K_D$ from 0.01 nM to 20 nM. In embodiments, the antibody binds the ROR2 protein with a $K_D$ from 10 nM to 20 nM. In embodiments, the antibody binds the ROR2 protein with a $K_D$ from 0.01 nM to 20 nM. In embodiments, the antibody binds the ROR2 protein with a a $K_D$ of 0.01, 1, 10, 20, 30, 40, 50, 60, 70, 80, 90, 100, 110, 120, 130, 140 or 150 nM.

The antibodies binding the epitopes provided herein may be humanized antibodies. Thus, in embodiments, the antibody is a humanized antibody. In embodiments, antibody is a chimeric antibody. In embodiments, antibody is a Fab' fragment. In embodiments, the antibody is an IgG. In embodiments, the antibody is an IgG. The anti-ROR2 antibody provided herein may be an IgG1, IgG2, IgG3 or IgG4. In embodiments, the antibody is an IgG1. In embodiments, the antibody is an IgG2. In embodiments, the antibody is an IgG2a. In embodiments, the antibody is an IgG3. In embodiments, the antibody is an IgG4.

In embodiments, the antibody does not bind a mouse ROR2 protein. In embodiments, the antibody does not bind a mouse ROR2 protein identified by the UniProt reference number Q9Z138. In embodiments, the antibody provided herein does not bind a protein comprising the amino acid sequence of SEQ ID NO:20. In embodiments, the antibody provided herein does not bind a protein comprising the amino acid sequence of SEQ ID NO:24. In embodiments, the antibody provided herein does not bind the protein of SEQ ID NO:20 or SEQ ID NO:24. In embodiments, the antibody provided herein does not bind the protein of SEQ ID NO:20. In embodiments, the antibody provided herein does not bind the protein of SEQ ID NO:24.

In embodiments, the antibody does not bind an arginine at a position corresponding to position 349 of SEQ ID NO:20. In embodiments, the antibody does not bind a glutamic acid at a position corresponding to position 354 of SEQ ID NO:20. In embodiments, the antibody does not bind a valine at a position corresponding to position 386 of SEQ ID NO:20. In embodiments, the antibody does not bind an arginine at a position corresponding to position 349 of SEQ ID NO:24. In embodiments, the antibody does not bind a glutamic acid at a position corresponding to position 354 of SEQ ID NO:24. In embodiments, the antibody does not bind a valine at a position corresponding to position 386 of SEQ ID NO:24.

In embodiments, the antibody provided herein does not bind a ROR2-negative cell. A "ROR2-negative cell" as provided herein is a cell that does not express a detectable amount of a ROR2 protein relative to a standard control. In embodiments, the expression level of a ROR2-negative cell is undetectable using methods conventionally known in the art to a detect protein expression in a cell (e.g., immunofluorescent detection, protein biochemistry, RNA expression level). In embodiments, the expression level of a ROR2-negative cell is 1000, 500, 100, 50, 25, 20, 10, 5, or 1.5 times lower than the expression level of a standard control (e.g., a cell expressing detectable levels of ROR2 using conventional methods). No limiting examples of ROR2-negative cells include a peripheral blood mononuclear cell (PBMC) from a healthy subject.

Chimeric Antigen Receptor Proteins

As described above, the heavy chain variable (VH) domain and the light chain variable (VL) domain provided herein including embodiments thereof, may each independently form part of an antibody, a fragment of an antibody, or a a chimeric antigen receptor or bispecific antibody. Provided herein are, inter alia, chimeric antigen receptors and bispecific antibodies, which include the light chain variable (VL) domain and/or the heavy chain variable (VH) domain as provided herein and are therefore capable of binding human ROR2 effectively and efficiently. The antibody region of the chimeric antigen receptor may include any of the light chain and heavy chain variable domains provided herein including embodiments thereof. The light chain variable (VL) domain and/or the heavy chain variable (VH) domain as provided herein may form part of a chimeric antigen receptor. Thus, in an aspect is provided a chimeric antigen receptor including: (i) an antibody region including: (a) a light chain variable domain including a CDR L1 as set forth in SEQ ID NO:28, a CDR L2 as set forth in SEQ ID NO:29 and a CDR L3 as set forth in SEQ ID NO:30; and (b) a heavy chain variable region domain including a CDR H1 as set forth in SEQ ID NO:25, a CDR H2 as set forth in SEQ ID NO:26, and a CDR H3 as set forth in SEQ ID NO:27; and (ii) a transmembrane domain. In one embodiment, the chimeric antigen receptor includes the light chain variable domain of antibody 6E6 and a heavy chain variable domain of antibody 6E6.

In another aspect is provided a chimeric antigen receptor including: (i) an antibody region including: (a) a light chain variable domain including a CDR L1 as set forth in SEQ ID NO:34, a CDR L2 as set forth in SEQ ID NO:35 and a CDR L3 as set forth in SEQ ID NO:36; and (b) a heavy chain variable region domain including a CDR H1 as set forth in SEQ ID NO:31, a CDR H2 as set forth in SEQ ID NO:32, and a CDR H3 as set forth in SEQ ID NO:33; and (ii) a transmembrane domain. In one embodiment, the chimeric antigen receptor includes the light chain variable domain of antibody 4G9 and a heavy chain variable domain of antibody 4G9.

In another aspect is provided a chimeric antigen receptor including: (i) an antibody region including: (a) a light chain variable domain including a CDR L1 as set forth in SEQ ID NO:40, a CDR L2 as set forth in SEQ ID NO:41 and a CDR L3 as set forth in SEQ ID NO:42; and (b) a heavy chain variable region domain including a CDR H1 as set forth in SEQ ID NO:37, a CDR H2 as set forth in SEQ ID NO:38, and a CDR H3 as set forth in SEQ ID NO:39; and (ii) a transmembrane domain. In one embodiment, the chimeric antigen receptor includes the light chain variable domain of antibody 5C11 and a heavy chain variable domain of antibody 5C11.

In an aspect is provided a chimeric antigen receptor including: (i) an antibody region including: (a) a light chain variable domain including a CDR L1 as set forth in SEQ ID NO:46, a CDR L2 as set forth in SEQ ID NO:47 and a CDR L3 as set forth in SEQ ID NO:48; and (b) a heavy chain variable region domain including a CDR H1 as set forth in SEQ ID NO:43, a CDR H2 as set forth in SEQ ID NO:44, and a CDR H3 as set forth in SEQ ID NO:45; and (ii) a transmembrane domain. In one embodiment, the chimeric antigen receptor includes the light chain variable domain of antibody 5G3 and a heavy chain variable domain of antibody 5G3.

An "antibody region" as provided herein refers to a monovalent or multivalent protein moiety that forms part of the recombinant protein (e.g., CAR, bispecific antibody) provided herein including embodiments thereof. A person of ordinary skill in the art will therefore immediately recognize that the antibody region is a protein moiety capable of binding an antigen (epitope). Thus, the antibody region provided herein may include a domain of an antibody (e.g., a light chain variable (VL) domain, a heavy chain variable (VH) domain) or a fragment of an antibody (e.g., Fab). In embodiments, the antibody region is a protein conjugate. A "protein conjugate" as provided herein refers to a construct consisting of more than one polypeptide, wherein the polypeptides are bound together covalently or non-covalently. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker. In embodiments, the antibody region is an scFv. The antibody region may include a light chain variable (VL) domain and/or a heavy chain variable (VH) domain. In embodiments, the antibody region includes a light chain variable (VL) domain. In embodiments, the antibody region includes a heavy chain variable (VH) domain.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. Non-limiting examples of transmembrane domains include the transmembrane domains of CD28, CD8, CD4 or CD3-zeta. In embodiments, the transmembrane domain is a CD4 transmembrane domain.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments. CD28 is the protein as identified by the NCBI sequence reference GI:340545506, homolog or functional fragment thereof.

In embodiments, the transmembrane domain is a CD8 transmembrane domain. The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, CD8 is the protein as identified by the NCBI sequence reference GI:225007534, homolog or functional fragment thereof.

In embodiments, the transmembrane domain is a CD4 transmembrane domain. The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by the NCBI sequence reference GI:303522473, homolog or functional fragment thereof.

In embodiments, the transmembrane domain is a CD3-zeta (also known as CD247) transmembrane domain. The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, CD3-zeta is the protein as identified by the NCBI sequence reference GI:166362721, homolog or functional fragment thereof.

In embodiments, the chimeric antigen receptor further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by said T cell of proteins known in the art to characteristic of activated T cell (e.g., CTLA-4, PD-1, CD28, CD69). In embodiments, the intracellular T-cell signaling domain is a CD3 ζ intracellular T-cell signaling domain.

In embodiments, the chimeric antigen receptor further includes an intracellular co-stimulatory T-cell signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1 BB intracellular co-stimulatory signaling domain, an ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is an ICOS intracellular co-stimulatory signaling domain. In embodiments, the intracellular co-stimulatory signaling domain is an OX-40 intracellular co-stimulatory signaling domain.

In embodiments, the antibody region includes an Fc domain. In embodiments, the antibody region includes a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the spacer region includes an Fc region. In embodiments, the spacer region is an Fc region. Examples of spacer regions contemplated for the compositions provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a hinge region.

The term "CTLA-4" as referred to herein includes any of the recombinant or naturally-occurring forms of the cytotoxic T-lymphocyte-associated protein 4 protein, also known as CD152 (cluster of differentiation 152), or variants or homologs thereof that maintain CTLA-4 activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 protein. In embodiments, the CTLA-4 protein is substantially identical to the protein identified by the UniProt reference number P16410 or a variant or homolog having substantial identity thereto.

The term "CD28" as referred to herein includes any of the recombinant or naturally-occurring forms of the Cluster of Differentiation 28 protein, or variants or homologs thereof that maintain CD28 activity (e.g. within at least 50%, 80%, 90%, 95%, 96%, 97%, 98%, 99% or 100% activity compared to CD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 protein. In embodiments, the CD28 protein is substantially identical to the protein identified by the UniProt reference number P10747 or a variant or homolog having substantial identity thereto.

The term "CD69" as referred to herein includes any of the recombinant or naturally-occurring forms of the Cluster of Differentiation 69 protein, or variants or homologs thereof that maintain CD69 activity (e.g. within at least 50%, 80%, 90%, 95%, 96%, 97%, 98%, 99% or 100% activity compared to CD69). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD69 protein. In embodiments, the CD69 protein is substantially identical to the protein identified by the UniProt reference number Q07108 or a variant or homolog having substantial identity thereto.

The term "4-1BB" as referred to herein includes any of the recombinant or naturally-occurring forms of the 4-1BB protein, also known as tumor necrosis factor receptor superfamily member 9 (TNFRSF9), Cluster of Differentiation 137 (CD137) and induced by lymphocyte activation (ILA), or variants or homologs thereof that maintain 4-1BB activity (e.g. within at least 50%, 80%, 90%, 95%, 96%, 97%, 98%, 99% or 100% activity compared to 4-1BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the 4-1BB protein is substantially identical to the protein identified by the UniProt reference number Q07011 or a variant or homolog having substantial identity thereto.

The chimeric antigen receptors provided herein may include any of the anti-ROR2 antibodies or fragments thereof described herein. Thus, the chimeric antigen receptors may include any of the CDRs, FRs, heavy chain variable domains, or light chain variable domains provided herein.

For example, the heavy chain variable domain may include the sequence of SEQ ID NO:2, SEQ ID NO:6, SEQ ID NO:10 or SEQ ID NO:14. In embodiments, the heavy chain variable domain is the sequence of SEQ ID NO:2, SEQ ID NO:6, SEQ ID NO:10 or SEQ ID NO:14. For example, the light chain variable domain may include the sequence of SEQ ID NO:4, SEQ ID NO:8, SEQ ID NO:12, or SEQ ID NO:16. In embodiments, light chain variable domain is the sequence of SEQ ID NO:4, SEQ ID NO:8, SEQ ID NO:12, or SEQ ID NO:16.

In embodiments, the chimeric antigen receptor further includes a heavy chain constant domain. In embodiments, the chimeric antigen receptor further includes a spacer region. In embodiments, the spacer region is between the transmembrane domain and the antibody region. In embodiments, the spacer region further includes a hinge region. In embodiments, the spacer region includes the sequence of SEQ ID NO:94. In embodiments, the spacer region includes the sequence of SEQ ID NO:95. In embodiments, the spacer region includes the sequence of SEQ ID NO:96.

In embodiments, the chimeric antigen receptor further includes a linker domain. In embodiments, the linker domain is between the heavy chain variable domain and the light chain variable domain. In embodiments, the linker domain includes the sequence of SEQ ID NO:82. In embodiments, the chimeric antigen receptor further includes a leader peptide. In embodiments, the leader peptide includes the sequence of SEQ ID NO:93.

In embodiments, the chimeric antigen receptor includes the sequence of SEQ ID NO:100. In embodiments, the chimeric antigen receptor is the sequence of SEQ ID NO:100. In embodiments, the chimeric antigen receptor includes the sequence of SEQ ID NO:101. In embodiments, the chimeric antigen receptor is the sequence of SEQ ID NO:101.

In one embodiment, the chimeric antigen receptor includes from the N-terminus to the C-terminus: a leader peptide of SEQ ID NO:93, a light chain variable domain of SEQ ID NO:4, a linker domain of SEQ ID NO:82, a heavy chain variable domain of SEQ ID NO:2, a spacer domain of SEQ ID NO:96, a transmembrane domain of SEQ ID NO:97, an intracellular co-stimulatory signaling domain of SEQ ID NO:98, and an intracellular T-cell signaling domain of SEQ ID NO:99.

In one embodiment, the protein includes from the N-terminus to the C-terminus: a leader peptide of SEQ ID NO:93, a light chain variable domain of SEQ ID NO:8, a linker domain of SEQ ID NO:82, a heavy chain variable domain of SEQ ID NO:6, a spacer domain of SEQ ID NO:96, a transmembrane domain of SEQ ID NO:97, an intracellular co-stimulatory signaling domain of SEQ ID NO:98, and an intracellular T-cell signaling domain of SEQ ID NO:99.

Bispecific Antibodies

The light chain variable (VL) domain and the heavy chain variable (VH) domain as provided herein may form part of a bispecific antibody. Thus, the second antibody region may include any of the light chain and/or heavy chain variable domains provided herein including embodiments thereof.

Thus, in another aspect is provided a bispecific antibody including: (i) a first antibody region capable of binding an effector cell ligand; and (ii) a second antibody region, including: (a) a heavy chain variable domain including a CDR H1 as set forth in SEQ ID NO:25, a CDR H2 as set forth in SEQ ID NO:26 and a CDR H3 as set forth in SEQ ID NO:27; and (b) a CDR L1 as set forth in SEQ ID NO:28, a CDR L2 as set forth in SEQ ID NO:29, and a CDR L3 as set forth in SEQ ID NO:30.

In another aspect is provided a bispecific antibody including: (i) a first antibody region capable of binding an effector cell ligand; and (ii) a second antibody region, including: (a) a heavy chain variable domain including a CDR H1 as set forth in SEQ ID NO:31, a CDR H2 as set forth in SEQ ID NO:32 and a CDR H3 as set forth in SEQ ID NO:33; and (b) a a CDR L1 as set forth in SEQ ID NO:34, a CDR L2 as set forth in SEQ ID NO:35, and a CDR L3 as set forth in SEQ ID NO:36.

In another aspect is provided a bispecific antibody including: (i) a first antibody region capable of binding an effector cell ligand; and (ii) a second antibody region, including: (a) a heavy chain variable domain including a CDR H1 as set forth in SEQ ID NO:37, a CDR H2 as set forth in SEQ ID NO:38 and a CDR H3 as set forth in SEQ ID NO:39; and (b) a CDR L1 as set forth in SEQ ID NO:40, a CDR L2 as set forth in SEQ ID NO:41, and a CDR L3 as set forth in SEQ ID NO:42.

In another aspect is provided a bispecific antibody including: (i) a first antibody region capable of binding an effector cell ligand; and (ii) a second antibody region, including: (a) a heavy chain variable domain including a CDR H1 as set forth in SEQ ID NO:43, a CDR H2 as set forth in SEQ ID NO:44 and a CDR H3 as set forth in SEQ ID NO:45; and (b) a CDR L1 as set forth in SEQ ID NO:46, a CDR L2 as set forth in SEQ ID NO:47, and a CDR L3 as set forth in SEQ ID NO:48.

The term "effector cell ligand" as provided herein refers to a cell surface molecule expressed on an effector cell of the immune system (e.g., a cytotoxic T cell, a helper T cell, a B cell, a natural killer cell). Upon binding of the first antibody region to the effector cell ligand expressed on the effector cell, the effector cell is activated and able to exert its function (e.g., selective killing or eradication of malignant, infected or otherwise unhealthy cells). In embodiments, the effector cell ligand is a CD3 protein. In embodiments, the effector cell ligand is a CD16 protein. In embodiments, the effector cell ligand is a CD32 protein. In embodiments, the effector cell ligand is a NKp46 protein. The first antibody region as provided herein may be an antibody, an antibody variant, a fragment of an antibody or a fragment of an antibody variant.

A "CD3 protein" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex.

A "CD16 protein" as referred to herein includes any of the recombinant or naturally-occurring forms of the Cluster of Differentiation 16 (CD16) protein, also known as low affinity immunoglobulin gamma Fc region receptor III-A, or variants or homologs thereof that maintain CD16 activity (e.g. within at least 50%, 80%, 90%, 95%, 96%, 97%, 98%, 99% or 100% activity compared to CD16). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD16 protein. In embodiments, the CD16 protein is substantially identical to the protein identified by the UniProt reference number P08637 or a variant or homolog having substantial identity thereto.

A "CD32 protein" as referred to herein includes any of the recombinant or naturally-occurring forms of the Cluster of Differentiation 32 (CD32) protein, also known as low affinity immunoglobulin gamma Fc region receptor II-A, or variants or homologs thereof that maintain CD32 activity (e.g. within at least 50%, 80%, 90%, 95%, 96%, 97%, 98%, 99% or 100% activity compared to CD32). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD32 protein. In embodiments, the CD32 protein is substantially identical to the protein identified by the UniProt reference number P12318 or a variant or homolog having substantial identity thereto.

A "NKp46 protein" as referred to herein includes any of the recombinant or naturally-occurring forms of the NKp46 protein, also known as natural cytotoxicity triggering receptor 1, or variants or homologs thereof that maintain NKp46 activity (e.g. within at least 50%, 80%, 90%, 95%, 96%, 97%, 98%, 99% or 100% activity compared to NKp46). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NKp46 protein. In embodiments, the NKp46 protein is substantially identical to the protein identified by the UniProt reference number O76036 or a variant or homolog having substantial identity thereto.

The bispecific antibody provided herein may include any of the ROR2 antibodies or fragments thereof described herein. Thus, the second antibody region may include any of the CDRs, FRs, heavy chain variable domains, or light chain variable domains provided herein. In embodiments, the second antibody region includes a heavy chain variable domain including the sequence of SEQ ID NO:2. In embodiments, the second antibody region includes a light chain variable domain includes the sequence of SEQ ID NO:4. In embodiments, the second antibody region includes a heavy chain variable domain with the sequence of SEQ ID NO:2. In embodiments, the second antibody region includes a light chain variable domain with the sequence of SEQ ID NO:4.

Thus, the heavy chain variable domain of the second antibody region may include, for example, a FR H1 as set forth in SEQ ID NO:49, a FR H2 as set forth in SEQ ID NO:50, a FR H3 as set forth in SEQ ID NO:51, and a FR H4 as set forth in SEQ ID NO:52. The light chain variable domain of the second antibody region a may include any of the CDRs or FRs provided herein. For example, the light chain variable domain may include, for example, a FR L1 as set forth in SEQ ID NO:53, a FR L2 as set forth in SEQ ID NO:54, a FR L3 as set forth in SEQ ID NO:55, and a FR L4 as set forth in SEQ ID NO:56.

In embodiments, the second antibody region includes a heavy chain variable domain including the sequence of SEQ ID NO:6. In embodiments, the second antibody region includes a light chain variable domain includes the sequence of SEQ ID NO:8. In embodiments, the second antibody region includes a heavy chain variable domain with the sequence of SEQ ID NO:6. In embodiments, the second antibody region includes a light chain variable domain with the sequence of SEQ ID NO:8.

The heavy chain variable domain of the second antibody region may include, for example, a FR H1 as set forth in SEQ ID NO:57, a FR H2 as set forth in SEQ ID NO:58, a FR H3 as set forth in SEQ ID NO:59, and a FR H4 as set forth in SEQ ID NO:60. The light chain variable domain of the bispecific antibody provided herein may include, for example, a FR L1 as set forth in SEQ ID NO:61, a FR L2 as set forth in SEQ ID NO:62, a FR L3 as set forth in SEQ ID NO:63, and a FR L4 as set forth in SEQ ID NO:64.

In embodiments, the second antibody region includes a heavy chain variable domain including the sequence of SEQ ID NO:10. In embodiments, the second antibody region includes a light chain variable domain includes the sequence of SEQ ID NO:12. In embodiments, the second antibody region includes a heavy chain variable domain with the sequence of SEQ ID NO:10. In embodiments, the second antibody region includes a light chain variable domain with the sequence of SEQ ID NO:12.

The heavy chain variable domain of the second antibody region may include, for example, a FR H1 as set forth in SEQ ID NO:65, a FR H2 as set forth in SEQ ID NO:66, a FR H3 as set forth in SEQ ID NO:67, and a FR H4 as set forth in SEQ ID NO:68. The light chain variable domain of the bispecific antibody provided herein may include, for example, a FR L1 as set forth in SEQ ID NO:69, a FR L2 as set forth in SEQ ID NO:70, a FR L3 as set forth in SEQ ID NO:71, and a FR L4 as set forth in SEQ ID NO:72.

In embodiments, the second antibody region includes a heavy chain variable domain including the sequence of SEQ ID NO:14. In embodiments, the second antibody region includes a light chain variable domain includes the sequence of SEQ ID NO:16. In embodiments, the second antibody region includes a heavy chain variable domain with the sequence of SEQ ID NO:14. In embodiments, the second antibody region includes a light chain variable domain with the sequence of SEQ ID NO:16.

The heavy chain variable domain of the second antibody region may include, for example, a FR H1 as set forth in SEQ ID NO:73, a FR H2 as set forth in SEQ ID NO:74, a FR H3 as set forth in SEQ ID NO:75, and a FR H4 as set forth in SEQ ID NO:76. The light chain variable domain of the bispecific antibody provided herein may include, for example, a FR L1 as set forth in SEQ ID NO:77, a FR L2 as set forth in SEQ ID NO:78, a FR L3 as set forth in SEQ ID NO:79, and a FR L4 as set forth in SEQ ID NO:80.

In embodiments, the first antibody region is a first Fab' fragment or the second antibody region is a second Fab' fragment. In embodiments, the first antibody region is a single chain variable fragment (scFv) or the second antibody region is a second single chain variable fragment (scFv).

In embodiments, the scFv of the second antibody region binds the ROR2 protein with a $K_D$ from 0.01 nM to 150 nM. In embodiments, the scFv of the second antibody region binds the ROR2 protein with a $K_D$ from 0.1 nM to 150 nM. In embodiments, the scFv of the second antibody region binds the ROR2 protein with a $K_D$ from 1 nM to 150 nM. In embodiments, the scFv of the second antibody region binds the ROR2 protein with a $K_D$ from 10 nM to 150 nM. In embodiments, the scFv of the second antibody region binds the ROR2 protein with a $K_D$ from 20) nM to 150 nM. In embodiments, the scFv of the second antibody region binds the ROR2 protein with a $K_D$ from 30 nM to 150 nM. In embodiments, the scFv of the second antibody region binds the ROR2 protein with a $K_D$ from 40 nM to 150 nM. In embodiments, the scFv of the second antibody region binds the ROR2 protein with a $K_D$ from 50 nM to 150 nM. In embodiments, the scFv of the second antibody region binds the ROR2 protein with a $K_D$ from 60 nM to 150 nM. In embodiments, the scFv of the second antibody region binds the ROR2 protein with a $K_D$ from 70 nM to 150 nM. In embodiments, the scFv of the second antibody region binds the ROR2 protein with a $K_D$ from 80 nM to 150 nM. In embodiments, the scFv of the second antibody region binds the ROR2 protein with a $K_D$ from 90 nM to 150 nM. In embodiments, the scFv of the second antibody region binds the ROR2 protein with a $K_D$ from 100 nM to 150 nM. In embodiments, the scFv of the second antibody region binds the ROR2 protein with a $K_D$ from 110 nM to 150 nM. In embodiments, the scFv of the second antibody region binds the ROR2 protein with a $K_D$ from 120 nM to 150 nM. In embodiments, the scFv of the second antibody region binds the ROR2 protein with a $K_D$ from 130 nM to 150 nM. In embodiments, the scFv of the second antibody region binds the ROR2 protein with a $K_D$ from 140 nM to 150 nM.

In embodiments, the scFv of the second antibody region binds the ROR2 protein with a $K_D$ from 0.01 nM to 140 nM. In embodiments, the scFv of the second antibody region binds the ROR2 protein with a $K_D$ from 0.01 nM to 130 nM. In embodiments, the scFv of the second antibody region binds the ROR2 protein with a $K_D$ from 0.01 nM to 120 nM. In embodiments, the scFv of the second antibody region binds the ROR2 protein with a $K_D$ from 0.01 nM to 110 nM. In embodiments, the scFv of the second antibody region binds the ROR2 protein with a $K_D$ from 0.01 nM to 100 nM. In embodiments, the scFv of the second antibody region binds the ROR2 protein with a $K_D$ from 0.01 nM to 90 nM. In embodiments, the scFv of the second antibody region binds the ROR2 protein with a $K_D$ from 0.01 nM to 80 nM. In embodiments, the scFv of the second antibody region binds the ROR2 protein with a $K_D$ from 0.01 nM to 70 nM. In embodiments, the scFv of the second antibody region binds the ROR2 protein with a $K_D$ from 0.01 nM to 60 nM. In embodiments, the scFv of the second antibody region binds the ROR2 protein with a $K_D$ from 0.01 nM to 50 nM. In embodiments, the scFv of the second antibody region binds the ROR2 protein with a $K_D$ from 0.01 nM to 40 nM. In embodiments, the scFv of the second antibody region binds the ROR2 protein with a $K_D$ from 0.01 nM to 30 nM. In embodiments, the scFv of the second antibody region binds the ROR2 protein with a $K_D$ from 0).01 nM to 20 nM. In embodiments, the scFv of the second antibody region binds the ROR2 protein with a $K_D$ from 0.01 nM to 10 nM. In embodiments, the scFv of the second antibody region binds the ROR2 protein with a $K_D$ from 0.01 nM to 1 nM.

In embodiments, the scFv of the second antibody region binds the ROR2 protein with a $K_D$ of about 0.07 nM. In embodiments, the scFv of the second antibody region binds the ROR2 protein with a $K_D$ of 0.07 nM. In embodiments, the scFv of the second antibody region is the 6E6 scFv and binds the ROR2 protein with a $K_D$ of 0.07 nM.

The second antibody region may include a light chain variable (VL) domain or a heavy chain variable (VH) domain. In embodiments, the second antibody region includes a light chain variable (VL) domain. In embodiments, the second antibody region includes a heavy chain variable (VH) domain.

In embodiments, the second antibody region is bound to a ROR2 protein. In embodiments, the ROR2 protein is expressed on a cell. In embodiments, the cell is a cancer cell. In embodiments, the cancer cell is cancer is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell. In embodiments, the cancer cell is a breast cancer cell. In embodiments, the cancer cell is an ovarian cancer cell. In embodiments, the cancer cell is a pancreatic cancer cell. In embodiments, the cancer cell is cancer is a cervical cancer cell. In embodiments, the cancer cell is cancer is a gastric cancer cell. In embodiments, the cancer cell is cancer is a renal cancer cell. In embodiments, the cancer cell is cancer is a head and neck cancer cell. In embodiments, the cancer cell is a cancer is bone cancer cell. In embodiments, the cancer cell is cancer is a skin cancer cell. In embodiments, the cancer cell is cancer is a prostate cancer cell.

Nucleic Acid Compositions

The compositions provided herein include nucleic acid molecules encoding the anti-ROR2 antibodies, CARs and bispecific antibodies or portions thereof provided herein including embodiments thereof. The antibodies, CARs and bispecific antibodies encoded by the isolated nucleic acid are described in detail throughout this application (including the description above and in the examples section). Thus, in an aspect, an isolated nucleic acid encoding an antibody as provided herein including embodiments thereof is provided.

In embodiments, the isolated nucleic acid encodes a variable heavy chain domain or a variable light chain domain provided herein. In embodiments, the isolated nucleic acid encodes a variable heavy chain domain. In embodiments, the isolated nucleic acid encodes a variable light chain domain. In embodiments, the isolated nucleic acid includes the sequence of SEQ ID NO:1. In embodiments, the isolated nucleic acid includes the sequence of SEQ ID NO:3. In embodiments, the isolated nucleic acid includes the sequence of SEQ ID NO:5. In embodiments, the isolated nucleic acid includes the sequence of SEQ ID NO:7. In embodiments, the isolated nucleic acid includes the sequence of SEQ ID NO:9. In embodiments, the isolated nucleic acid includes the sequence of SEQ ID NO:11. In embodiments, the isolated nucleic acid includes the sequence of SEQ ID NO:13. In embodiments, the isolated nucleic acid includes the sequence of SEQ ID NO:15.

In another aspect, an isolated nucleic acid encoding an antibody as provided herein including embodiments thereof is provided. In embodiments, the isolated nucleic acid includes the sequence of SEQ ID NO:91. In embodiments, the isolated nucleic acid includes the sequence of SEQ ID NO:92.

In another aspect, an isolated nucleic acid encoding a chimeric antigen receptor as provided herein including embodiments thereof is provided. In embodiments, the isolated nucleic acid includes the sequence of SEQ ID NO:111. In embodiments, the isolated nucleic acid includes the sequence of SEQ ID NO:112.

Pharmaceutical Compositions

The compositions provided herein include pharmaceutical compositions including the anti anti-ROR2 antibodies, CARs and bispecific antibodies provided herein including embodiments thereof. Thus, in an aspect is provided a pharmaceutical composition including a therapeutically effective amount of an antibody as provided herein including embodiments thereof and a pharmaceutically acceptable excipient.

In another aspect is provided a pharmaceutical composition including a therapeutically effective amount of a CAR as provided herein including embodiments thereof and a pharmaceutically acceptable excipient.

In another aspect is provided a pharmaceutical composition including a therapeutically effective amount of a bispecific antibody as provided herein including embodiments thereof and a pharmaceutically acceptable excipient.

Methods of Treatment

The compositions (e.g., the anti-ROR2 antibodies CARs and bispecific antibodies) provided herein, including embodiments thereof, are contemplated as providing effective treatments for diseases such as cancer (e.g., breast cancer).

Thus, in an aspect is provided a method of treating cancer in a subject in need thereof, the method including administering to a subject a therapeutically effective amount of an antibody as provided herein including embodiments thereof. In another aspect is provided a method of inhibiting metastasis of a ROR2 expressing cancer in a subject in need thereof, the method including administering to a subject a therapeutically effective amount of an antibody provided herein including embodiments thereof.

In another aspect is provided a method of treating cancer in a subject in need thereof, the method including administering a therapeutically effective amount of a chimeric antigen receptor provided herein including embodiments thereof to a subject.

In embodiments, the cancer is a solid tumor malignancy. In embodiments, the cancer is breast cancer, ovarian cancer, pancreatic cancer, cervical cancer, gastric cancer, renal cancer, head and neck cancer, bone cancer, skin cancer or prostate cancer. In embodiments, the cancer is breast cancer. In embodiments, the cancer is ovarian cancer. In embodiments, the cancer is pancreatic cancer. In embodiments, the cancer is cervical cancer. In embodiments, the cancer is gastric cancer. In embodiments, the cancer is renal cancer. In embodiments, the cancer is head and neck cancer. In embodiments, the cancer is bone cancer. In embodiments, the cancer is skin cancer. In embodiments, the cancer is prostate cancer.

In an aspect is provided a method of detecting a ROR2 expressing cell, the method including (i) contacting a ROR2-expressing cell with an antibody provided herein including embodiments thereof; (ii) and detecting binding of the antibody to a ROR2 protein expressed by the cell. In embodiments, the antibody is attached to a detectable moiety.

In an aspect is a method of delivering a therapeutic agent to a ROR2 expressing cell, the method including contacting a ROR2 expressing cell with an antibody provided herein including embodiments thereof, wherein the antibody is attached to a therapeutic agent. In embodiments, the therapeutic agent is an anti-cancer agent. Exemplary anti-cancer agent include without limitation any anti-cancer agent conventionally used and known in the art, for example, calicheamicin, duocarmycin, pyrrolobenzodiazepine, (PBD), SN-38, DXd and anti-tubulin.

Methods for generating antibody drug conjugates are well known in the art and described for example, by Hafeez, U. et al. Antibody-Drug Conjugates for Cancer Therapy: Molecules 2020, 25, 4764: doi:10.3390/molecules25204764.: Ponziani, S. et al. Antibody-Drug Conjugates: The New Frontier of Chemotherpy. Int. J. Mol. Sci. 2020, 21, 5510: doi:10.3390/ijms21155510. and; Joubert, N. et al. Antibody-Drug Conjugates: The Last Decade. Pharmaceuticals 2020, 13, 245; doi:10.3390/ph13090245.; which are incorporated by reference herein in their entirety and for all purposes.

For the methods provided herein, in embodiments, the contacting occurs in vitro. In embodiments, the ROR2-expressing cell is in a subject. In embodiments, the subject is a healthy subject. In embodiments, the subject is a subject having cancer. In embodiments, the cancer is a solid tumor malignancy. In embodiments, the cancer is breast cancer, ovarian cancer, pancreatic cancer, cervical cancer, gastric cancer, renal cancer, head and neck cancer, bone cancer, skin cancer or prostate cancer. In embodiments, the cancer is breast cancer. In embodiments, the cancer is ovarian cancer. In embodiments, the cancer is pancreatic cancer. In embodiments, the cancer is cervical cancer. In embodiments, the cancer is gastric cancer. In embodiments, the cancer is renal cancer. In embodiments, the cancer is head and neck cancer. In embodiments, the cancer is bone cancer. In embodiments, the cancer is skin cancer. In embodiments, the cancer is prostate cancer.

For the methods provided herein, in embodiments, the ROR2 expressing cell is a cancer cell. In embodiments, the cancer cell is cancer is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell. In embodiments, the cancer cell is a breast cancer cell. In embodiments, the cancer cell is an ovarian cancer cell. In embodiments, the cancer cell is a pancreatic cancer cell. In embodiments, the cancer cell is cancer is a cervical cancer cell. In embodiments, the cancer cell is cancer is a gastric cancer cell. In embodiments, the cancer cell is cancer is a renal cancer cell. In embodiments, the cancer cell is cancer is a head and neck cancer cell. In embodiments, the cancer cell is a cancer is bone cancer cell. In embodiments, the cancer cell is cancer is a skin cancer cell. In embodiments, the cancer cell is cancer is a prostate cancer cell.

For the methods provided herein, in embodiments, the antibody is administered at an amount from about 0.01 nM to about 10 nM. In embodiments, the antibody is administered at an amount from about 0.05 nM to about 10 nM. In embodiments, the antibody is administered at an amount from about 0.1 nM to about 10 nM. In embodiments, the antibody is administered at an amount from about 0.5 nM to about 10 nM. In embodiments, the antibody is administered at an amount from about 1 nM to about 10 nM. In embodiments, the antibody is administered at an amount from about 2 nM to about 10 nM. In embodiments, the antibody is administered at an amount from about 4 nM to about 10 nM. In embodiments, the antibody is administered at an amount from about 6 nM to about 10 nM. In embodiments, the antibody is administered at an amount from about 4 nM to about 10 nM. In embodiments, the antibody is administered at an amount from about 8 nM to about 10 nM. In embodiments, the antibody is administered at an amount of about 0.01 nM, 0.05 nM, 0.1 nM, 0.5 nM, 1 nM, 2 nM, 2 nM, 4 nM, 5 nM, 6 nM, 7 nM, 8 nM, 9 nM or 10 nM.

In embodiments, the antibody is administered at an amount from 0.01 nM to 10 nM. In embodiments, the antibody is administered at an amount from 0.05 nM to 10 nM. In embodiments, the antibody is administered at an amount from 0.1 nM to 10 nM. In embodiments, the antibody is administered at an amount from 0.5 nM to 10 nM. In embodiments, the antibody is administered at an amount from 1 nM to 10 nM. In embodiments, the antibody is administered at an amount from 2 nM to 10 nM. In embodiments, the antibody is administered at an amount from 4 nM to 10 nM. In embodiments, the antibody is administered at an amount from 6 nM to 10 nM. In embodiments, the antibody is administered at an amount from 4 nM to 10 nM. In embodiments, the antibody is administered at an amount from 8 nM to 10 nM. In embodiments, the antibody is administered at an amount of 0.01 nM, 0.05 nM, 0.1 nM, 0.5 nM, 1 nM, 2 nM, 2 nM, 4 nM, 5 nM, 6 nM, 7 nM, 8 nM, 9 nM or 10 nM.

In embodiments, the antibody is administered at an amount from about 0.01 nM to about 8 nM. In embodiments, the antibody is administered at an amount from about 0.05 nM to about 8 nM. In embodiments, the antibody is administered at an amount from about 0.1 nM to about 8 nM. In embodiments, the antibody is administered at an amount from about 0.5 nM to about 8 nM. In embodiments, the antibody is administered at an amount from about 1 nM to about 8 nM. In embodiments, the antibody is administered at an amount from about 2 nM to about 8 nM. In embodiments, the antibody is administered at an amount from about 4 nM to about 8 nM. In embodiments, the antibody is administered at an amount from about 6 nM to about 8 nM. In embodiments, the antibody is administered at an amount from about 4 nM to about 8 nM.

In embodiments, the antibody is administered at an amount from 0.01 nM to 8 nM. In embodiments, the antibody is administered at an amount from 0.05 nM to 8 nM. In embodiments, the antibody is administered at an amount from 0.1 nM to 8 nM. In embodiments, the antibody is administered at an amount from 0.5 nM to 8 nM. In embodiments, the antibody is administered at an amount from 1 nM to 8 nM. In embodiments, the antibody is administered at an amount from 2 nM to 8 nM. In embodiments, the antibody is administered at an amount from 4 nM to 8 nM. In embodiments, the antibody is administered at an amount from 6 nM to 8 nM. In embodiments, the antibody is administered at an amount from 4 nM to 8 nM.

In embodiments, the antibody is administered at an amount from about 0.01 nM to about 6 nM. In embodiments, the antibody is administered at an amount from about 0.05 nM to about 6 nM. In embodiments, the antibody is administered at an amount from about 0.1 nM to about 6 nM. In embodiments, the antibody is administered at an amount from about 0.5 nM to about 8 nM. In embodiments, the antibody is administered at an amount from about 1 nM to about 6 nM. In embodiments, the antibody is administered at an amount from about 2 nM to about 6 nM. In embodiments, the antibody is administered at an amount from about 4 nM to about 6 nM.

In embodiments, the antibody is administered at an amount from 0.01 nM to 6 nM. In embodiments, the antibody is administered at an amount from 0.05 nM to 6 nM. In embodiments, the antibody is administered at an amount from 0.1 nM to 6 nM. In embodiments, the antibody is administered at an amount from 0.5 nM to 6 nM. In embodiments, the antibody is administered at an amount from 1 nM to 6 nM. In embodiments, the antibody is administered at an amount from 2 nM to 6 nM. In embodiments, the antibody is administered at an amount from 4 nM to 6 nM.

In embodiments, the antibody is administered at an amount from about 0.01 nM to about 4 nM. In embodiments, the antibody is administered at an amount from about 0.05 nM to about 4 nM. In embodiments, the antibody is administered at an amount from about 0.1 nM to about 4 nM. In embodiments, the antibody is administered at an amount from about 0.5 nM to about 4 nM. In embodiments, the antibody is administered at an amount from about 1 nM to about 4 nM. In embodiments, the antibody is administered at an amount from about 2 nM to about 4 nM.

In embodiments, the antibody is administered at an amount from 0.01 nM to 4 nM. In embodiments, the antibody is administered at an amount from 0.05 nM to 4 nM. In embodiments, the antibody is administered at an amount from 0.1 nM to 4 nM. In embodiments, the antibody is administered at an amount from 0.5 nM to 4 nM. In embodiments, the antibody is administered at an amount from 1 nM to 4 nM. In embodiments, the antibody is administered at an amount from 2 nM to 4 nM.

In embodiments, the antibody is administered at an amount from about 0.01 nM to about 2 nM. In embodiments, the antibody is administered at an amount from about 0.05 nM to about 2 nM. In embodiments, the antibody is administered at an amount from about 0.1 nM to about 2 nM. In embodiments, the antibody is administered at an amount from about 0.5 nM to about 2 nM. In embodiments, the antibody is administered at an amount from about 1 nM to about 2 nM.

In embodiments, the antibody is administered at an amount from 0.01 nM to 2 nM. In embodiments, the antibody is administered at an amount from 0.05 nM to 2 nM. In embodiments, the antibody is administered at an amount from 0.1 nM to 2 nM. In embodiments, the antibody is administered at an amount from 0.5 nM to 2 nM. In embodiments, the antibody is administered at an amount from 1 nM to 2 nM.

In embodiments, the antibody is administered at an amount from about 0.01 nM to about 1 nM. In embodiments, the antibody is administered at an amount from about 0.05 nM to about 1 nM. In embodiments, the antibody is administered at an amount from about 0.1 nM to about 1 nM. In embodiments, the antibody is administered at an amount from about 0.5 nM to about 1 nM.

In embodiments, the antibody is administered at an amount from 0.01 nM to 1 nM. In embodiments, the antibody is administered at an amount from 0.05 nM to 1 nM. In embodiments, the antibody is administered at an amount from 0.1 nM to 1 nM. In embodiments, the antibody is administered at an amount from 0.5 nM to 1 nM.

In embodiments, the antibody is administered at an amount of about 3.15 nM. In embodiments, the antibody is administered at an amount of 3.15 nM. In embodiments, the antibody is administered at an amount of about 1.05 nM. In embodiments, the antibody is administered at an amount of 1.05 nM.

It is understood that the the bispecific antibody or the chimeric antigen receptor provided herein including embodiments thereof may be administered at any of the concentrations described herein for the administration of the antibody (e.g., 0.01 nM-10 nM).

In embodiments, the antibody is administered at an amount from about 10 μg to about 500 μg. In embodiments, the antibody is administered at an amount from about 20 μg to about 500 μg. In embodiments, the antibody is administered at an amount from about 30 μg to about 500 μg. In embodiments, the antibody is administered at an amount from about 40 μg to about 500 μg. In embodiments, the antibody is administered at an amount from about 50 μg to about 500 μg. In embodiments, the antibody is administered at an amount from about 60 μg to about 500 μg. In embodiments, the antibody is administered at an amount from about 70 μg to about 500 μg. In embodiments, the antibody is administered at an amount from about 80 μg to about 500 μg. In embodiments, the antibody is administered at an amount from about 90 μg to about 500 μg. In embodiments, the antibody is administered at an amount from about 100 μg to about 500 ug.

In embodiments, the antibody is administered at an amount from about 110 μg to about 500 μg. In embodiments, the antibody is administered at an amount from about 120 μg to about 500 μg. In embodiments, the antibody is administered at an amount from about 130 μg to about 500 μg. In embodiments, the antibody is administered at an amount from about 140 μg to about 500 μg. In embodiments, the antibody is administered at an amount from about 150 µg to about 500 µg. In embodiments, the antibody is administered at an amount from about 160 µg to about 500 µg. In embodiments, the antibody is administered at an amount from about 170 µg to about 500 µg. In embodiments, the antibody is administered at an amount from about 180 µg to about 500 µg. In embodiments, the antibody is administered at an amount from about 190 µg to about 500 µg. In embodiments, the antibody is administered at an amount from about 200 µg to about 500 ug.

In embodiments, the antibody is administered at an amount from about 210 µg to about 500 µg. In embodiments, the antibody is administered at an amount from about 220 µg to about 500 µg. In embodiments, the antibody is administered at an amount from about 230 µg to about 500 µg. In embodiments, the antibody is administered at an amount from about 240 µg to about 500 µg. In embodiments, the antibody is administered at an amount from about 250 µg to about 500 µg. In embodiments, the antibody is administered at an amount from about 260 µg to about 500 µg. In embodiments, the antibody is administered at an amount from about 270 µg to about 500 µg. In embodiments, the antibody is administered at an amount from about 280 µg to about 500 µg. In embodiments, the antibody is administered at an amount from about 290 µg to about 500 µg. In embodiments, the antibody is administered at an amount from about 300 µg to about 500 ug.

In embodiments, the antibody is administered at an amount from about 310 µg to about 500 µg. In embodiments, the antibody is administered at an amount from about 320 µg to about 500 µg. In embodiments, the antibody is administered at an amount from about 330 µg to about 500 µg. In embodiments, the antibody is administered at an amount from about 340 µg to about 500 µg. In embodiments, the antibody is administered at an amount from about 350 µg to about 500 µg. In embodiments, the antibody is administered at an amount from about 360 µg to about 500 µg. In embodiments, the antibody is administered at an amount from about 370 µg to about 500 µg. In embodiments, the antibody is administered at an amount from about 380 µg to about 500 µg. In embodiments, the antibody is administered at an amount from about 390 µg to about 500 µg. In embodiments, the antibody is administered at an amount from about 400 µg to about 500µ g.

In embodiments, the antibody is administered at an amount from about 410 µg to about 500 µg. In embodiments, the antibody is administered at an amount from about 420 µg to about 500 µg. In embodiments, the antibody is administered at an amount from about 430 µg to about 500 µg. In embodiments, the antibody is administered at an amount from about 440 µg to about 500 µg. In embodiments, the antibody is administered at an amount from about 450 µg to about 500 µg. In embodiments, the antibody is administered at an amount from about 460 µg to about 500 µg. In embodiments, the antibody is administered at an amount from about 470 µg to about 500 µg. In embodiments, the antibody is administered at an amount from about 480 µg to about 500 µg. In embodiments, the antibody is administered at an amount from about 490 µg to about 500 µg.

In embodiments, the antibody is administered at an amount from about 10 µg to about 400 µg. In embodiments, the antibody is administered at an amount from about 20 µg to about 400 µg. In embodiments, the antibody is administered at an amount from about 30 µg to about 400 µg. In embodiments, the antibody is administered at an amount from about 40 µg to about 400 µg. In embodiments, the antibody is administered at an amount from about 50 µg to about 400 µg. In embodiments, the antibody is administered at an amount from about 60 µg to about 400 µg. In embodiments, the antibody is administered at an amount from about 70 µg to about 400 µg. In embodiments, the antibody is administered at an amount from about 80 µg to about 400 µg. In embodiments, the antibody is administered at an amount from about 90 µg to about 400 µg. In embodiments, the antibody is administered at an amount from about 100 µg to about 400 µg.

In embodiments, the antibody is administered at an amount from about 10 µg to about 300 µg. In embodiments, the antibody is administered at an amount from about 20 µg to about 300 µg. In embodiments, the antibody is administered at an amount from about 30 µg to about 300 µg. In embodiments, the antibody is administered at an amount from about 40 µg to about 300 µg. In embodiments, the antibody is administered at an amount from about 50 µg to about 300 µg. In embodiments, the antibody is administered at an amount from about 60 µg to about 300 µg. In embodiments, the antibody is administered at an amount from about 70 µg to about 300 µg. In embodiments, the antibody is administered at an amount from about 80 µg to about 300 µg. In embodiments, the antibody is administered at an amount from about 90 µg to about 300 µg. In embodiments, the antibody is administered at an amount from about 100 µg to about 300 µg.

In embodiments, the antibody is administered at an amount from about 10 µg to about 200 µg. In embodiments, the antibody is administered at an amount from about 20 µg to about 200 µg. In embodiments, the antibody is administered at an amount from about 30 µg to about 200 µg. In embodiments, the antibody is administered at an amount from about 40 µg to about 200 µg. In embodiments, the antibody is administered at an amount from about 50 µg to about 200 µg. In embodiments, the antibody is administered at an amount from about 60 µg to about 200 µg. In embodiments, the antibody is administered at an amount from about 70 µg to about 200 µg. In embodiments, the antibody is administered at an amount from about 80 µg to about 200 µg. In embodiments, the antibody is administered at an amount from about 90 µg to about 200 µg. In embodiments, the antibody is administered at an amount from about 100 µg to about 200 µg.

In embodiments, the antibody is administered at an amount from about 10 µg to about 100 µg. In embodiments, the antibody is administered at an amount from about 20 µg to about 100 µg. In embodiments, the antibody is administered at an amount from about 30 µg to about 100 µg. In embodiments, the antibody is administered at an amount from about 40 µg to about 100 µg. In embodiments, the antibody is administered at an amount from about 50 µg to about 100 µg. In embodiments, the antibody is administered at an amount from about 60 µg to about 100 µg. In embodiments, the antibody is administered at an amount from about 70 µg to about 100 µg. In embodiments, the antibody is administered at an amount from about 80 µg to about 100 µg. In embodiments, the antibody is administered at an amount from about 90 µg to about 100 µg.

In embodiments, the antibody is administered at an amount of about 10 µg, 20 µg, 30 µg, 40 µg, 50 µg, 60 µg, 70 µg, 80 µg, 90 µg, 100 µg, 110 µg, 120 µg, 130 µg, 140 µg, 150µ g, 160 µg, 170 µg, 180 µg, 190 µg, 200 µg, 210 µg, 220 µg, 230 µg, 240 µg, 250 µg, 260 µg, 270 µg, 280 µg, 290 µg, 300 µg, 310 µg, 320 µg, 330 µg, 340 µg, 350 µg, 360 µg, 370 µg, 380 µg, 390 µg, 400 µg, 410 µg, 420 µg, 430 µg, 440 µg, 450 µg, 460 µg, 470 µg, 480 µg, 490µ, or 500 µg.

In embodiments, the antibody is administered at an amount of 10 μg. 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 300 μg, 310 μg, 320 μg, 330 μg, 340 μg, 350 μg, 360 μg, 370 μg, 380 μg, 390μ g, 400 μg, 410 μg, 420 μg, 430 μg, 440 μg, 450 μg, 460 μg, 470 μg, 480 μg, 490μ, or 500μ g.

It is understood that the bispecific antibody or the chimeric antigen receptor provided herein including embodiments thereof may be administered at any of the concentrations described herein for the administration of the antibody (e.g., 10 μg-500 μg).

Methods of Inhibiting Cell Migration

The compositions provided herein, including embodiments thereof, are further contemplated for inhibiting cell migration. Thus, in an aspect is provided a method of inhibiting migration of a ROR2-expressing cell, the method including contacting a ROR2 expressing cell with an antibody provided herein including embodiments thereof. In embodiments, the antibody includes a heavy chain variable domain and a light chain variable domain, wherein the heavy chain variable domain includes: a CDR H1 as set forth in SEQ ID NO:25, a CDR H2 as set forth in SEQ ID NO:26 and a CDR H3 as set forth in SEQ ID NO:27; and wherein the light chain variable domain includes: a CDR L1 as set forth in SEQ ID NO:28, a CDR L2 as set forth in SEQ ID NO:29, and a CDR L3 as set forth in SEQ ID NO:30.

For the methods provided herein, in embodiments, the ROR2 expressing cell is a cancer cell. In embodiments, the cancer cell is cancer is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell. In embodiments, the cancer is cancer is breast cancer. In embodiments, the cancer cell is an ovarian cancer cell. In embodiments, the cancer cell is a pancreatic cancer cell. In embodiments, the cancer cell is cancer is a cervical cancer cell. In embodiments, the cancer cell is cancer is a gastric cancer cell. In embodiments, the cancer cell is cancer is a renal cancer cell. In embodiments, the cancer cell is cancer is a head and neck cancer cell. In embodiments, the cancer cell is a cancer is bone cancer cell. In embodiments, the cancer cell is cancer is a skin cancer cell. In embodiments, the cancer cell is cancer is a prostate cancer cell.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Due to its expression in cancer cells, ROR2 has the potential to serve as a diagnostic and therapeutic target. There have been monoclonal antibodies generated that reportedly bind ROR2 and that are available from commercial sources. However, Applicants found that several reacted with cells expressing ROR2 by immunoblot and/or flow cytometry. Further, Applicants discovered that several of these antibodies also unexpectedly reacted with cells that were deleted of ROR2 using CRISPR-Cas9 technology. This unexpected binding revealed that many commercially available antibodies are not specific for ROR2.

Thus, Applicants generated monoclonal antibodies that specifically target the extracellular portion of human ROR2. For this, mice were immunized with recombinant protein of the extracellular portion (AA 1-403) of the ROR2 protein that include the Ig-like, cysteine rich domain (CRD) and Kringle domains (FIG. 1). Because of the high degree of homology between the murine and human molecules, Applicants co-injected immune stimulatory agents, such as Freund's Complete Adjuvant, to maximize the generation of anti-human ROR2 antibodies.

Hybridomas generated following fusion of splenocytes with a myeloma fusion partner were screened for expression of anti-ROR2 mAb using ELISA and flow cytometry to identify clones that produce antibody that specifically bind to human ROR2. These antibodies are designated in this disclosure as mAbs N-LN or in the more familiar form 6-E6, are listed in Table 1, and the sequences of the heavy and light chain variable regions are depicted in FIG. 2.

TABLE 1

| Characteristics of anti-human ROR2 monoclonal antibodies | | | | |
|---|---|---|---|---|
| mAb Name | Subclass | Sequence | Human ROR2 binding domain | KD (nM) |
| 6E6 | mIgG1 | mKappa | Kringle | <0.1 |
| 4G9 | mIgG2a | mKappa | Ig-like | ~1.9 |
| 5C11 | mIgG1 | mKappa | Kringle | >40 |
| 5G3 | mIgG2a | mKappa | Ig-like | >40 |

Applicants assessed binding specificity and relative affinities of each mAb using recombinant ROR2-extracellular protein in an ELISA assay, in which binding was measured using decreasing/limiting amounts of ROR2 protein and assessed in combination with decreasing concentrations of each of the four mAb (FIG. 3). Higher absorbance values for 6E6 and 4G9 at both lower ROR2 protein amounts and lower concentrations of mAb, indicate these mAb have higher affinities compared to 5C11 and 5G3. Equilibrium dissociation constants (Kd) were measured in a kinetic exclusion assay (KinExA) that measures the equilibrium binding affinity and kinetics between unmodified molecules in solution. The 6E6 mAb binds to the target ROR2 extracellular sequence with a Kd of about 0.1 nM. 4G9 binds to the extracellular domain of human ROR2 with a Kd of about 2 nM (FIGS. 4A and 4B). Analysis of the 5C11 and 5G3 mAb determined that each has a Kd greater than about 40 nM, consistent with the results from the ELISA analysis above.

Figure 5:
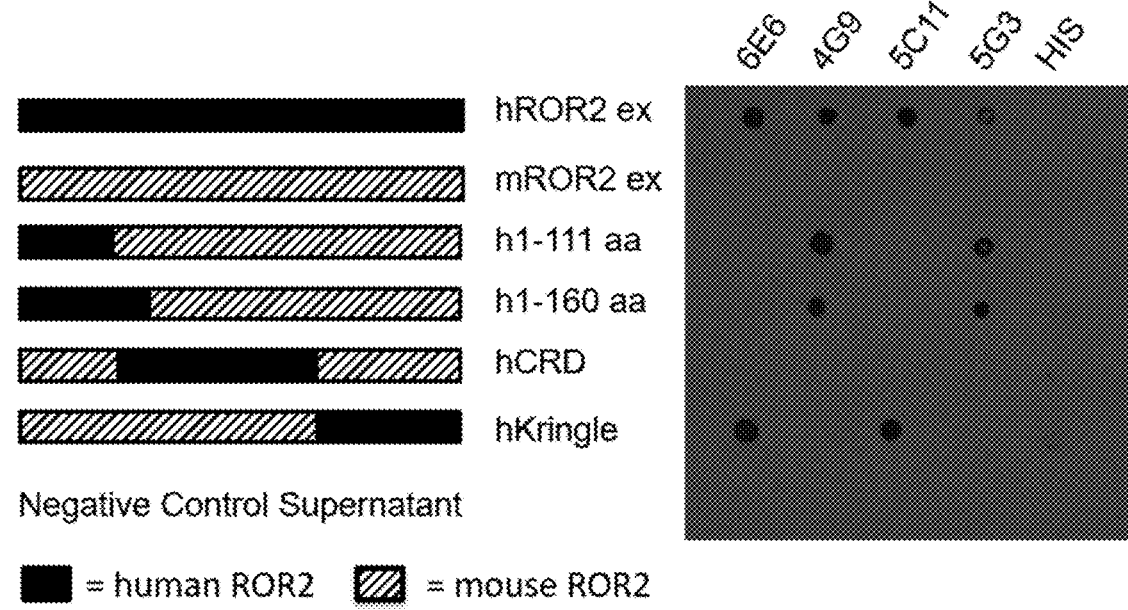
FIG. 5. Identification of the binding regions of anti-human ROR2 mAb by assessment of binding to chimeric human/house recombinant ROR2 protein. The left panel shows schematics of the chimeric constructs of the extracellular portion of ROR2 used to map the binding region of each of the four ROR2 mAb. The dark regions of each construct indicate human ROR2 and the hatched portions regions of mouse ROR2. h1-111 and h1-160 refer to the first 111 and 160 amino acids of human ROR2, respectively. hCRD and hKringle contain the cysteine rich domain and the Kringle domain of human ROR2. Each recombinant protein was transferred onto nylon membrane, probed with the the 6E6, 4G9, 5C11, 5G3 or anti-his tag mAb. and detected with an anti-mouse IgG antibody conjugated with horse radish peroxidase, as shown in the right panel. The 6E5 and 5C11 mAbs bind to ROR2 recombinant proteins that contain the human kringle domain. The 4G9 and 5G3 mAbs bind to ROR2 recombinant proteins within the first 111 aa of human ROR2, which includes the Ig-like domain.

Applicants developed a series recombinant human/mouse hybrid proteins that isolate specific domains of the human ROR2 protein. These recombinant proteins were used to identify the specific binding domains that each of the four mAb target (FIG. 5). The 6E6 and 5C11 mAb bind to the Kringle domain of human, but not mouse, ROR2. The 4G9 and 5G3 mAb bind within the first 111 aa of human ROR2, which includes the Ig-like domain. None of the four mAb bind mouse ROR2.

Figure 6:
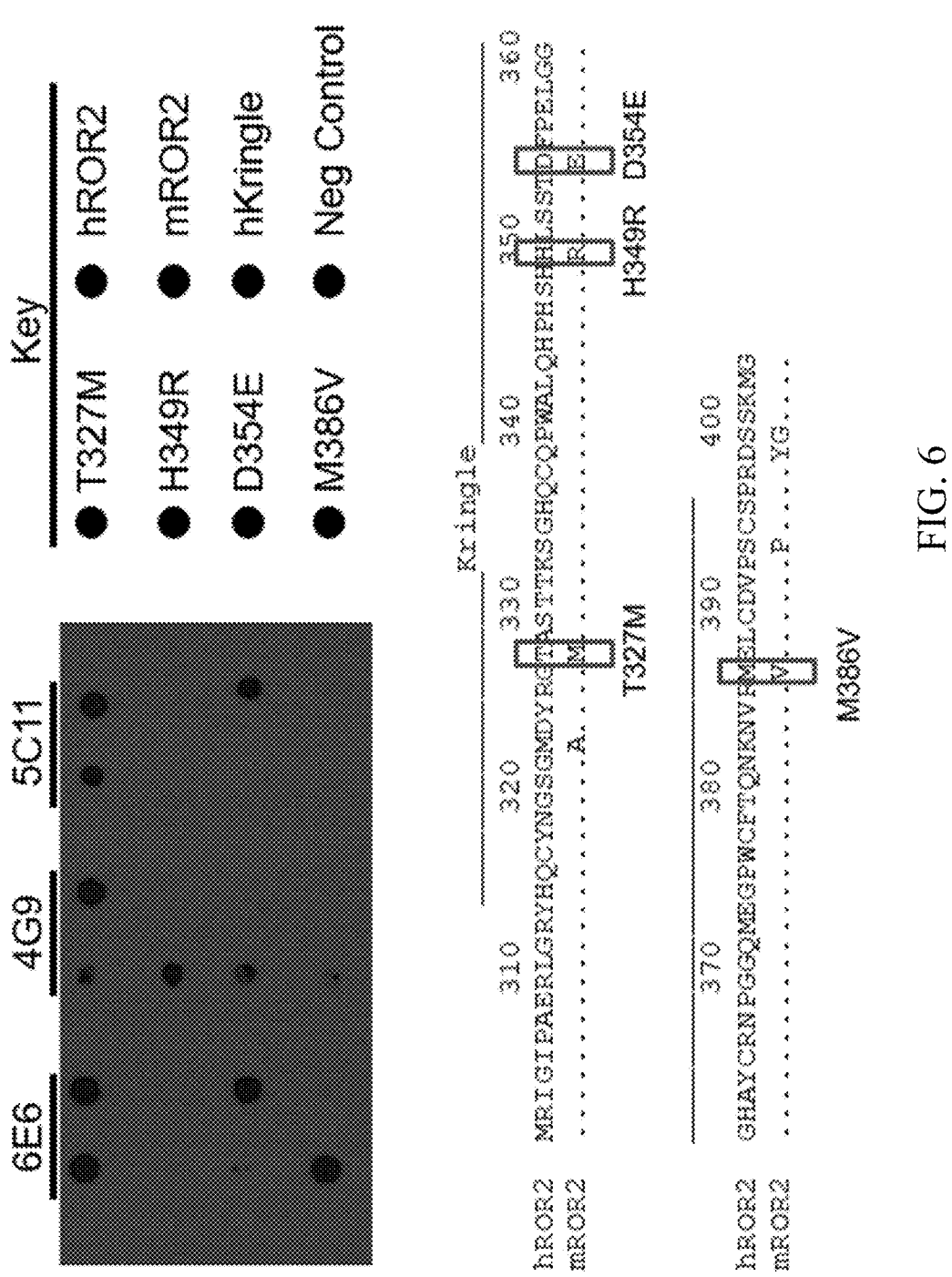
FIG. 6. Identification of amino acids required for binding of anti-human ROR2 mAb to the Kringle domain of human ROR2. Binding of 6E6, 4G9 and 5C11 mAb was assessed using recombinant human ROR2 proteins in which one amino acid that differs between human and mouse ROR2 within the kringle domain was replaced with the corresponding amino acid of mouse ROR2. Each recombinant protein was transferred onto nylon membrane, probed with the the 6E6, 4G9, or 5C11 mAb, and detected with an anti-mouse IgG antibody conjugated with horse radish peroxidase, as shown in the top panel. Alignment of the protein sequences of the kringle domain of human (SEQ ID NO:122) and mouse ROR2 are shown in the lower panel, and the boxed amino acids indicate the amino acids changes made for each recombinant protein.

Applicants also refined this procedure to identify specific amino acids that are critical for the binding of the two anti-ROR2 mAbs that bind within the Kringle domain (FIG. 6). Applicants produced several recombinant human ROR2 proteins in which one of the amino acids that differs between human and mouse ROR2 within the Kringle domain was replaced with the corresponding amino acid of mouse ROR2. Assessment of binding of 6E6 and 5C11 mAbs indicates that they require a histidine residue at position 349 and an aspartic acid at position 354 for binding to the Kringle domain of human ROR2, as replacement of these amino acids with the murine molecule's arginine and glutamic acid residues, respectively, the 6E6 and 5C11 mAbs no longer bind the ROR2 protein. Additionally, 5C11 requires a methionine residue at position 386, as binding is lost upon replacement of methionine with the valine of mouse ROR2.

Figure 7A:
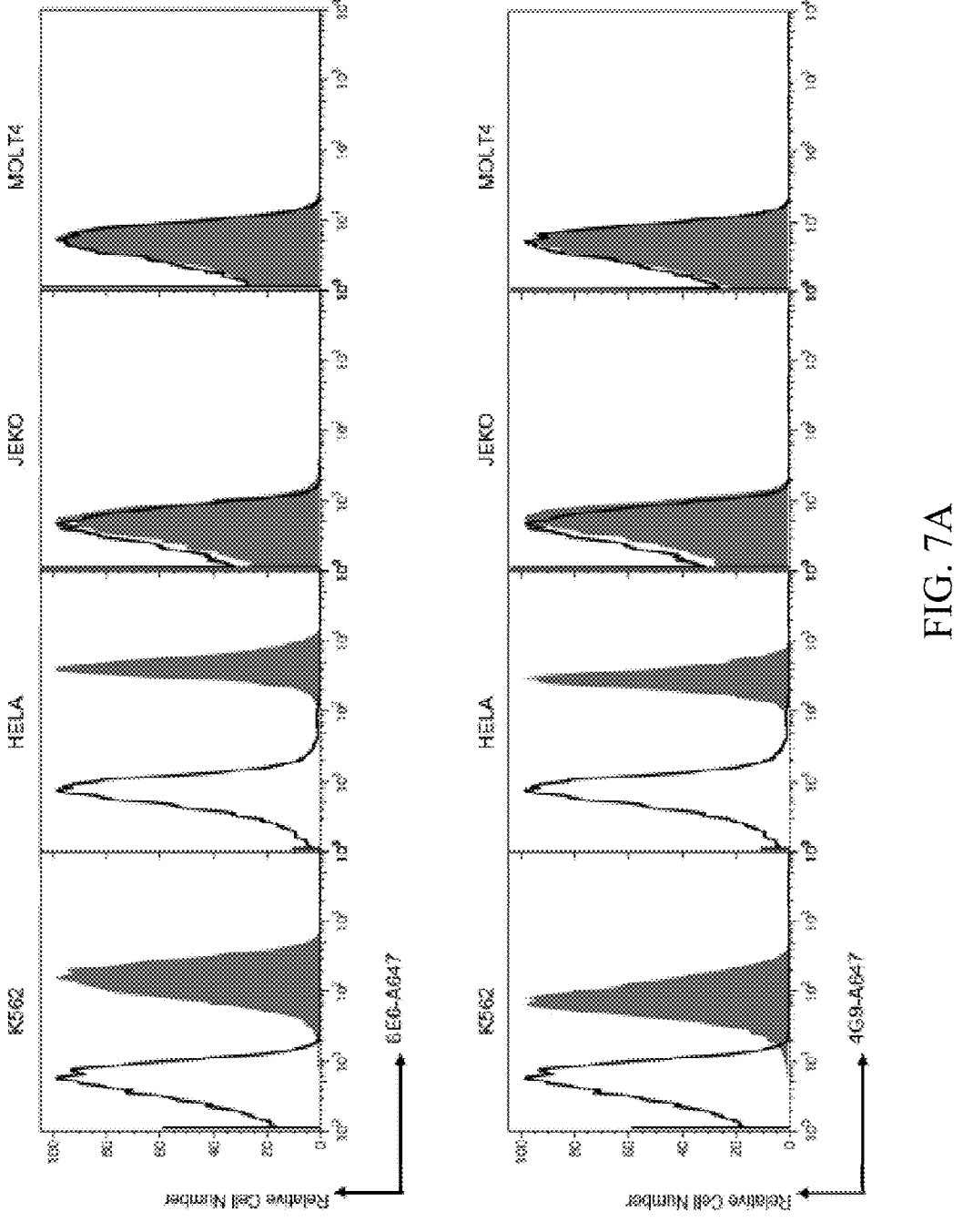
FIGS. 7A and 7B. 6E6 and 4G9 anti-human ROR2 mAb specifically bind human ROR2.
Figure 7B:
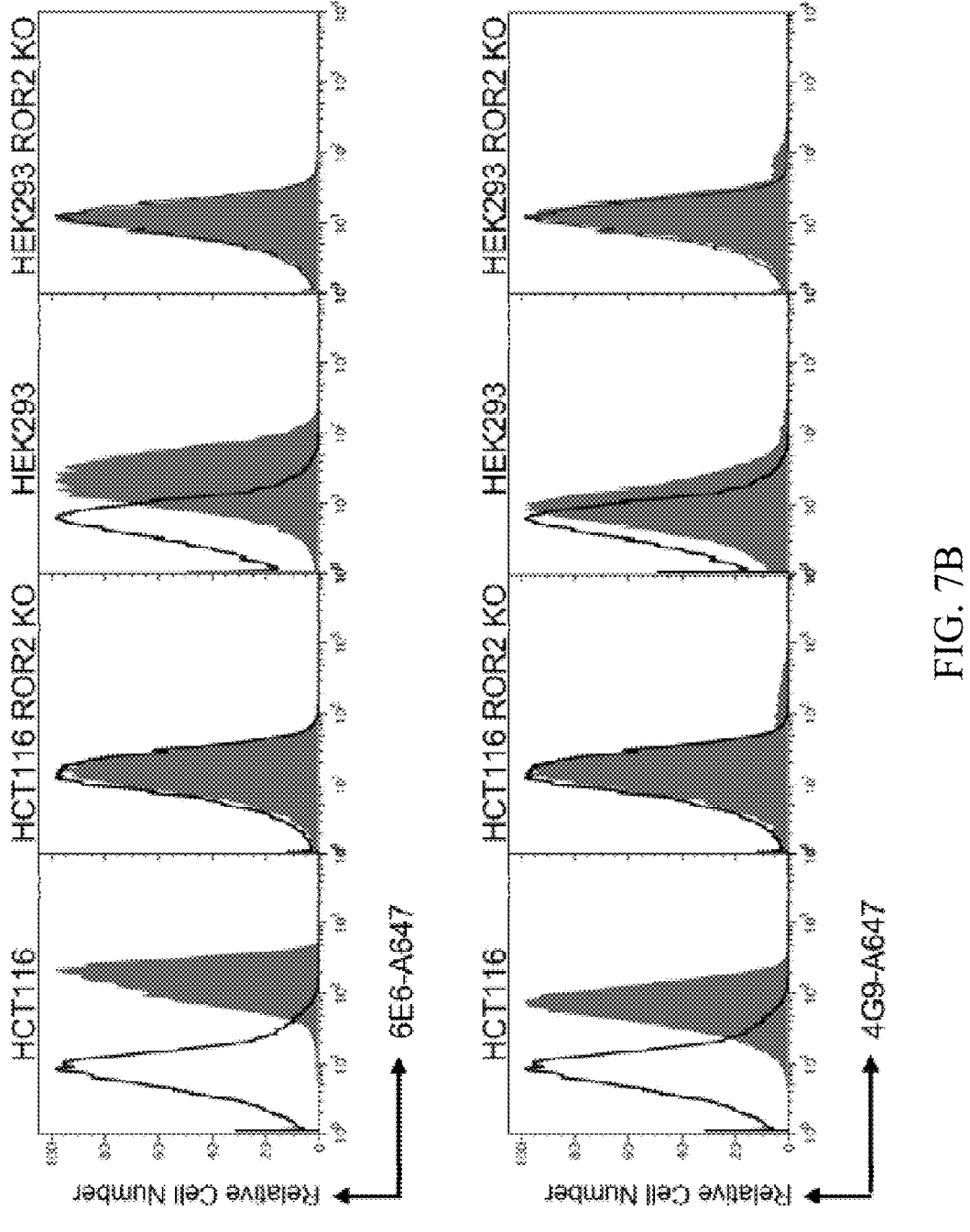

Binding of each of the mAb to human ROR2 was validated by flow cytometric staining and analysis of several cell lines known to express ROR2 using each mAb conjugated with Alexa647 (FIG. 7A). Specificity was validated by the absence of binding to HCT116 colorectal cancer cells and HEK293 cells in which ROR2 expression was eliminated using CRISPR-cas9 (FIG. 7B). Validation of the specificity of these mAb sets them apart from many commercially available anti-human ROR2 polyclonal and monoclonal antibodies, as in the last few years several that have been widely used in published studies, have subsequently been recalled and are no longer available, as they were determined to not be specific for ROR2.

Figure 8:
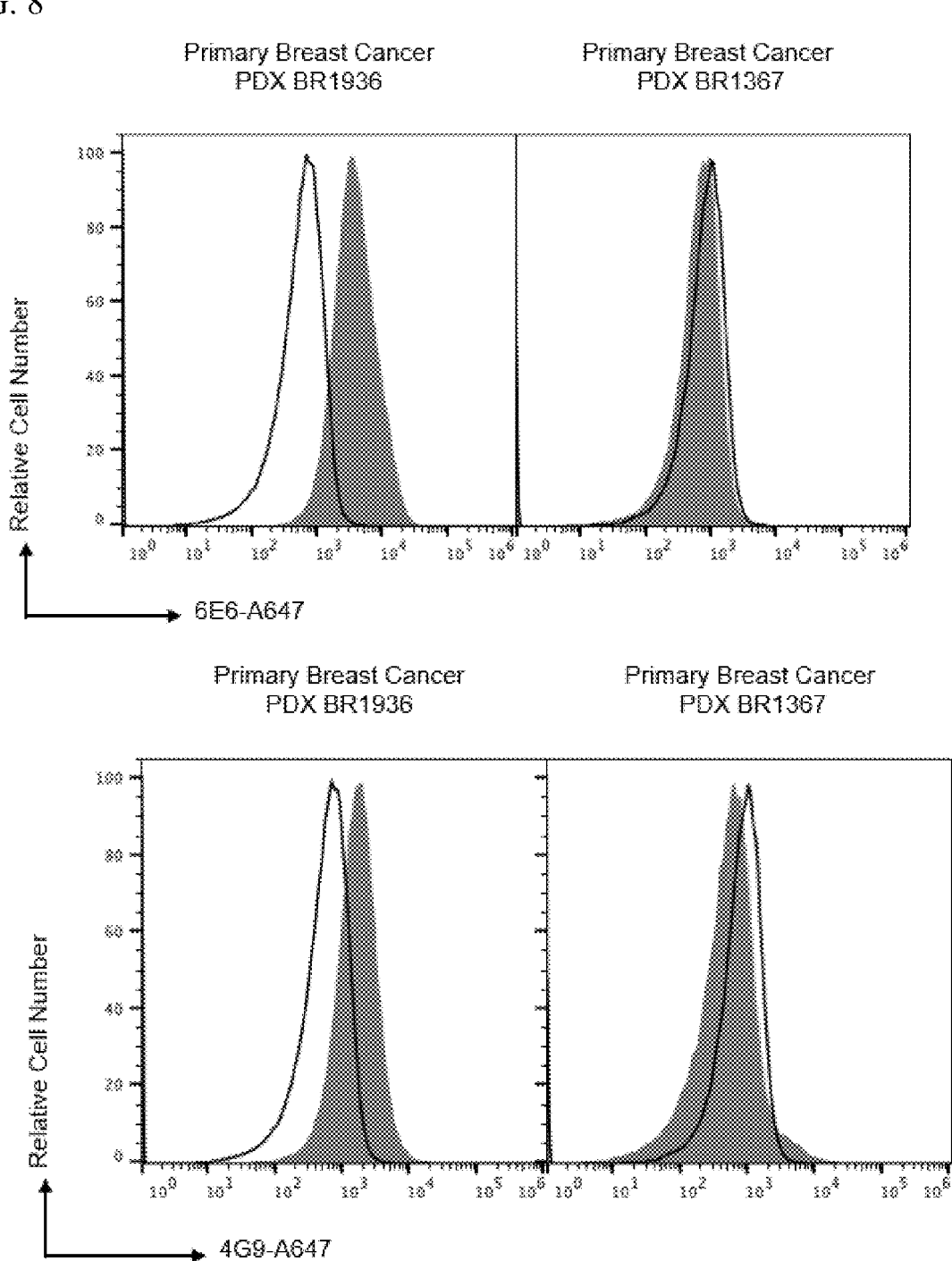
FIG. 8. 6E6 and 4G9 anti-human ROR2 mAb bind to ROR2 expressed by BR1936 breast cancer PDX cells. BR1936 and BR1367 (ROR2 negative) breast cancer PDX cells were stained with 10 μg/ml of 6E6 or 4G9 anti-human ROR2-Alexa647 conjugated mAb (shaded histograms) or equal amounts of isotype matched control mAb (open histograms). Cells were stained on ice for 20 minutes, washed and analyzed by flow cytometry. Histograms depict the relative fluorescence intensity (x axis) of viable cells as determined by light scatter characteristics. Both 6E6 and 4G9 bind to BR1936 cells, but not BR1367 cells that do not express human ROR2.
Figure 9:
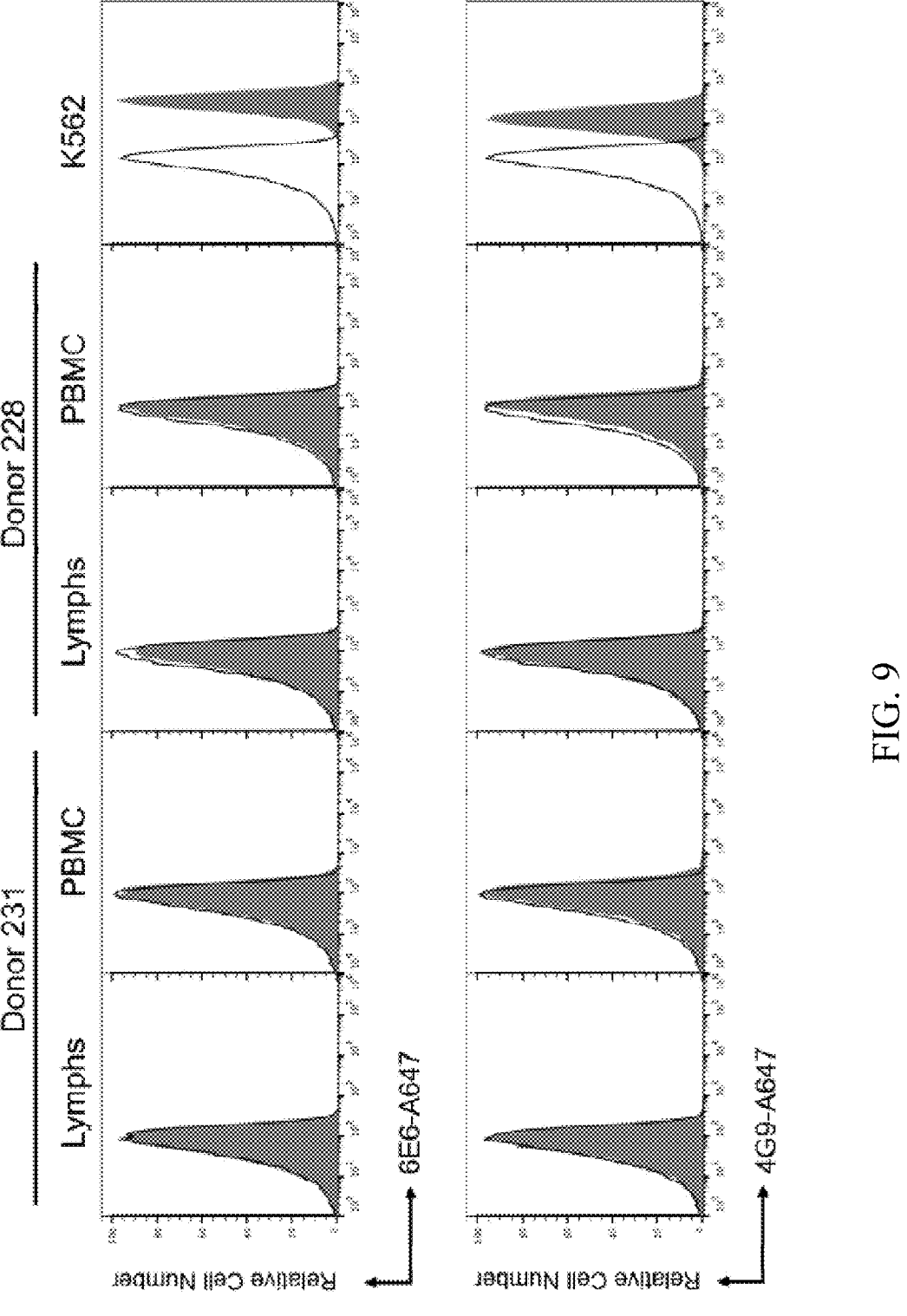
FIG. 9. 6E6 and 4G9 anti-human ROR2 mAb do not bind to peripheral blood mononuclear cells (PBMC) or lymphocytes isolated from healthy donors. PBMC were isolated by ficoll density centrifugation from whole blood obtained with consent from healthy donors. Cells were stained with 5 μg/ml of 6E6 or 4G9 anti-human ROR2-Alexa647 conjugated mAb (shaded histograms) or equal amounts of isotype matched control mAb (open histograms) on ice for 20 minutes, washed and analyzed by flow cytometry. Histograms depict staining of live viable mononuclear cells or lymphocytes as determined by light scatter characteristics. Staining of K562 cells was performed as a positive control.

Additionally, the 6E6 and 4G9 mAb have been tested on primary human cells. 6E6 and 4G9) each stain ROR2 on BR1936, but not BR1367 (ROR2 negative), human breast cancer PDX cells (FIG. 8), compared to staining with equal amounts of isotype matched Alex647-conjugated control antibody. Neither 6E6 nor 4G9 demonstrate binding to peripheral blood mononuclear cells isolated from several healthy donors (FIG. 9).

Figure 10A:
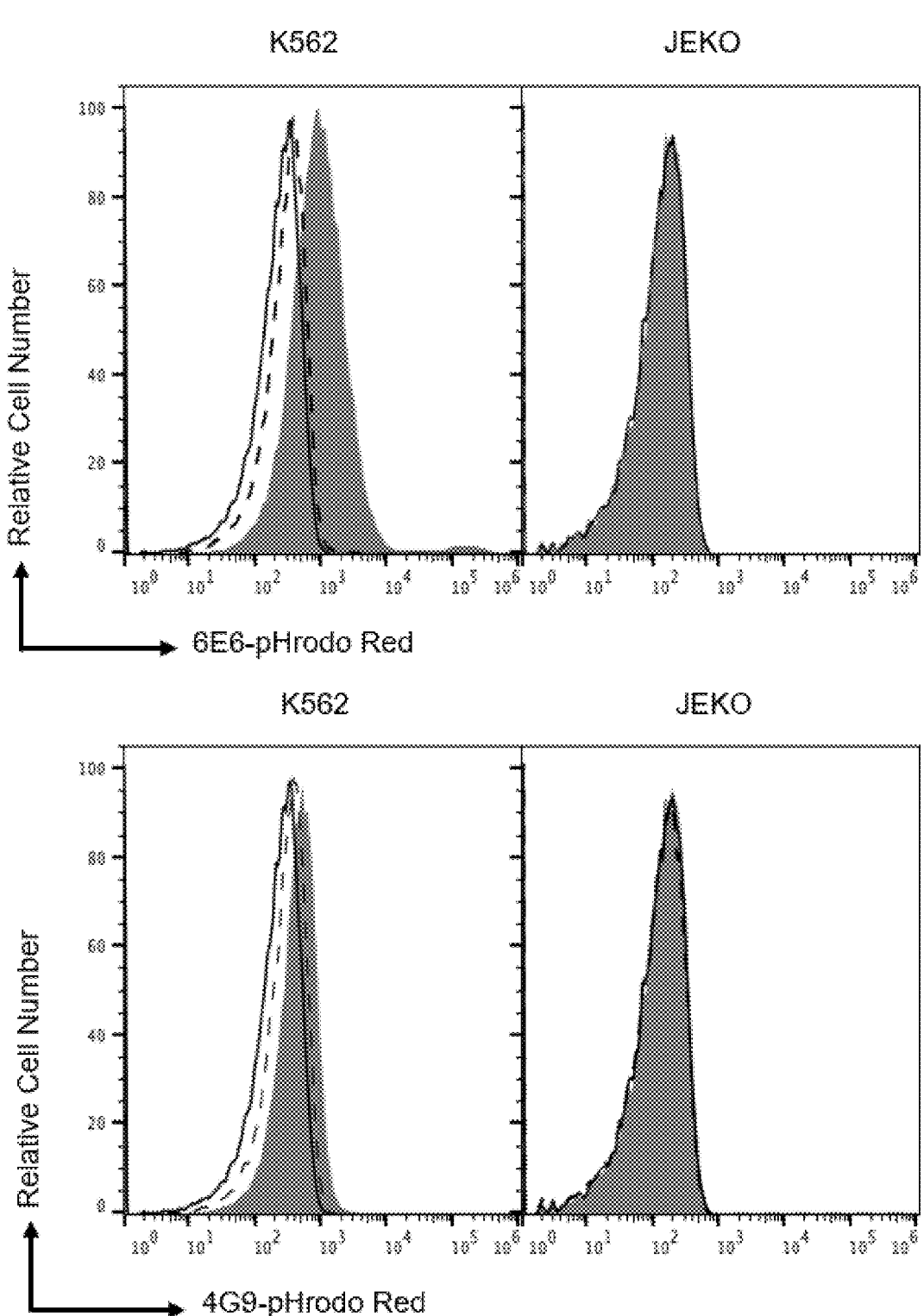
FIGS. 10A and 10B. 6E6 and 4G9 anti-human ROR2 mAb are internalized by K562 but not JEKO cells. K562 and JEKO (ROR2 negative) cells were stained with 10 μg/ml of 6E6 or 4G9 anti-human ROR2-pHrodo conjugated mAb on ice for 30 minutes, washed and aliquoted into four fractions. One plate was kept on ice, and the other three transferred to 37° C. for 30, 60 or 120 minutes. Following incubation, cells were washed and analyzed by flow cytometry.
Figure 10B:
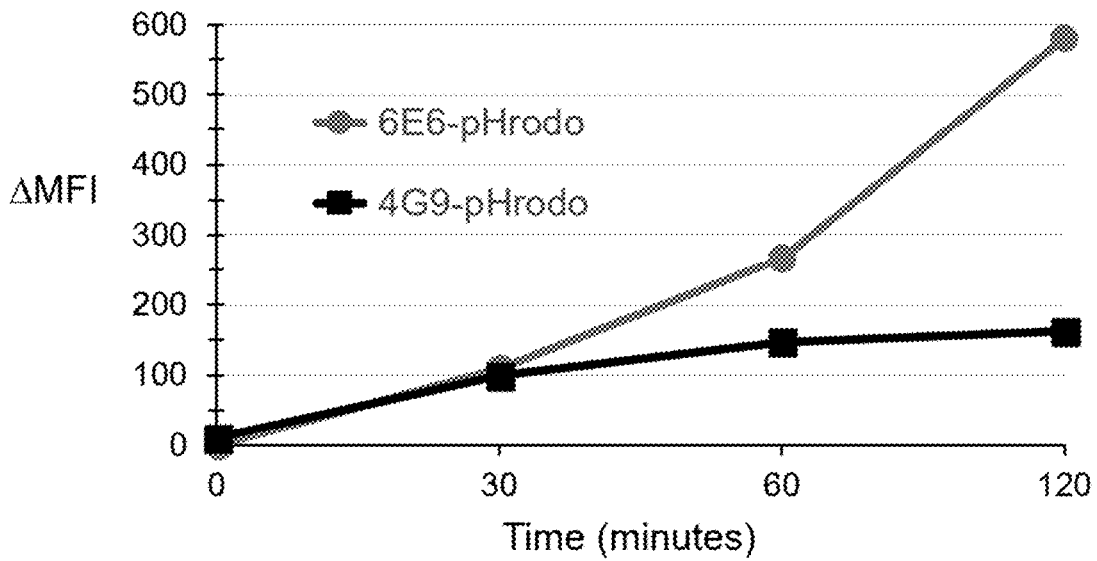

Initial functional studies of 6E6 and 4G9, demonstrate that each mAb is internalized, as assessed by increased relative fluorescence with 6E6 and 4G9 mAb conjugated to the pH sensitive dye pHrodo. Following staining with saturating amounts of pHrodo-conjugated mAb, cells were washed, incubated for 2 hours at either 37° C. or 4° C., and analyzed by flow cytometry for changes in relative cell fluorescence associated with pHrodo and lower intracellular pH (FIG. 10), indicating that the antibody was internalized into primary endosomes and lysosomes of the treated cells that express ROR2. Both the 6E6 and 4G9 mAb had increased relative fluorescence in K562 cells at 37° C., relative to unstained cells or cells incubated at 4° C., and showed no difference at either temperature for JEKO cells that lacked ROR2 expression. Applicants discovered that 6E6 internalized with greater efficiency than 4G9. Because antibodies that internalize into primary endosomes/lysosomes have been demonstrated to be effective vehicles for delivering drugs or other molecules conjugated to them to the cell that expresses the target antigen, in this case ROR2, Applicants conclude from these data that 6E6 would be very effective as the antibody in antibody-drug conjugates (or ADCs) that then could target cells that express ROR2.

Thus, antibodies targeting the epitope recognized by 6E6 can be used to deliver drugs or other compounds efficiently to cells that express ROR2 in a fashion that allows for the drug/compound to be internalized into the cell and active within the ROR2 cell. This allows for selective targeting of ROR2 positive cells in vivo. Further, these antibodies may be used for targeting ROR2-expressing cells with agents that can identify the ROR2-expressing cell for diagnostic imaging or fluorescence identification during surgical extraction of ROR2-positive cancer cells.

Figure 11A:
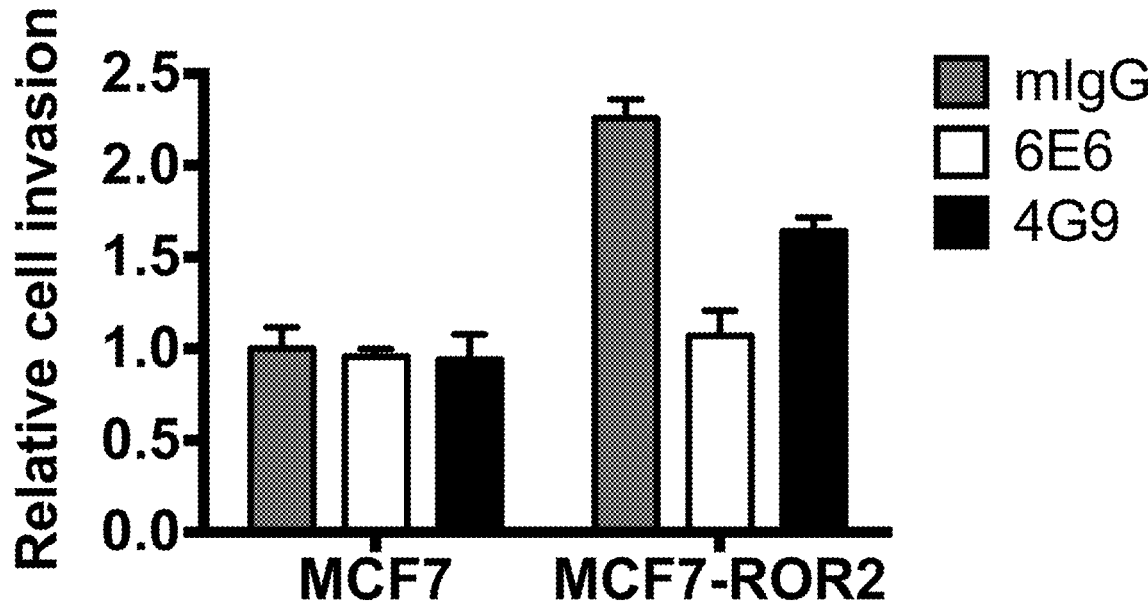
FIGS. 11A and 11B. 6E6 and 4G9 anti-human ROR2 mAb inhibit Wnt5a induced invasion of MCF7-ROR breast cancer cells. MCF7 breast cancer cells transfected with either control vector or ROR2-expression vector were cultured overnight in Dulbecco's modified Eagle's medium (DMEM) supplemented with 0).5% fetal bovine serum (FBS) without growth factors. The following day, cells were removed and $10^5$ cells suspended in 0.5% FBS DMEM media with 100 ng/ml recombinant Wnt5a and 25 μg/ml of mouse IgG. 6E6, or 4G9 anti-human 30) ROR2 mAb in Matrigel-coated, growth-factor-reduced. 8 μM pore size invasion chambers. Following incubation at 37° C. for 24 hours, wells were washed with phosphate buffered saline (PBS) and fixed with 4% paraformaldehyde. Cells on the apical side of each insert were removed by scraping, while cells that migrated to the basal side of the membrane were stained by Diff-Quick staining reagents and visualized with a Nikon inverted microscope.
Figure 11B:
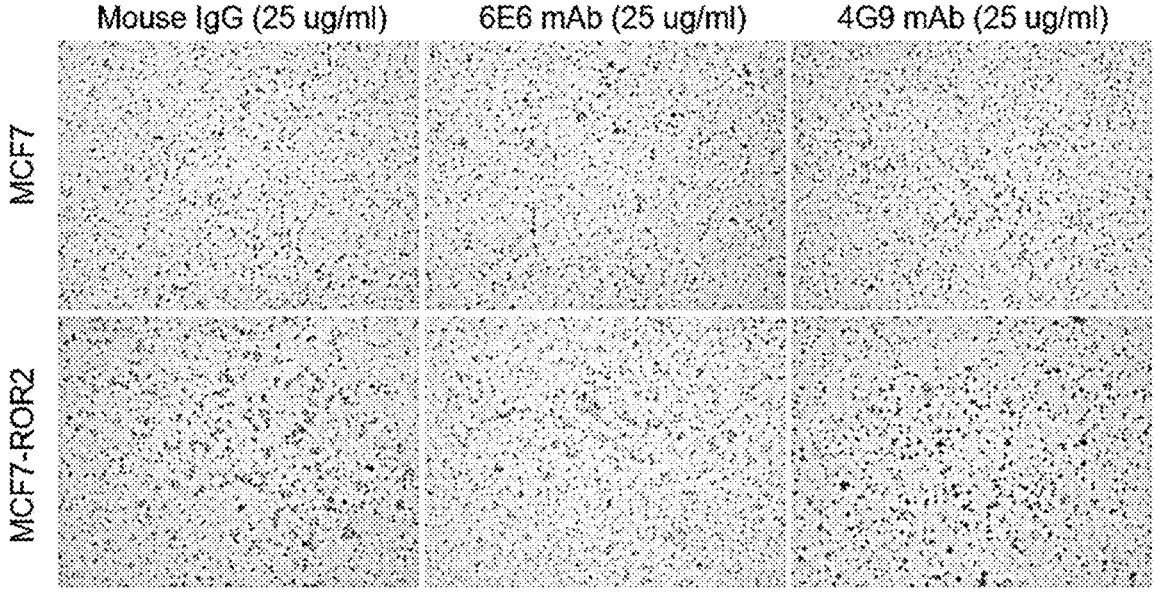

Tumor-cell expression of ROR2 may have functional significance. Transfection of the breast-cancer cell line. MCF7 with an expression vector encoding ROR2, generated MCF7-ROR2 cells that expressed surface ROR2. MCF7-ROR2 cells had enhanced motility and tissue invasiveness in response to Wnt5a than parental MCF7 cells, which do not express ROR2. The increased motility and invasiveness are associated with an enhanced capacity to form metastatic tumors in immune-deficient mice, such has been observed using MCF7 cells transfected to express ROR1.1 Applicants examined whether any one of the specific anti-ROR2 mAb could inhibit the capacity of Wnt5a to enhance the migration/invasiveness of MCF7-ROR2 cells in vitro. For this Applicants established cell migration assay and invasion assays to evaluate the capacity of cells to migrate or invade Matrigel, respectively. As demonstrated in FIG. 11. MCF7-ROR2 cells treated with Wnt5a had 2-fold greater migration/invasiveness than Wnt5a-treated MCF7 cells: the increased migration MCF7-ROR2 cells was not inhibited when control, non-specific mouse IgG was added to the cultures (FIG. 11A, gray bars). Applicants discovered. 25 ug/ml of 6E6 (white bars), but not 4G9 (black bars), provided for complete inhibition of Wnt5a-induced migration of MCF7-ROR2 cells, such that it no longer had an advantage over MCF7 cells in the migration/invasiveness assay. These data demonstrate that 6E6 can inhibit the function of ROR2 in enhancing tumor cell migration and invasiveness. By extension, this implies that 6E6 reacts with ROR2 in a fashion that inhibits ROR2-signaling, which contributes to enhanced metastases. The fact that 6E6 had such activity, but not 4G9, implies that the epitope recognized by 6E6 is important for inhibition of ROR2 signaling leading to enhanced tumor cell invasion. Thus, antibodies that bind the epitope recognized by 6E6 can inhibit the function of ROR2 and should have activity in mitigating the risk of metastases in patients with tumor cells that express ROR2.

Figure 12A:
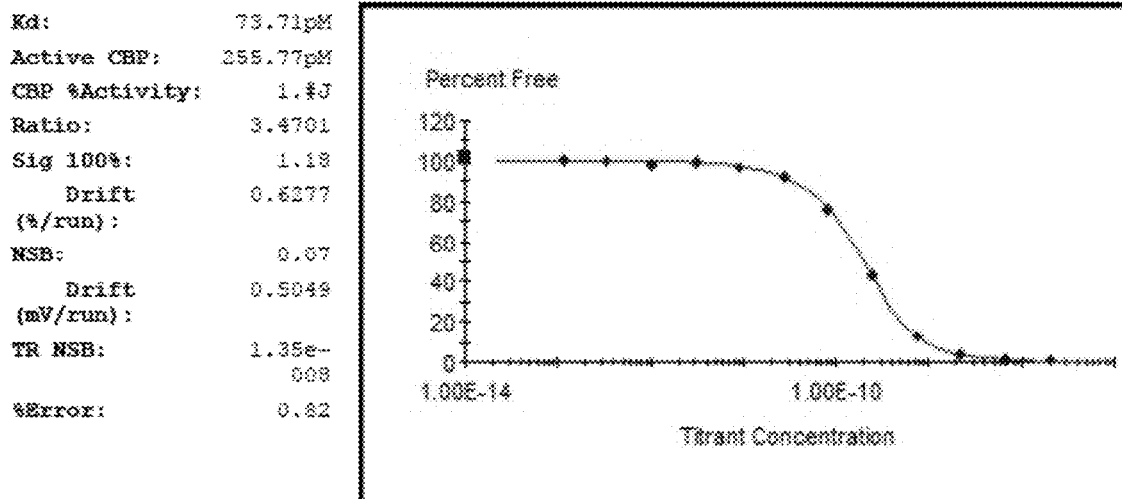
FIGS. 12A and 12B. Affinity measurement and binding specificity of the 6E6 single chain variable fragment (scFv) for human ROR2. Analysis was performed using a KinExA 3200 instrument.
Figure 12B:
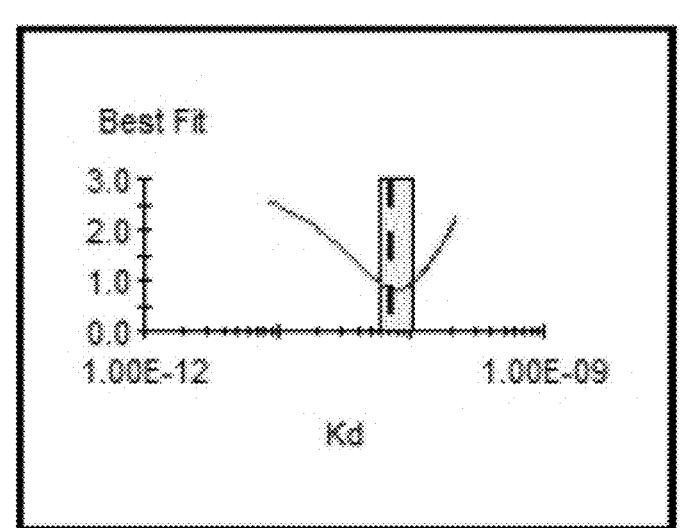
Figure 12C:
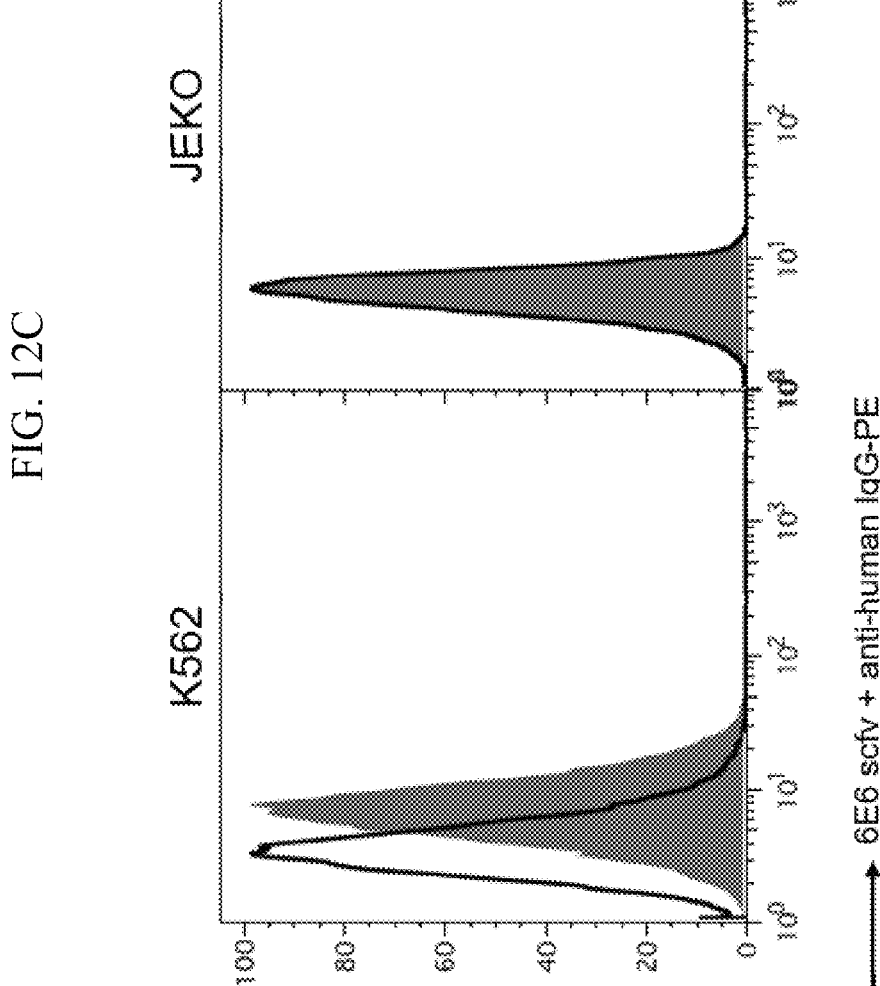
(FIG. 12C) Binding of the 6E6 scFv to ROR2 was assessed by flow cytometric staining and analysis of K562 (ROR2 positive) and JEKO (ROR2 negative) cells. Cells were stained on ice for 20 minutes with ~1 μg/ml of 6E6 anti-human ROR2 scfv, washed, stained for an additional 20 minutes on ice with phycoerythrin (PE)-conjugated anti-human IgG1 antibody, washed and analyzed by flow cytometry. Shaded histograms depict the relative fluorescence intensity (x axis) of viable cells, as determined by light scatter characteristics, stained with 6E6 scfv compared to viable cells stained with the anti-human IgG1-PE antibody only (open histograms). The 6E6 scFv binds to K562 cells, but not JEKO cells that do not express human ROR2.

Applicants have generated single chain Fv (scFv) by combing the variable regions of the light and heavy chains of 6E6 or 4G9 onto the constant regions (CH2-CH3) of human IgG1. The variable regions of these single chain constructs include linker sequences conjoining the light and heavy variable regions of both antibodies. Applicants found that scFv for 6E6 or 4G9 bind to the ROR2 antigen by ELISA and can bind specifically to cells that express the ROR2 surface antigen (FIG. 12). Therefore, the 6E6 or 4G9 scFv retain their specificity and binding activity for the target antigen. Such scFv's also may be used to generate bispecific antibodies that conjoin the scFv of 6E6 or 4G9 with another scFv, such as the scFv that recognizes a surface antigen expressed by T cells (e.g. CD3). These chimeric bispecific molecules may be used for cellular immune activation for the purpose of killing ROR2-expressing cells in patients treated with such bispecific antibodies.

Figure 13:
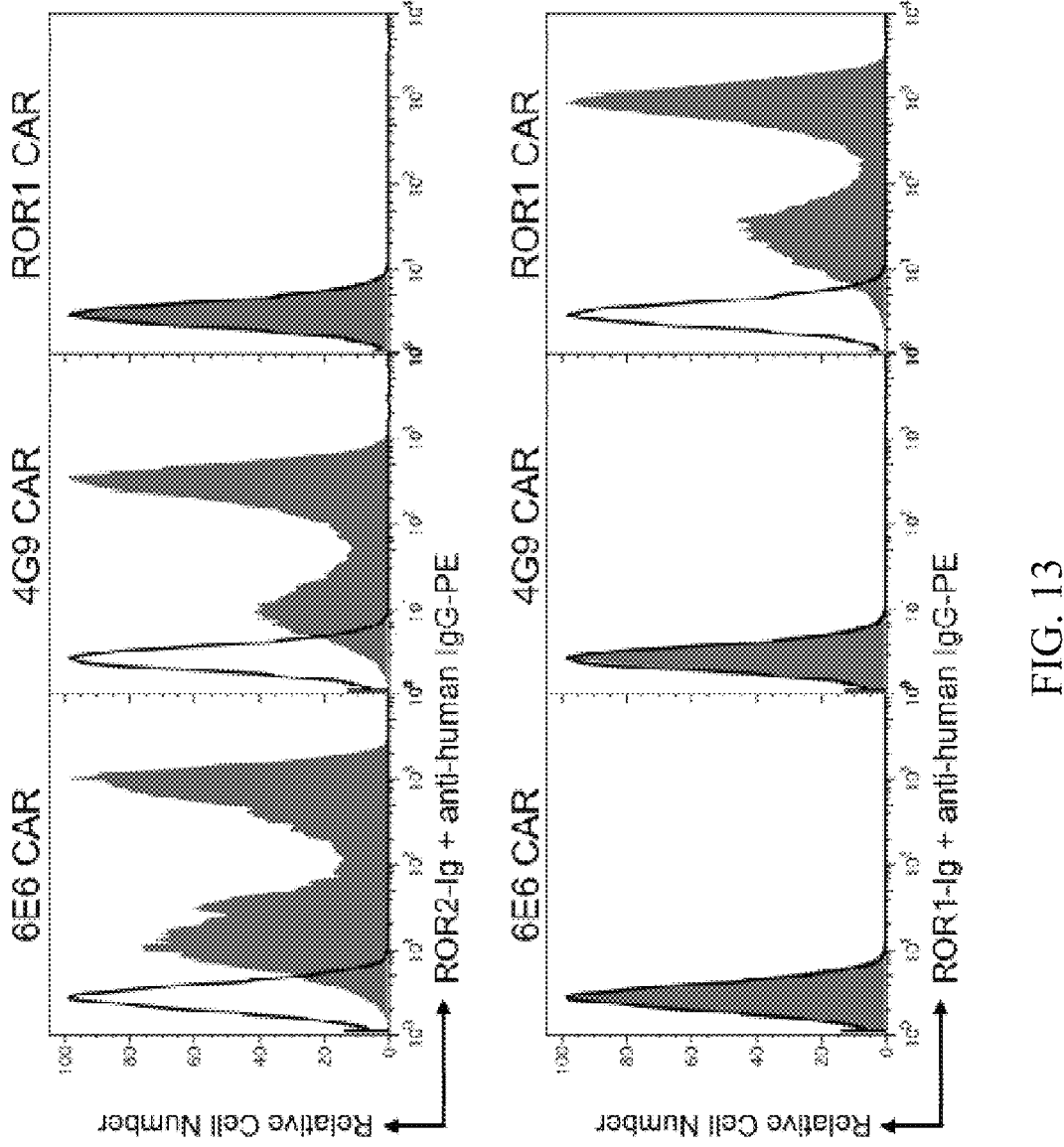
FIG. 13. 6E6 and 4G9 anti-human ROR2 chimeric antigen receptors (CAR) bind specifically to recombinant human ROR2 protein. HEK293 cells were transfected with either a 6E6 or 4G9 anti-human ROR2 chimeric antigen receptor construct or an anti-human ROR1 CAR construct. All cells were assessed after 48 hours by flow cytometry for binding of recombinant human ROR2-Ig protein comprised of the ROR2 extracellular domain and the CH2-CH3 constant region domains of human IgG1. Cells were stained on ice for 20 minutes with 1 μg/ml of recombinant ROR2-Ig (upper panel) or 1 ug/ml of control ROR1-Ig (lower panel), washed, stained for an additional 20 minutes on ice with phycoerythrin (PE)-conjugated anti-human IgG1 antibody, washed and analyzed by flow cytometry. Shaded histograms depict the relative fluorescence intensity (x axis) of viable cells, as determined by light scatter characteristics, stained with either ROR2-Ig or ROR1-Ig compared to cells stained with the anti-human IgG1-PE antibody only (open histograms). HEK293 cells transfected with either 6E6 or 4G9 CAR constructs bind ROR2-Ig (upper panels), but not ROR1-Ig, which is comprised of the same human IgG domains fused to the extracellular region of human ROR1. Conversely, ROR1 CAR transfected cells bind only to ROR1-Ig.

The capacity of the scFv to bind with high specificity and affinity to the ROR2 protein allows for the generation of chimeric antigen receptors (CARs) that can be transduced into T cells or NK cells for generation of cytotoxic effector cells capable of specifically killing cells that express the ROR2 surface antigen. Applicants have generated CAR constructs using the variable region sequences of either the 6E6 or 4G9 scFv. Applicants find that transfection of cells with these constructs can generate cells that express surface CAR that bind to the extracellular domain of ROR2. To demonstrate this Applicants generated a recombinant protein called ROR2-Ig, which is comprised of the ROR2 extracellular domain and the CH2-CH3 constant region domains of human IgG1. Applicants also generated a recombinant protein calls ROR1-Ig, comprised of the extracellular domain of ROR1 and the CH2-CH3 constant region domains of human IgG1. This allows for isolation of soluble proteins with the extracellular domain of either ROR2 or ROR1. Applicants found that cells transfected with the ROR2-CAR constructs generated from the scFv of either 6E6 or 4G9 can bind specifically to the ROR2-Ig, but not the highly related ROR1-Ig, demonstrating the specificity of this interaction (FIG. 13). Therefore, the scFv with sequences generated from 6E6 or 4G9, or their humanized counterparts, may be used to generate ROR2-specific CAR T cells or CAR NK cells that are specifically cytotoxic for ROR2-expressing cells.

Based on these preclinical findings, Applicants believe that these anti-human ROR2 mAb have high affinity and specificity for human ROR2 and could be used to target ROR2 in various human cancers.

EMBODIMENTS

Embodiment 1. An anti-tyrosine kinase-like orphan receptor 2 (ROR2) antibody comprising a heavy chain variable domain and a light chain variable domain, wherein said heavy chain variable domain comprises: a CDR H1 as set forth in SEQ ID NO:25, a CDR H2 as set forth in SEQ ID NO:26 and a CDR H3 as set forth in SEQ ID NO:27; and wherein said light chain variable domain comprises: a CDR L1 as set forth in SEQ ID NO:28, a CDR L2 as set forth in SEQ ID NO:29, and a CDR L3 as set forth in SEQ ID NO:30.

Embodiment 2. The antibody of embodiment 1, wherein said heavy chain variable domain comprises the sequence of SEQ ID NO:2.

Embodiment 3. The antibody of embodiment 1 or 2, wherein said light chain variable domain comprises the sequence of SEQ ID NO:4.

Embodiment 4. The antibody of any one of embodiments 1 to 3, wherein said antibody is a humanized antibody.

Embodiment 5. The antibody of any one of embodiments 1 to 4, wherein said antibody is a Fab' fragment.

Embodiment 6. The antibody of any one of embodiments 1 to 4, wherein said antibody is a single chain antibody (scFv).

Embodiment 7. The antibody of any one of embodiments 1 to 3, wherein said antibody is a chimeric antibody.

Embodiment 8. The antibody of any one of embodiments 1 to 4, wherein said antibody is an IgG.

Embodiment 9. The antibody of any one of embodiments 1 to 4 or 8, wherein said antibody is an IgG1 or an IgG2.

Embodiment 10. The antibody of any one of embodiments 1 to 9, wherein said antibody is capable of binding a ROR2 protein.

Embodiment 11. The antibody of embodiment 10, wherein said ROR2 protein comprises the amino acid sequence of SEQ ID NO:18.

Embodiment 12. The antibody of embodiment 10 or 11, wherein said antibody is capable of binding the extracellular domain of said ROR2 protein.

Embodiment 13. The antibody of embodiment 12, wherein said extracellular domain comprises the amino acid sequence of SEQ ID NO:22.

Embodiment 14. The antibody of embodiment 12, wherein said extracellular domain is a Kringle domain.

Embodiment 15. The antibody of any one of embodiments 10 to 14, wherein said ROR2 protein comprises a histidine at a position corresponding to position 349 or an aspartic acid at a position corresponding to position 354 of SEQ ID NO:22.

Embodiment 16. The antibody of any one of embodiments 10 to 15, wherein said ROR2 protein is expressed on a cell.

Embodiment 17. The antibody of embodiment 16, wherein said cell is a cancer cell.

Embodiment 18. The antibody of embodiment 17, wherein said cancer cell is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell.

Embodiment 19. The antibody of any one of embodiments 10 to 18, wherein said antibody is capable of binding said ROR2 protein with an equilibrium dissociation constant ($K_D$) from about 0.01 nM to about 1 nM.

Embodiment 20. The antibody of any one of embodiments 10 to 19, wherein said antibody is capable of binding said ROR2 protein with an equilibrium dissociation constant ($K_D$) of about 0.06 nM.

Embodiment 21. The antibody of any one of embodiments 1 to 20, wherein said antibody is attached to a therapeutic agent.

Embodiment 22. The antibody of any one of embodiments 1 to 20, wherein said antibody is attached to a diagnostic agent.

Embodiment 23. An anti-tyrosine kinase-like orphan receptor 2 (ROR2) antibody comprising a heavy chain variable domain and a light chain variable domain, wherein said heavy chain variable domain comprises: a CDR H1 as set forth in SEQ ID NO:31, a CDR H2 as set forth in SEQ ID NO:32 and a CDR H3 as set forth in SEQ ID NO:33; and wherein said light chain variable domain comprises: a CDR L1 as set forth in SEQ ID NO:34, a CDR L2 as set forth in SEQ ID NO:35, and a CDR L3 as set forth in SEQ ID NO:36.

Embodiment 24. The antibody of embodiment 23, wherein said heavy chain variable domain comprises the sequence of SEQ ID NO:6.

Embodiment 25. The antibody of embodiment 23 or 24, wherein said light chain variable domain comprises the sequence of SEQ ID NO:8.

Embodiment 26. The antibody of any one of embodiments 23 to 25, wherein said antibody is a humanized antibody.

Embodiment 27. The antibody of any one of embodiments 23 to 26, wherein said antibody is a Fab' fragment.

Embodiment 28. The antibody of any one of embodiments 23 to 26, wherein said antibody is a single chain antibody (scFv).

Embodiment 29. The antibody of any one of embodiments 23 to 25, wherein said antibody is a chimeric antibody.

Embodiment 30. The antibody of any one of embodiments 23 to 26, wherein said antibody is an IgG.

Embodiment 31. The antibody of any one of embodiments 23 to 26 or 30, wherein said antibody is an IgG1 or an IgG2.

Embodiment 32. The antibody of any one of embodiments 23 to 31, wherein said antibody is capable of binding a ROR2 protein comprising the amino acid sequence of SEQ ID NO:18.

Embodiment 33. The antibody of embodiment 32, wherein said antibody is capable of binding an extracellular domain of said ROR2 protein.

Embodiment 34. The antibody of embodiment 33, wherein said extracellular domain comprises the amino acid sequence of SEQ ID NO:22.

Embodiment 35. The antibody of embodiment 33, wherein said extracellular domain is an Ig-like domain.

Embodiment 36. The antibody of any one of embodiments 32 to 35, wherein said ROR2 protein comprises a methionine at a position corresponding to position 386 of SEQ ID NO:22.

Embodiment 37. The antibody of any one of embodiments 32 to 36, wherein said ROR2 protein is expressed on a cell.

Embodiment 38. The antibody of embodiment 37, wherein said cell is a cancer cell.

Embodiment 39. The antibody of embodiment 38, wherein said cancer cell is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell.

Embodiment 40. The antibody of any one of embodiments 32 to 39, wherein said antibody is capable of binding said ROR2 protein with an equilibrium dissociation constant ($K_D$) from about 0.2 nM to about 5 nM.

Embodiment 41. The antibody of any one of embodiments 32 to 40, wherein said antibody is capable of binding a ROR2 protein with an equilibrium dissociation constant ($K_D$) of about 1.9 nM.

Embodiment 42. The antibody of any one of embodiments 23 to 41, wherein said antibody is conjugated to a therapeutic agent.

Embodiment 43. The antibody of any one of embodiments 23 to 41, wherein said antibody is conjugated to a diagnostic agent.

Embodiment 44. An anti-tyrosine kinase-like orphan receptor 2 (ROR2) antibody comprising a heavy chain variable domain and a light chain variable domain, wherein said heavy chain variable domain comprises: a CDR H1 as set forth in SEQ ID NO:37, a CDR H2 as set forth in SEQ ID NO:38 and a CDR H3 as set forth in SEQ ID NO:39; and wherein said light chain variable domain comprises: a CDR L1 as set forth in SEQ ID NO:40, a CDR L2 as set forth in SEQ ID NO:41, and a CDR L3 as set forth in SEQ ID NO:42.

Embodiment 45. The antibody of embodiment 44, wherein said heavy chain variable domain comprises the sequence of SEQ ID NO:10.

Embodiment 46. The antibody of embodiment 44 or 45, wherein said light chain variable domain comprises the sequence of SEQ ID NO:12.

Embodiment 47. The antibody of any one of embodiments 44 to 46, wherein said antibody is a humanized antibody.

Embodiment 48. The antibody of any one of embodiments 44 to 47, wherein said antibody is a Fab' fragment.

Embodiment 49. The antibody of any one of embodiments 44 to 47, wherein said antibody is a single chain antibody (scFv).

Embodiment 50. The antibody of any one of embodiments 44 to 46, wherein said antibody is a chimeric antibody.

Embodiment 51. The antibody of any one of embodiments 44 to 47, wherein said antibody is an IgG.

Embodiment 52. The antibody of any one of embodiments 44 to 47 or 51, wherein said antibody is an IgG1.

Embodiment 53. The antibody of any one of embodiments 44 to 52, wherein said antibody is capable of binding a ROR2 protein comprising the amino acid sequence of SEQ ID NO:18.

Embodiment 54. The antibody of embodiment 53, wherein said antibody is capable of binding an extracellular domain of a ROR2 protein.

Embodiment 55. The antibody of embodiment 54, wherein said extracellular domain comprises the amino acid sequence of SEQ ID NO:22.

Embodiment 56. The antibody of embodiment 54, wherein said wherein said extracellular domain is a Kringle domain.

Embodiment 57. The antibody of any one of embodiments 53 to 56, wherein said ROR2 protein comprises a histidine at a position corresponding to position 349, an aspartic acid at a position corresponding to position 354, or a methionine at a position corresponding to position 386 of SEQ ID NO:22.

Embodiment 58. The antibody of any one of embodiments 43 to 57, wherein said ROR2 protein is expressed on a cell.

Embodiment 59. The antibody of embodiment 58, wherein said cell is a cancer cell.

Embodiment 60. The antibody of embodiment 59, wherein said cancer cell is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell.

Embodiment 61. The antibody of any one of embodiments 44 to 50, wherein said antibody is capable of binding said ROR2 protein with an equilibrium dissociation constant ($K_D$) from about 10 nM to about 150 nM.

Embodiment 62. The antibody of any one of embodiments 44 to 61, wherein said antibody is conjugated to a therapeutic agent.

Embodiment 63. The antibody of any one of embodiments 44 to 61, wherein said antibody is conjugated to a diagnostic agent.

Embodiment 64. An anti-tyrosine kinase-like orphan receptor 2 (ROR2) antibody comprising a heavy chain variable domain and a light chain variable domain, wherein said heavy chain variable domain comprises: a CDR H1 as set forth in SEQ ID NO:43, a CDR H2 as set forth in SEQ ID NO:44 and a CDR H3 as set forth in SEQ ID NO:45; and wherein said light chain variable domain comprises: a CDR L1 as set forth in SEQ ID NO:46, a CDR L2 as set forth in SEQ ID NO:47, and a CDR L3 as set forth in SEQ ID NO:48.

Embodiment 65. The antibody of embodiment 64, wherein said heavy chain variable domain comprises the sequence of SEQ ID NO:14.

Embodiment 66. The antibody of embodiment 64 or 65, wherein said light chain variable domain comprises the sequence of SEQ ID NO:16.

Embodiment 67. The antibody of any one of embodiments 64 to 66, wherein said antibody is a humanized antibody.

Embodiment 68. The antibody of any one of embodiments 64 to 67, wherein said antibody is a Fab' fragment.

Embodiment 69. The antibody of any one of embodiments 64 to 67, wherein said antibody is a single chain antibody (scFv).

Embodiment 70. The antibody of any one of embodiments 64 to 66, wherein said antibody is a chimeric antibody.

Embodiment 71. The antibody of any one of embodiments 64 to 67, wherein said antibody is an IgG.

Embodiment 72. The antibody of any one of embodiments 64 to 66 or 71, wherein said antibody is an IgG1.

Embodiment 73. The antibody of any one of embodiments 64 to 67, wherein said antibody is capable of binding a ROR2 protein comprising the amino acid sequence of SEQ ID NO:18.

Embodiment 74. The antibody of embodiment 73, wherein said antibody is capable of binding an extracellular domain of said ROR2 protein.

Embodiment 75. The antibody of embodiments 74, wherein said extracellular domain comprises the amino acid sequence of SEQ ID NO:22.

Embodiment 76. The antibody of embodiment 72, wherein said extracellular domain is an Ig-like domain.

Embodiment 77. The antibody of any one of embodiments 74 to 76, wherein said ROR2 protein is expressed on a cell.

Embodiment 78. The antibody of embodiment 77, wherein said cell is a cancer cell.

Embodiment 79. The antibody of embodiment 78, wherein said cancer cell is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell.

Embodiment 80. The antibody of any one of embodiments 64 to 79, wherein said antibody is capable of binding said ROR2 protein with an equilibrium dissociation constant ($K_D$) from about 10 nM to about 150 nM.

Embodiment 81. The antibody of any one of embodiments 64 to 80, wherein said antibody is conjugated to a therapeutic agent.

Embodiment 82. The antibody of any one of embodiments 64 to 80, wherein said antibody is conjugated to a diagnostic agent.

Embodiment 83. A method of treating cancer in a subject in need thereof, said method comprising administering to a subject a therapeutically effective amount of an antibody of any one of embodiments 1 to 82.

Embodiment 84. A method of inhibiting metastasis of a ROR2 expressing cancer in a subject in need thereof, said method comprising administering to a subject a therapeutically effective amount of an antibody of any one of embodiments 1 to 82.

Embodiment 85. The method of embodiments 83 or 84, wherein said cancer is breast cancer, ovarian cancer, pancreatic cancer, cervical cancer, gastric cancer, renal cancer, head and neck cancer, bone cancer, skin cancer or prostate cancer.

Embodiment 86. A method of detecting a ROR2 expressing cell, said method comprising (i) contacting a ROR2-expressing cell with an antibody of any one of embodiments 1 to 82; and (ii) detecting binding of said antibody to a ROR2 protein expressed by said cell.

Embodiment 87. The method of embodiment 86, wherein said antibody is attached to a detectable moiety.

Embodiment 88. The method of embodiment 86 or 87, wherein said ROR2-expressing cell is in a subject.

Embodiment 89. The method of embodiment 88, wherein said subject is a subject having cancer.

Embodiment 90. The method of embodiment 89, wherein said cancer is cancer is breast cancer, ovarian cancer, pancreatic cancer, cervical cancer, gastric cancer, renal cancer, head and neck cancer, bone cancer, skin cancer or prostate cancer.

Embodiment 91. The method of embodiment 86 or 87, wherein said contacting occurs in vitro.

Embodiment 92. A method of delivering a therapeutic agent to a ROR2 expressing cell, said method comprising contacting a ROR2 expressing cell with an antibody of any one of embodiments 1-82, wherein said antibody is attached to a therapeutic agent.

Embodiment 93. The method of embodiment 92, wherein said therapeutic agent is an anti-cancer agent.

Embodiment 94. The method of embodiment 92 or 93, wherein said ROR2-expressing cell is in a subject.

Embodiment 95. The method of embodiment 94, wherein said subject is a subject having cancer.

Embodiment 96. The method of embodiment 95, wherein said cancer is cancer is breast cancer, ovarian cancer, pancreatic cancer, cervical cancer, gastric cancer, renal cancer, head and neck cancer, bone cancer, skin cancer or prostate cancer.

Embodiment 97. The method of embodiment 93 or 94, wherein said contacting occurs in vitro.

Embodiment 98. A method of inhibiting migration of a ROR2-expressing cell, said method comprising contacting a ROR2 expressing cell with an antibody of any one of embodiments 1-80.

Embodiment 99. The method of embodiment 98, wherein said ROR2 expressing cell is in a subject having cancer.

Embodiment 100. The method of embodiment 99, wherein said cancer is cancer is breast cancer, ovarian cancer, pancreatic cancer, cervical cancer, gastric cancer, renal cancer, head and neck cancer, bone cancer, skin cancer or prostate cancer.

Embodiment 101. The method of embodiment 98, wherein said contacting occurs in vitro.

Embodiment 102. The method of any one of embodiments 86 to 101, wherein said ROR2 expressing cell is a cancer cell.

Embodiment 103. The method of embodiment 102, wherein said cancer cell is a breast cancer cell, ovarian cancer cell, pancreatic cancer cell, cervical cancer cell, gastric cancer cell, renal cancer cell, head and neck cancer cell, bone cancer cell, skin cancer cell or prostate cancer cell.

Embodiment 104. An anti-ROR2 antibody, wherein said anti-ROR2 antibody binds the same epitope as an anti-ROR2 antibody comprising a heavy chain variable domain comprising: a CDR H1 as set forth in SEQ ID NO:25, a CDR H2 as set forth in SEQ ID NO:26 and a CDR H3 as set forth in SEQ ID NO:27; and a light chain variable domain comprising: a CDR L1 as set forth in SEQ ID NO:28, a CDR L2 as set forth in SEQ ID NO:29, and a CDR L3 as set forth in SEQ ID NO:30

Embodiment 105. An anti-ROR2 antibody, wherein said anti-ROR2 antibody binds the same epitope as an anti-ROR2 antibody comprising a heavy chain variable domain of SEQ ID:2; and a light chain variable domain of SEQ ID NO:4.

Embodiment 106. An anti-ROR2 antibody, wherein said anti-ROR2 antibody binds the same epitope as an anti-ROR2 antibody comprising a heavy chain variable domain encoded by the nucleic acid sequence of SEQ ID:1; and a light chain variable domain encoded by the nucleic acid sequence of SEQ ID:3.

Embodiment 107. An anti-ROR2 antibody, wherein said anti-ROR2 antibody binds the same epitope as an anti-ROR2 antibody comprising a heavy chain variable domain comprising: a CDR H1 as set forth in SEQ ID NO:31, a CDR H2 as set forth in SEQ ID NO:32 and a CDR H3 as set forth in SEQ ID NO:33; and a light chain variable domain comprising: a CDR L1 as set forth in SEQ ID NO:34, a CDR L2 as set forth in SEQ ID NO:35, and a CDR L3 as set forth in SEQ ID NO:36.

Embodiment 108. An anti-ROR2 antibody, wherein said anti-ROR2 antibody binds the same epitope as an anti-ROR2 antibody comprising a heavy chain variable domain of SEQ ID:6; and a light chain variable domain of SEQ ID NO:8.

Embodiment 109. An anti-ROR2 antibody, wherein said anti-ROR2 antibody binds the same epitope as an anti-ROR2 antibody comprising a heavy chain variable domain encoded by the nucleic acid sequence of SEQ ID:5; and a light chain variable domain encoded by the nucleic acid sequence of SEQ ID:7.

Embodiment 110. An anti-ROR2 antibody, wherein said anti-ROR2 antibody binds the same epitope as an anti-ROR2 antibody comprising a heavy chain variable domain comprising: a CDR H1 as set forth in SEQ ID NO:37, a CDR H2 as set forth in SEQ ID NO:38 and a CDR H3 as set forth in SEQ ID NO:39; and a light chain variable domain comprising: a CDR L1 as set forth in SEQ ID NO:40, a CDR L2 as set forth in SEQ ID NO:41, and a CDR L3 as set forth in SEQ ID NO:42

Embodiment 111. An anti-ROR2 antibody, wherein said anti-ROR2 antibody binds the same epitope as an anti-ROR2 antibody comprising a heavy chain variable domain of SEQ ID:10; and a light chain variable domain of SEQ ID NO:12.

Embodiment 112. An anti-ROR2 antibody, wherein said anti-ROR2 antibody binds the same epitope as an anti-ROR2 antibody comprising a heavy chain variable domain encoded by the nucleic acid sequence of SEQ ID:9; and a light chain variable domain encoded by the nucleic acid sequence of SEQ ID:11.

Embodiment 113. An anti-ROR2 antibody, wherein said anti-ROR2 antibody binds the same epitope as an anti-ROR2 antibody comprising a heavy chain variable domain comprising: a CDR H1 as set forth in SEQ ID NO:43, a CDR H2 as set forth in SEQ ID NO:44 and a CDR H3 as set forth in SEQ ID NO:45; and a light chain variable domain comprising: a CDR L1 as set forth in SEQ ID NO:46, a CDR L2 as set forth in SEQ ID NO:47, and a CDR L3 as set forth in SEQ ID NO:48.

Embodiment 114. An anti-ROR2 antibody, wherein said anti-ROR2 antibody binds the same epitope as an anti-ROR2 antibody comprising a heavy chain variable domain of SEQ ID:14; and a light chain variable domain of SEQ ID NO:16.

Embodiment 115. An anti-ROR2 antibody, wherein said anti-ROR2 antibody binds the same epitope as an anti-ROR2 antibody comprising a heavy chain variable domain encoded by the nucleic acid sequence of SEQ ID:13; and a light chain variable domain encoded by the nucleic acid sequence of SEQ ID:15.

Embodiment 116. A chimeric antigen receptor comprising: (i) an antibody region comprising: (a) a light chain variable domain comprising a CDR L1 as set forth in SEQ ID NO: 28, a CDR L2 as set forth in SEQ ID NO:29 and a CDR L3 as set forth in SEQ ID NO:30; and (b) a heavy chain variable region domain comprising a CDR H1 as set forth in SEQ ID NO:25, a CDR H2 as set forth in SEQ ID NO:26, and a CDR H3 as set forth in SEQ ID NO:27; and (ii) a transmembrane domain.

Embodiment 117. A chimeric antigen receptor comprising: (i) an antibody region comprising: (a) a light chain variable domain comprising a CDR L1 as set forth in SEQ ID NO:34, a CDR L2 as set forth in SEQ ID NO:35 and a CDR L3 as set forth in SEQ ID NO:36; and (b) a heavy chain variable region domain comprising a CDR H1 as set forth in SEQ ID NO:31, a CDR H2 as set forth in SEQ ID NO:32, and a CDR H3 as set forth in SEQ ID NO:33; and (ii) a transmembrane domain.

Embodiment 118. A chimeric antigen receptor comprising: (i) an antibody region comprising: (a) a light chain variable domain comprising a CDR L1 as set forth in SEQ ID NO:40, a CDR L2 as set forth in SEQ ID NO:41 and a CDR L3 as set forth in SEQ ID NO:42; and (b) a heavy chain variable region domain comprising a CDR H1 as set forth in SEQ ID NO:37, a CDR H2 as set forth in SEQ ID NO:38, and a CDR H3 as set forth in SEQ ID NO:39; and (ii) a transmembrane domain Embodiment 119. A chimeric antigen receptor comprising: (i) an antibody region comprising: (a) a light chain variable domain comprising a CDR L1 as set forth in SEQ ID NO:46, a CDR L2 as set forth in SEQ ID NO:47 and a CDR L3 as set forth in SEQ ID NO:48; and (b) a heavy chain variable region domain comprising a CDR H1 as set forth in SEQ ID NO:43, a CDR H2 as set forth in SEQ ID NO:44, and a CDR H3 as set forth in SEQ ID NO:45; and (ii) a transmembrane domain.

Embodiment 120. The chimeric antigen receptor of any one of embodiments 116 to 119, further comprising an intracellular T-cell signaling domain.

Embodiment 121. The chimeric antigen receptor of embodiments 116 to 120, wherein the intracellular T-cell signaling domain is a CD3 (intracellular T-cell signaling domain.

Embodiment 122. The chimeric antigen receptor of any one of embodiments 116 to 121, further comprising an intracellular co-stimulatory T-cell signaling domain.

Embodiment 123. The chimeric antigen receptor of embodiment 122, wherein said intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain.

Embodiment 124. The chimeric antigen receptor of any one of embodiments 116 to 123, further comprising a spacer region.

Embodiment 125. The chimeric antigen receptor of embodiment 124, wherein the spacer region further comprises a hinge region.

Embodiment 126. The chimeric antigen receptor of any one of embodiments 116 to 125, further comprising a linker domain.

Embodiment 127. The chimeric antigen receptor of any one of embodiments 116 to 126, further comprising a heavy chain constant domain.

Embodiment 128. A method of treating cancer in a subject in need thereof said method comprising, administering a therapeutically effective amount of a chimeric antigen receptor of any one of embodiments 116 to 127 to a subject.

Embodiment 129. The method of embodiment 126, wherein said cancer is cancer is breast cancer, ovarian cancer, pancreatic cancer, cervical cancer, gastric cancer, renal cancer, head and neck cancer, bone cancer, skin cancer or prostate cancer.

What is claimed is:

1. An anti-tyrosine kinase-like orphan receptor 2 (ROR2) antibody comprising a heavy chain variable domain and a light chain variable domain, wherein said heavy chain variable domain comprises:
 a CDR H1 as set forth in SEQ ID NO:25, a CDR H2 as set forth in SEQ ID NO:26 and a CDR H3 as set forth in SEQ ID NO:27; and
wherein said light chain variable domain comprises:
 a CDR L1 as set forth in SEQ ID NO:28, a CDR L2 as set forth in SEQ ID NO:29, and a CDR L3 as set forth in SEQ ID NO:30.

2. An anti-tyrosine kinase-like orphan receptor 2 (ROR2) antibody comprising a heavy chain variable domain and a light chain variable domain, wherein said heavy chain variable domain comprises:
 a CDR H1 as set forth in SEQ ID NO:31, a CDR H2 as set forth in SEQ ID NO:32 and a CDR H3 as set forth in SEQ ID NO:33; and
wherein said light chain variable domain comprises:
 a CDR L1 as set forth in SEQ ID NO:34, a CDR L2 as set forth in SEQ ID NO:35, and a CDR L3 as set forth in SEQ ID NO:36.

3. An anti-tyrosine kinase-like orphan receptor 2 (ROR2) antibody comprising a heavy chain variable domain and a light chain variable domain, wherein said heavy chain variable domain comprises:
 a CDR H1 as set forth in SEQ ID NO:37, a CDR H2 as set forth in SEQ ID NO:38 and a CDR H3 as set forth in SEQ ID NO:39; and wherein said light chain variable domain comprises:
a CDR L1 as set forth in SEQ ID NO:40, a CDR L2 as set forth in SEQ ID NO:41, and a CDR L3 as set forth in SEQ ID NO:42.

4. An anti-tyrosine kinase-like orphan receptor 2 (ROR2) antibody comprising a heavy chain variable domain and a light chain variable domain,
wherein said heavy chain variable domain comprises:
a CDR H1 as set forth in SEQ ID NO:43, a CDR H2 as set forth in SEQ ID NO:44 and a CDR H3 as set forth in SEQ ID NO:45; and
wherein said light chain variable domain comprises:
a CDR L1 as set forth in SEQ ID NO:46, a CDR L2 as set forth in SEQ ID NO:47, and a CDR L3 as set forth in SEQ ID NO:48.

5. A method of treating cancer in a subject in need thereof, said method comprising administering to a subject a therapeutically effective amount of an antibody of any one of claim 1, 2, 3 or 4.

6. A method of detecting a ROR2 expressing cell, said method comprising
(i) contacting a ROR2-expressing cell with an antibody of any one of claim 1, 2, 3 or 4 and
(ii) detecting binding of said antibody to a ROR2 protein expressed by said cell.

7. A method of delivering a therapeutic agent to a ROR2 expressing cell, said method comprising contacting a ROR2 expressing cell with an antibody of any one of claim 1, 2, 3 or 4, wherein said antibody is attached to a therapeutic agent.

8. A method of inhibiting migration of a ROR2-expressing cell, said method comprising contacting a ROR2 expressing cell with an antibody of any one of claims 1, 2, 3 or 4.

9. A chimeric antigen receptor comprising:
(i) an antibody region comprising:
(a) a light chain variable domain comprising a CDR L1 as set forth in SEQ ID NO: 28, a CDR L2 as set forth in SEQ ID NO:29 and a CDR L3 as set forth in SEQ ID NO:30; and
(b) a heavy chain variable region domain comprising a CDR H1 as set forth in SEQ ID NO:25, a CDR H2 as set forth in SEQ ID NO:26, and a CDR H3 as set forth in SEQ ID NO:27; and
(ii) a transmembrane domain.

10. A chimeric antigen receptor comprising:
(i) an antibody region comprising:
(a) a light chain variable domain comprising a CDR L1 as set forth in SEQ ID NO:34, a CDR L2 as set forth in SEQ ID NO:35 and a CDR L3 as set forth in SEQ ID NO:36; and
(b) a heavy chain variable region domain comprising a CDR H1 as set forth in SEQ ID NO:31, a CDR H2 as set forth in SEQ ID NO:32, and a CDR H3 as set forth in SEQ ID NO:33; and
(ii) a transmembrane domain.

11. A chimeric antigen receptor comprising:
(i) an antibody region comprising:
(a) a light chain variable domain comprising a CDR L1 as set forth in SEQ ID NO:40, a CDR L2 as set forth in SEQ ID NO:41 and a CDR L3 as set forth in SEQ ID NO:42; and
(b) a heavy chain variable region domain comprising a CDR H1 as set forth in SEQ ID NO:37, a CDR H2 as set forth in SEQ ID NO:38, and a CDR H3 as set forth in SEQ ID NO:39; and
(ii) a transmembrane domain.

12. A chimeric antigen receptor comprising:
(i) an antibody region comprising:
(a) a light chain variable domain comprising a CDR L1 as set forth in SEQ ID NO:46, a CDR L2 as set forth in SEQ ID NO:47 and a CDR L3 as set forth in SEQ ID NO:48; and
(b) a heavy chain variable region domain comprising a CDR H1 as set forth in SEQ ID NO:43, a CDR H2 as set forth in SEQ ID NO:44, and a CDR H3 as set forth in SEQ ID NO:45; and
(ii) a transmembrane domain.

13. A method of treating cancer in a subject in need thereof said method comprising, administering a therapeutically effective amount of a chimeric antigen receptor of any one of claims 9, 10, 11 or 12 to a subject.

* * * * *

SEQUENCE LISTING

<160> NUMBER OF SEQ ID NOS: 122

<210> SEQ ID NO 1
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 1
gaggtgcagc tggtggagtc tggggggagac ttagtgaagc ctggagggtc cctgaaactc      60
tcctgtgcag cctctggatt cactttcagt aattatggca tgtcttgggt tcgccagact     120
ccagacaaga ggctggagtg ggtcgcaacc attagtagtg gtggtggtta cactcactat     180
gtagacagtg tgaaggggcg attcaccatt tccagagaca atgccaacca tatcctgtac     240
ctgcaaatga gcagtctgaa ctctgaggac acagccatgt attattgtgc aagacacccg     300
agggattttt cctatgctat ggactactgg ggtcagggaa cctcagtcac cgtctcctca     360

<210> SEQ ID NO 2
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 2

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Gly Tyr Thr His Tyr Val Asp Ser Val
    50                  55                  60

Lys Gly Arg Phe Thr Ile Ser Arg Asp Asn Ala Asn His Ile Leu Tyr
65                  70                  75                  80

Leu Gln Met Ser Ser Leu Asn Ser Glu Asp Thr Ala Met Tyr Tyr Cys
                85                  90                  95

Ala Arg His Pro Arg Asp Phe Ser Tyr Ala Met Asp Tyr Trp Gly Gln
            100                 105                 110

Gly Thr Ser Val Thr Val Ser Ser
        115                 120

<210> SEQ ID NO 3
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 3
gacattgtga tgacccagtc tcacaaattc atgtccacat caataggaga cagggtcagc      60
atcacctgca aggccagtca ggatgtgggt cattatgtgg cctggtatca acagaaacca     120
ggtcaatctc ctaaactact gatttactgg gcatccaccc ggcacactgg agtccctgat     180
cgcttcacag gtagtggatc tgggacagat ttcactctca ccattagcaa tgtgcagtct     240
gaagacttgg cagattattt ctgtcagcaa tataacatct atccgtggac gttcggtgga     300
ggctccaagc tggcaatcaa a                                              321

-continued

<210> SEQ ID NO 4
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 4

```
Asp Ile Val Met Thr Gln Ser His Lys Phe Met Ser Thr Ser Ile Gly
1               5                   10                  15

Asp Arg Val Ser Ile Thr Cys Lys Ala Ser Gln Asp Val Gly His Tyr
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ile Tyr Pro Trp
                85                  90                  95

Thr Phe Gly Gly Gly Ser Lys Leu Ala Ile Lys
            100                 105
```

<210> SEQ ID NO 5
<211> LENGTH: 357
<212> TYPE: DNA
<213> ORGANISM: Artificial Sequence
<220> FEATURE:
<223> OTHER INFORMATION: Synthetic polynucleotide

<400> SEQUENCE: 5

```
caggttcaac tgcaacagtc tggggctgag ctggtgaggc ctggggcttc agtgaagctg      60
tcctgcaagg ctttgggcta cacatttact gactatgaaa tgcactgggt gaagcagaca     120
cctgtgcatg gcctggaatg gattggagct attcatccag gaagtggtgg tactgcctat     180
aatcagaagt tcaagggcaa ggccacactg actgcagaca atcctccag cacagcctac     240 atggagctca gcaggctgac atctgaggac tctgctgtct attactgtac aagaaggagg     300
cctaggttct atggtatgga ctactggggt caaggaacct cagtcaccgt ctcctca        357
```

<210> SEQ ID NO 6
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 6

```
Gln Val Gln Leu Gln Gln Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile His Pro Gly Ser Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80
```

-continued

```
Met Glu Leu Ser Arg Leu Thr Ser Glu Asp Ser Ala Val Tyr Tyr Cys
                85              90              95

Thr Arg Arg Arg Pro Arg Phe Tyr Gly Met Asp Tyr Trp Gly Gln Gly
            100             105             110

Thr Ser Val Thr Val Ser Ser
        115
```

```
<210> SEQ ID NO 7
<211> LENGTH: 336
<212> TYPE: DNA
<213> ORGANISM: Artificial Sequence
<220> FEATURE:
<223> OTHER INFORMATION: Synthetic polynucleotide

<400> SEQUENCE: 7
gatattgtga tgactcaggc tgcaccctct gtacctgtca ctcctggaga gtcagtatcc      60
atctcctgca ggtctagtaa gagtctcctg catagtaatg gcaacactta cttgtattgg     120
ttcctgcaga ggccaggcca gtctcctcag ctcctgatat atcggatgtc caaccttgcc     180
tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ctcacggtcg gtgctgggac caagctggag ctgaaa                              336
```

```
<210> SEQ ID NO 8
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 8
```

```
Asp Ile Val Met Thr Gln Ala Ala Pro Ser Val Pro Val Thr Pro Gly
1               5               10              15

Glu Ser Val Ser Ile Ser Cys Arg Ser Ser Lys Ser Leu Leu His Ser
            20              25              30

Asn Gly Asn Thr Tyr Leu Tyr Trp Phe Leu Gln Arg Pro Gly Gln Ser
        35              40              45

Pro Gln Leu Leu Ile Tyr Arg Met Ser Asn Leu Ala Ser Gly Val Pro
    50              55              60

Asp Arg Phe Ser Gly Ser Gly Ser Gly Thr Ala Phe Thr Leu Arg Ile
65              70              75              80

Ser Arg Val Glu Ala Glu Asp Val Gly Val Tyr Tyr Cys Met Gln His
                85              90              95

Leu Glu Tyr Pro Leu Thr Val Gly Ala Gly Thr Lys Leu Glu Leu Lys
            100             105             110
```

```
<210> SEQ ID NO 9
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 9
gaggtgcagc tggtggagtc tggggggagac ttggtgaagc ctggagggtc cctgaaactc      60
tcctgtgcag cctctggatt cactttcagt aactatggca tgtcttgggt tcgccagact     120
ccagacaaga ggctggagtg ggtcgcaacc attagtagtg gtggtggttc cacctactat     180
ccagacagtg tgaaggggcg attcaccatc tccagagaca atgccaagaa ctccctgtac     240
```

-continued

```
ctgcaaatga gcagtctgaa gtctgaggac acagccatgt attactgtgc aagacatccc      300
tatgattacg ggtactactt tgactactgg ggccaaggca ccactctcac agtctcctca      360
```

<210> SEQ ID NO 10
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 10

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Lys Ser Glu Asp Thr Ala Met Tyr Tyr Cys
                85                  90                  95

Ala Arg His Pro Tyr Asp Tyr Gly Tyr Tyr Phe Asp Tyr Trp Gly Gln
            100                 105                 110

Gly Thr Thr Leu Thr Val Ser Ser
        115                 120
```

<210> SEQ ID NO 11
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 11

```
gacatcttgc tgactcagtc tccagacatc ctgtctgtga gtccaggaga aagagtcagt       60
ttctcctgca gggccagtca gagcattggc acaagcatac actggtatca gcagagaaca      120
aatggttctc caaggcttct cataaaatat gcttctgagt ctatctctgg gatcccttcc      180
aggtttagtg gcagtggatc agggacagat tttactctta gcatcaacag tgtggagtct      240
gaagatattg cagattatta ctgtcaacaa agtgatagct ggccattccc gttcggctcg      300
gggacaaaat tggaaaaaaa a                                                 321
```

<210> SEQ ID NO 12
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 12

```
Asp Ile Leu Leu Thr Gln Ser Pro Asp Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45
```

-continued

```
Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asp Ser Trp Pro Phe
                85                  90                  95

Pro Phe Gly Ser Gly Thr Lys Leu Glu Lys Lys
            100                 105
```

<210> SEQ ID NO 13
<211> LENGTH: 366
<212> TYPE: DNA
<213> ORGANISM: Artificial Sequence
<220> FEATURE:
<223> OTHER INFORMATION: Synthetic polynucleotide

<400> SEQUENCE: 13

```
gaggtgcagc ttgttgagtc tggtggagga ttggtgcagc ctaaagggtc attgaagctc      60
tcatgtgcag cctctggatt caccttcaat acctacgcca tgaactgggt ccgccaggct     120
ccaggaaagg gtttggaatg ggttgctcgc ataagaagta aaagtaataa ttatgcaaca     180
tattatgccg attcagtgaa agacaggttc accatctcca gagatgattc acaaagcatg     240
ctccatctgc aaatgaacaa cttgaaaact gaggacacag ccatgtatta ctgtgtgaga     300
cacggtagta gcctctacta tgctatggac tactggggtc aaggaacctc agtcaccgtc     360
tcctca                                                                366
```

<210> SEQ ID NO 14
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 14

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu His Leu Gln Met Asn Asn Leu Lys Thr Glu Asp Thr Ala Met Tyr
                85                  90                  95

Tyr Cys Val Arg His Gly Ser Ser Leu Tyr Tyr Ala Met Asp Tyr Trp
            100                 105                 110

Gly Gln Gly Thr Ser Val Thr Val Ser Ser
            115                 120
```

<210> SEQ ID NO 15
<211> LENGTH: 321
<212> TYPE: DNA
<213> ORGANISM: Artificial Sequence
<220> FEATURE:
<223> OTHER INFORMATION: Synthetic polynucleotide

```
<400> SEQUENCE: 15
gacatccaga tgacccagtc tccatcctcc ttatctgcct ctctgggaga aagagtcagt      60
ctcacttgtc gggcaagtca ggaaattagt ggttacttag gctggcttca gcagaaacca     120
gatggaacta ttaaacgcct gatctacgcc gcatccactt tagattctgg tgtcccaaaa     180
aggttcagtg gcagtaggtc tgggtcagct tattctctca ccatcagcag ccttgagtct     240
gaagattttg cagactatta ctgtctacaa tatgctagtt atccgtacac gttcggaggg     300
gggaccaagc tggaaataaa a                                                321

<210> SEQ ID NO 16
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 16

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Gly Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Ala Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile Lys
            100                 105

<210> SEQ ID NO 17
<211> LENGTH: 2832
<212> TYPE: DNA
<213> ORGANISM: Artificial Sequence
<220> FEATURE:
<223> OTHER INFORMATION: Synthetic polynucleotide

<400> SEQUENCE: 17
atggcccggg gctcggcgct cccgcggcgg ccgctgctgt gcatcccggc cgtctgggcg      60
gccgccgcgc ttctgctctc agtgtcccgg acttcaggtg aagtggaggt tctggatccg     120
aacgaccctt taggacccct tgatgggcag gacggcccga ttccaactct gaaaggttac     180
tttctgaatt ttctggagcc agtaaacaat atcaccattg tccaaggcca gacggcaatt     240
ctgcactgca aggtggcagg aaacccaccc cctaacgtgc ggtggctaaa gaatgatgcc     300
ccggtggtgc aggagccgcg gcggatcatc atccggaaga cagaatatgg ttcacgactg     360
cgaatccagg acctggacac gacagacact ggctactacc agtgcgtggc caccaacggg     420
atgaagacca ttaccgccac tggcgtcctg tttgtgcggc tgggtccaac gcacagccca     480
aatcataact tcaggatga ttaccacgag gatgggttct gccagcctta ccggggaatt     540
gcctgtgcac gcttcattgg caaccggacc atttatgtgg actcgcttca gatgcagggg     600
gagattgaaa accgaatcac agcggccttc accatgatcg gcacgtctac gcacctgtcg     660
gaccagtgct cacagttcgc catcccatcc ttctgccact cgtgtttcc tctgtgcgac     720
```

```
gcgcgctccc gggcacccaa gccgcgtgag ctgtgccgcg acgagtgcga ggtgctggag        780
agcgacctgt gccgccagga gtacaccatc gcccgctcca acccgctcat cctcatgcgg        840
cttcagctgc ccaagtgtga ggcgctgccc atgcctgaga gccccgacgc tgccaactgc        900
atgcgcattg gcatcccagc cgagaggctg ggccgctacc atcagtgcta taacggctca        960
ggcatggatt acagaggaac ggcaagcacc accaagtcag gccaccagtg ccagccgtgg       1020
gccctgcagc accccacag ccaccacctg tccagcacag acttccctga gcttggaggg       1080
gggcacgcct actgccggaa ccccggaggc cagatggagg gcccctggtg ctttacgcag       1140
aataaaaacg tacgcatgga actgtgtgac gtaccctcgt gtagtccccg agacagcagc       1200
aagatgggga ttctgtacat cttggtcccc agcatcgcaa ttccactggt catcgcttgc       1260
cttttcttct tggtttgcat gtgccggaat aagcagaagg catctgcgtc cacaccgcag       1320
cggcgacagc tgatggcctc gcccagccaa gacatggaaa tgcccctcat taaccagcac       1380
aaacaggcca aactcaaaga gatcagcctg tctgcggtga ggttcatgga ggagctggga       1440
gaggaccggt ttgggaaagt ctacaaaggt cacctgttcg gccctgcccc gggggagcag       1500
acccaggctg tggccatcaa aacgctgaag gacaaagcgg aggggcccct gcgggaggag       1560
ttccggcatg aggctatgct gcgagcacgg ctgcaacacc caacgtcgt ctgcctgctg       1620 ggcgtggtga ccaaggacca gcccctgagc atgatcttca gctactgttc gcacggcgac       1680
ctccacgaat tcctggtcat cgcctcgccg cactcggacg tgggcagcac cgatgatgac       1740
cgcacggtga agtccgccct ggagcccccc gacttcgtgc accttgtggc acagatcgcg       1800
gcggggatgg agtacctatc cagccaccac gtggttcaca aggacctggc cacccgcaat       1860
gtgctagtgt acgacaagct gaacgtgaag atctcagact tgggcctctt ccgagaggtg       1920
tatgccgccg attactacaa gctgctgggg aactcgctgc tgcctatccg ctggatggcc       1980
ccagaggcca tcatgtacgg caagttctcc atcgactcag acatctggtc ctacggtgtg       2040
gtcctgtggg aggtcttcag ctacggcctg cagccctact gcgggtactc caaccaggat       2100
gtggtggaga tgatccggaa ccggcaggtg ctgccttgcc ccgatgactg tcccgcctgg       2160
gtgtatgccc tcatgatcga gtgctggaac gagttcccca gccggcggcc ccgcttcaag       2220
gacatccaca gccggctccg agcctggggc aacctttcca actacaacag ctcggcgcag       2280
acctcggggg ccagcaacac cacgcagacc agctccctga gcaccagccc agtgagcaat       2340
gtgagcaacg cccgctacgt ggggcccaag cagaaggccc gcccttccc acagccccag       2400 ttcatcccca tgaagggcca gatcagaccc atggtgcccc gccgcagct ctacgtcccc       2460 gtcaacggct accagccggt gccggcctat ggggcctacc tgcccaactt ctacccggtg       2520
cagatcccaa tgcagatggc cccgcagcag gtgcctcctc agatggtccc caagcccagc       2580
tcacaccaca gtggcagtgg ctccaccagc acaggctacg tcaccacggc ccctccaac       2640 acatccatgg cagacagggc agccctgctc tcagagggcg ctgatgacac acagaacgcc       2700
ccagaagatg gggcccagag caccgtgcag gaagcagagg aggaggagga aggctctgtc       2760
ccagagactg agctgctggg ggactgtgac actctgcagg tggacgaggc ccaagtccag       2820
ctggaagctt ga                                                          2832
```

<210> SEQ ID NO 18
<211> LENGTH: 943
<212> TYPE: PRT
<213> ORGANISM: Homo sapiens

<400> SEQUENCE: 18

-continued

```
Met Ala Arg Gly Ser Ala Leu Pro Arg Arg Pro Leu Leu Cys Ile Pro
1               5                   10                  15

Ala Val Trp Ala Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp
        35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
            85                  90                  95

Lys Asn Asp Ala Pro Val Val Gln Glu Pro Arg Arg Ile Ile Ile Arg
            100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Met Lys Thr Ile
    130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
            245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
            325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
            355                 360                 365

Gly Gly Gln Met Glu Gly Pro Trp Cys Phe Thr Gln Asn Lys Asn Val
    370                 375                 380

Arg Met Glu Leu Cys Asp Val Pro Ser Cys Ser Pro Arg Asp Ser Ser
385                 390                 395                 400

Lys Met Gly Ile Leu Tyr Ile Leu Val Pro Ser Ile Ala Ile Pro Leu
            405                 410                 415
```

-continued

```
Val Ile Ala Cys Leu Phe Phe Leu Val Cys Met Cys Arg Asn Lys Gln
            420             425             430

Lys Ala Ser Ala Ser Thr Pro Gln Arg Arg Gln Leu Met Ala Ser Pro
            435             440             445

Ser Gln Asp Met Glu Met Pro Leu Ile Asn Gln His Lys Gln Ala Lys
            450             455             460

Leu Lys Glu Ile Ser Leu Ser Ala Val Arg Phe Met Glu Glu Leu Gly
465             470             475             480

Glu Asp Arg Phe Gly Lys Val Tyr Lys Gly His Leu Phe Gly Pro Ala
                485             490             495

Pro Gly Glu Gln Thr Gln Ala Val Ala Ile Lys Thr Leu Lys Asp Lys
            500             505             510

Ala Glu Gly Pro Leu Arg Glu Glu Phe Arg His Glu Ala Met Leu Arg
            515             520             525

Ala Arg Leu Gln His Pro Asn Val Val Cys Leu Leu Gly Val Val Thr
            530             535             540

Lys Asp Gln Pro Leu Ser Met Ile Phe Ser Tyr Cys Ser His Gly Asp
545             550             555             560

Leu His Glu Phe Leu Val Met Arg Ser Pro His Ser Asp Val Gly Ser
                565             570             575

Thr Asp Asp Asp Arg Thr Val Lys Ser Ala Leu Glu Pro Pro Asp Phe
            580             585             590

Val His Leu Val Ala Gln Ile Ala Ala Gly Met Glu Tyr Leu Ser Ser
            595             600             605

His His Val Val His Lys Asp Leu Ala Thr Arg Asn Val Leu Val Tyr
            610             615             620

Asp Lys Leu Asn Val Lys Ile Ser Asp Leu Gly Leu Phe Arg Glu Val
625             630             635             640

Tyr Ala Ala Asp Tyr Tyr Lys Leu Leu Gly Asn Ser Leu Leu Pro Ile
                645             650             655

Arg Trp Met Ala Pro Glu Ala Ile Met Tyr Gly Lys Phe Ser Ile Asp
            660             665             670

Ser Asp Ile Trp Ser Tyr Gly Val Val Leu Trp Glu Val Phe Ser Tyr
            675             680             685

Gly Leu Gln Pro Tyr Cys Gly Tyr Ser Asn Gln Asp Val Val Glu Met
            690             695             700

Ile Arg Asn Arg Gln Val Leu Pro Cys Pro Asp Asp Cys Pro Ala Trp
705             710             715             720

Val Tyr Ala Leu Met Ile Glu Cys Trp Asn Glu Phe Pro Ser Arg Arg
                725             730             735

Pro Arg Phe Lys Asp Ile His Ser Arg Leu Arg Ala Trp Gly Asn Leu
            740             745             750

Ser Asn Tyr Asn Ser Ser Ala Gln Thr Ser Gly Ala Ser Asn Thr Thr
            755             760             765

Gln Thr Ser Ser Leu Ser Thr Ser Pro Val Ser Asn Val Ser Asn Ala
            770             775             780

Arg Tyr Val Gly Pro Lys Gln Lys Ala Pro Pro Phe Pro Gln Pro Gln
785             790             795             800

Phe Ile Pro Met Lys Gly Gln Ile Arg Pro Met Val Pro Pro Gln
                805             810             815

Leu Tyr Val Pro Val Asn Gly Tyr Gln Pro Val Pro Ala Tyr Gly Ala
                820             825             830

Tyr Leu Pro Asn Phe Tyr Pro Val Gln Ile Pro Met Gln Met Ala Pro
```

-continued

```
                835                840                845

Gln Gln Val Pro Pro Gln Met Val Pro Lys Pro Ser Ser His His Ser
        850                855                860

Gly Ser Gly Ser Thr Ser Thr Gly Tyr Val Thr Thr Ala Pro Ser Asn
865                870                875                880

Thr Ser Met Ala Asp Arg Ala Ala Leu Leu Ser Glu Gly Ala Asp Asp
                885                890                895

Thr Gln Asn Ala Pro Glu Asp Gly Ala Gln Ser Thr Val Gln Glu Ala
            900                905                910

Glu Glu Glu Glu Glu Gly Ser Val Pro Glu Thr Glu Leu Leu Gly Asp
            915                920                925

Cys Asp Thr Leu Gln Val Asp Glu Ala Gln Val Gln Leu Glu Ala
    930                935                940
```

```
<210> SEQ ID NO 19
<211> LENGTH: 2835
<212> TYPE: DNA
<213> ORGANISM: Artificial Sequence
<220> FEATURE:
<223> OTHER INFORMATION: Synthetic polynucleotide

<400> SEQUENCE: 19
atggctcggg gctgggtgcg gccgagccgt gtgcctctgt gcgcccgggc cgtctggacg      60
gctgcggcgc tcctgctctg gacaccctgg acggcaggtg aagtggaaga ttcggaggca     120
atcgacacct tgggacaacc tgatggaccg gacagcccac ttcccactct gaaaggctac     180
tttctgaatt ttctggagcc agtcaacaat atcaccattg ttcagggcca gacggcaatc     240
ctgcactgca aggtggcggg aaacccacct cccaatgtgc ggtggctgaa gaatgatgcc     300
ccggttgtgc aagagccacg aagggtcgtc atccggaaga cagaatacgg ctcccggctg     360
cggatccaag acctggacac aacagacaca ggctactacc agtgtgtggc taccaacggg     420
ctgaagacca tcactgccac tggggttcta tatgtgcggc tcggtccgac gcacagcccg     480
aaccacaatt ttcaggatga cgatcaggaa gatggcttct gccagccgta ccgagggatc     540
gcttgtgcgc gcttcattgg gaaccggact atttatgtgg actccctcca gatgcagggg     600
gagattgaaa accgaatcac agctgccttc accatgatcg gcacctccac gcaactgtca     660
gaccagtgtt cacagtttgc catcccatcc ttctgccact cgtcttccc tctgtgcgac      720 gcatgctccc gggcgcccaa gcctcgcgaa ctgtgccggg atgaatgtga ggtgctggag     780
aacgacctgt gccgccagga gtacaccatc gcccgctcca cccgctcat cctcatgcgg      840 ctccagctgc ccaagtgcga agcgctgccc atgcccgaga gcccggatgc tgcgaactgc     900
atgcgcatcg ggatccccgc ggagaggctg ggtcgctacc accagtgcta caacggctcc     960
ggcgccgatt acaggggat ggccagtacc accaagtcag gccaccagtg tcagccttgg    1020
gctctgcagc accccacag ccatcgccta tccagcacgg aattccctga gctgggagga    1080
ggccatgcct actgccggaa ccccggggc cagatggaag gcccgtggtg ctttacgcag    1140
aataaaaacg tacgcgtgga actgtgtgac gtaccccgt gtagtccccg atatggcagc    1200
aagatgggga ttctgtacat cctggtcccc agcattgcta ccccctggt catcgcttgc    1260 ctgttcttcc tcgtctgcat gtgccgcaac aaacagaagg cttcggcctc caccccacag    1320
cgccggcagc tgatggcctc tcccagccag gacatggaga tgccactcat cagccagcac    1380
aaacaggcca aactcaaaga gatcagcttg tccacagtga ggttcatgga ggagctcggg    1440
gaggaccggt ttggcaaggt ctacaaaggc cacctgttcg ggcctgcccc aggagaacca    1500
```

```
acccaggccg tggccatcaa gacgctgaaa gacaaggctg aggggcccct gcgggaggag        1560
ttccggcaag aggcgatgct ccgggcccga ctgcagcacc ccaacatcgt ctgtctccta        1620
ggcgtcgtga ccaaggacca acccttgagc atgatcttca gctactgttc ccatggcgac        1680
cttcatgaat tcctggtcat gcgctcgccg cactccgatg tgggcagcac cgatgacgac        1740
cgcacagtga agtcagccct ggagcccccg gacttcgtgc acgtggtggc gcagatcgct        1800
gcggggatgg agttcctgtc cagccaccac gtgtgccata aggacctggc cacacgcaat        1860
gtgctggtgt acgacaagct gaacgtgagg atctcagact tgggcctctt ccgtgaggta        1920
tactccgcag attactacaa actcatgggc aattcactgc tgcccatccg ctggatgtcc        1980
cccgaggccg tcatgtatgg aaagttctcc atcgactctg acatctggtc ctacggtgtg        2040
gtcctctggg aggtctttag ctacggcctg cagccctact gtgggtactc caaccaggac        2100
gtggtggaga tgatccggag ccggcaggtg ctgccctgcc cggatgactg ccccgcctgg        2160
gtctatgccc tcatgattga atgctggaat gagttcccaa gccggaggcc ccgctttaag        2220
gacatccaca gccggctccg gtcctggggc aacctatcca actataatag ttccgcgcag        2280
acctcaggag ccagcaacac cacacagacc agctccctga gcaccagccc cgtaagcaat        2340
gtgagcaatg cccgctatat ggcccccaag cagaaggccc agcccttccc acagcctcag        2400
ttcatcccca tgaagggtca gatcagaccc ttggtgcccc ccgcacagct gtacatcccg        2460
gtgaacggct atcagccggt accggcatac ggggcctacc tgcccaactt ctacccagtc        2520
cagatcccca tgcagatggc cccacagcag gtgccccctc agatggtccc caagccgagc        2580
tcacaccaca gtggcagcgg ctccaccagc actggctacg tcaccacggc gccctccaat        2640
acatctgtgg cggacagggc ggccctactc tctgagggca ccgaggatgt acagaacatc        2700
gcggaagacg tggcccagag ccctgtgcag gaagcagagg aggaggagga ggggtctgtc        2760
cctgagactg aactcctggg agacaatgac acgctccagg tgaccgaggc ggctcatgtc        2820
cagcttgaag cctga                                                        2835
```

```
<210> SEQ ID NO 20
<211> LENGTH: 944
<212> TYPE: PRT
<213> ORGANISM: Mus musculus

<400> SEQUENCE: 20

Met Ala Arg Gly Trp Val Arg Pro Ser Arg Val Pro Leu Cys Ala Arg
1               5                   10                  15

Ala Val Trp Thr Ala Ala Ala Leu Leu Leu Trp Thr Pro Trp Thr Ala
            20                  25                  30

Gly Glu Val Glu Asp Ser Glu Ala Ile Asp Thr Leu Gly Gln Pro Asp
        35                  40                  45

Gly Pro Asp Ser Pro Leu Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
            85                  90                  95

Lys Asn Asp Ala Pro Val Val Gln Glu Pro Arg Arg Val Val Ile Arg
            100                 105                 110

Lys Thr Glu Tyr Gly Ser Arg Leu Arg Ile Gln Asp Leu Asp Thr Thr
        115                 120                 125
```

```
Asp Thr Gly Tyr Tyr Gln Cys Val Ala Thr Asn Gly Leu Lys Thr Ile
    130                 135                 140

Thr Ala Thr Gly Val Leu Tyr Val Arg Leu Gly Pro Thr His Ser Pro
145                 150                 155                 160

Asn His Asn Phe Gln Asp Asp Asp Gln Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr Gln Leu Ser Asp Gln Cys Ser
    210                 215                 220

Gln Phe Ala Ile Pro Ser Phe Cys His Phe Val Phe Pro Leu Cys Asp
225                 230                 235                 240

Ala Cys Ser Arg Ala Pro Lys Pro Arg Glu Leu Cys Arg Asp Glu Cys
                245                 250                 255

Glu Val Leu Glu Asn Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Ala Asp Tyr Arg Gly Met Ala Ser Thr Thr Lys Ser Gly His Gln
                325                 330                 335

Cys Gln Pro Trp Ala Leu Gln His Pro His Ser His Arg Leu Ser Ser
                340                 345                 350

Thr Glu Phe Pro Glu Leu Gly Gly Gly His Ala Tyr Cys Arg Asn Pro
            355                 360                 365

Gly Gly Gln Met Glu Gly Pro Trp Cys Phe Thr Gln Asn Lys Asn Val
    370                 375                 380

Arg Val Glu Leu Cys Asp Val Pro Pro Cys Ser Pro Arg Tyr Gly Ser
385                 390                 395                 400

Lys Met Gly Ile Leu Tyr Ile Leu Val Pro Ser Ile Ala Ile Pro Leu
                405                 410                 415

Val Ile Ala Cys Leu Phe Phe Leu Val Cys Met Cys Arg Asn Lys Gln
                420                 425                 430

Lys Ala Ser Ala Ser Thr Pro Gln Arg Arg Gln Leu Met Ala Ser Pro
            435                 440                 445

Ser Gln Asp Met Glu Met Pro Leu Ile Ser Gln His Lys Gln Ala Lys
    450                 455                 460

Leu Lys Glu Ile Ser Leu Ser Thr Val Arg Phe Met Glu Glu Leu Gly
465                 470                 475                 480

Glu Asp Arg Phe Gly Lys Val Tyr Lys Gly His Leu Phe Gly Pro Ala
                485                 490                 495

Pro Gly Glu Pro Thr Gln Ala Val Ala Ile Lys Thr Leu Lys Asp Lys
            500                 505                 510

Ala Glu Gly Pro Leu Arg Glu Glu Phe Arg Gln Glu Ala Met Leu Arg
            515                 520                 525

Ala Arg Leu Gln His Pro Asn Ile Val Cys Leu Leu Gly Val Val Thr
    530                 535                 540

Lys Asp Gln Pro Leu Ser Met Ile Phe Ser Tyr Cys Ser His Gly Asp
```

```
545               550               555               560

Leu His Glu Phe Leu Val Met Arg Ser Pro His Ser Asp Val Gly Ser
            565               570               575

Thr Asp Asp Asp Arg Thr Val Lys Ser Ala Leu Glu Pro Pro Asp Phe
            580               585               590

Val His Val Val Ala Gln Ile Ala Ala Gly Met Glu Phe Leu Ser Ser
            595               600               605

His His Val Cys His Lys Asp Leu Ala Thr Arg Asn Val Leu Val Tyr
            610               615               620

Asp Lys Leu Asn Val Arg Ile Ser Asp Leu Gly Leu Phe Arg Glu Val
625               630               635               640

Tyr Ser Ala Asp Tyr Tyr Lys Leu Met Gly Asn Ser Leu Leu Pro Ile
            645               650               655

Arg Trp Met Ser Pro Glu Ala Val Met Tyr Gly Lys Phe Ser Ile Asp
            660               665               670

Ser Asp Ile Trp Ser Tyr Gly Val Val Leu Trp Glu Val Phe Ser Tyr
            675               680               685

Gly Leu Gln Pro Tyr Cys Gly Tyr Ser Asn Gln Asp Val Val Glu Met
            690               695               700

Ile Arg Ser Arg Gln Val Leu Pro Cys Pro Asp Asp Cys Pro Ala Trp
705               710               715               720

Val Tyr Ala Leu Met Ile Glu Cys Trp Asn Glu Phe Pro Ser Arg Arg
            725               730               735

Pro Arg Phe Lys Asp Ile His Ser Arg Leu Arg Ser Trp Gly Asn Leu
            740               745               750

Ser Asn Tyr Asn Ser Ser Ala Gln Thr Ser Gly Ala Ser Asn Thr Thr
            755               760               765

Gln Thr Ser Ser Leu Ser Thr Ser Pro Val Ser Asn Val Ser Asn Ala
            770               775               780

Arg Tyr Met Ala Pro Lys Gln Lys Ala Gln Pro Phe Pro Gln Pro Gln
785               790               795               800

Phe Ile Pro Met Lys Gly Gln Ile Arg Pro Leu Val Pro Pro Ala Gln
            805               810               815

Leu Tyr Ile Pro Val Asn Gly Tyr Gln Pro Val Pro Ala Tyr Gly Ala
            820               825               830

Tyr Leu Pro Asn Phe Tyr Pro Val Gln Ile Pro Met Gln Met Ala Pro
            835               840               845

Gln Gln Val Pro Pro Gln Met Val Pro Lys Pro Ser Ser His His Ser
            850               855               860

Gly Ser Gly Ser Thr Ser Thr Gly Tyr Val Thr Thr Ala Pro Ser Asn
865               870               875               880

Thr Ser Val Ala Asp Arg Ala Ala Leu Leu Ser Glu Gly Thr Glu Asp
            885               890               895

Val Gln Asn Ile Ala Glu Asp Val Ala Gln Ser Pro Val Gln Glu Ala
            900               905               910

Glu Glu Glu Glu Glu Gly Ser Val Pro Glu Thr Glu Leu Leu Gly Asp
            915               920               925

Asn Asp Thr Leu Gln Val Thr Glu Ala Ala His Val Gln Leu Glu Ala
            930               935               940
```

<210> SEQ ID NO 21
<211> LENGTH: 1209
<212> TYPE: DNA
<213> ORGANISM: Artificial Sequence
<220> FEATURE:
<223> OTHER INFORMATION: Synthetic polynucleotide

<400> SEQUENCE: 21

```
atggcccggg gctcggcgct cccgcggcgg ccgctgctgt gcatcccggc cgtctgggcg      60
gccgccgcgc ttctgctctc agtgtcccgg acttcaggtg aagtggaggt tctggatccg     120
aacgacccct taggacccct tgatgggcag gacggcccga ttccaactct gaaaggttac     180
tttctgaatt ttctggagcc agtaaacaat atcaccattg tccaaggcca gacggcaatt     240
ctgcactgca aggtggcagg aaacccaccc cctaacgtgc ggtggctaaa gaatgatgcc     300
ccggtggtgc aggagccgcg gcggatcatc atccggaaga cagaatatgg ttcacgactg     360
cgaatccagg acctggacac gacagacact ggctactacc agtgcgtggc caccaacggg     420
atgaagacca ttaccgccac tggcgtcctg tttgtgcggc tgggtccaac gcacagccca     480
aatcataact ttcaggatga ttaccacgag gatgggttct gccagcctta ccggggaatt     540
gcctgtgcac gcttcattgg caaccggacc atttatgtgg actcgcttca gatgcagggg     600
gagattgaaa accgaatcac agcggccttc accatgatcg gcacgtctac gcacctgtcg     660
gaccagtgct cacagttcgc catcccatcc ttctgccact tcgtgtttcc tctgtgcgac     720
gcgcgctccc gggcacccaa gccgcgtgag ctgtgccgcg acgagtgcga ggtgctggag     780
agcgacctgt gccgccagga gtacaccatc gcccgctcca acccgctcat cctcatgcgg     840
cttcagctgc ccaagtgtga ggcgctgccc atgcctgaga gccccgacgc tgccaactgc     900
atgcgcattg gcatcccagc cgagaggctg ggccgctacc atcagtgcta taacggctca     960
ggcatggatt acagaggaac ggcaagcacc accaagtcag gccaccagtg ccagccgtgg    1020
gccctgcagc accccacag ccaccacctg tccagcacag acttccctga gcttggaggg    1080
gggcacgcct actgccggaa ccccggaggc cagatggagg gcccctggtg ctttacgcag    1140
aataaaaacg tacgcatgga actgtgtgac gtaccctcgt gtagtccccg agacagcagc    1200
aagatgggg                                                            1209
```

<210> SEQ ID NO 22
<211> LENGTH: 403
<212> TYPE: PRT
<213> ORGANISM: Homo sapiens

<400> SEQUENCE: 22

```
Met Ala Arg Gly Ser Ala Leu Pro Arg Arg Pro Leu Leu Cys Ile Pro
1               5                   10                  15

Ala Val Trp Ala Ala Ala Ala Leu Leu Leu Ser Val Ser Arg Thr Ser
            20                  25                  30

Gly Glu Val Glu Val Leu Asp Pro Asn Asp Pro Leu Gly Pro Leu Asp
        35                  40                  45

Gly Gln Asp Gly Pro Ile Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
                85                  90                  95

Lys Asn Asp Ala Pro Val Val Gln Glu Pro Arg Arg Ile Ile Ile Arg
            100                 105                 110

Lys Thr Glu Tyr Gly Ser Arg Leu Arg Ile Gln Asp Leu Asp Thr Thr
        115                 120                 125
```

```
Asp Thr Gly Tyr Tyr Gln Cys Val Ala Thr Asn Gly Met Lys Thr Ile
    130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
            180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
    210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
            355                 360                 365

Gly Gly Gln Met Glu Gly Pro Trp Cys Phe Thr Gln Asn Lys Asn Val
    370                 375                 380

Arg Met Glu Leu Cys Asp Val Pro Ser Cys Ser Pro Arg Asp Ser Ser
385                 390                 395                 400

Lys Met Gly
```

```
<210> SEQ ID NO 23
<211> LENGTH: 1209
<212> TYPE: DNA
<213> ORGANISM: Artificial Sequence
<220> FEATURE:
<223> OTHER INFORMATION: Synthetic polynucleotide

<400> SEQUENCE: 23
atggctcggg gctgggtgcg gccgagccgt gtgcctctgt gcgcccgggc cgtctggacg      60
gctgcggcgc tcctgctctg dacaccctgg acggcaggtg aagtggaaga ttcggaggca     120
atcgacacct tgggacaacc tgatggaccg gacagcccac ttcccactct gaaaggctac     180
tttctgaatt ttctggagcc agtcaacaat atcaccattg ttcagggcca gacggcaatc     240
ctgcactgca aggtggcggg aaacccacct cccaatgtgc ggtggctgaa gaatgatgcc     300
ccggttgtgc aagagccacg aagggtcgtc atccggaaga cagaatacgg ctcccggctg     360
cggatccaag acctggacac aacagacaca ggctactacc agtgtgtggc taccaacggg     420
ctgaagacca tcactgccac tgggggttcta tatgtgcggc tcggtccgac gcacagcccg     480
```

-continued

```
aaccacaatt ttcaggatga cgatcaggaa gatggcttct gccagccgta ccgagggatc      540
gcttgtgcgc gcttcattgg gaaccggact atttatgtgg actccctcca gatgcagggg      600
gagattgaaa accgaatcac agctgccttc accatgatcg gcacctccac gcaactgtca      660
gaccagtgtt cacagtttgc catcccatcc ttctgccact tcgtcttccc tctgtgcgac      720
gcatgctccc gggcgcccaa gcctcgcgaa ctgtgccggg atgaatgtga ggtgctggag      780
aacgacctgt gccgccagga gtacaccatc gcccgctcca cccgctcat cctcatgcgg      840 ctccagctgc ccaagtgcga agcgctgccc atgcccgaga gcccggatgc tgcgaactgc      900
atgcgcatcg ggatccccgc ggagaggctg ggtcgctacc accagtgcta caacggctcc      960
ggcgccgatt acaggggggat ggccagtacc accaagtcag gccaccagtg tcagccttgg     1020
gctctgcagc accccacag ccatcgccta tccagcacgg aattccctga gctgggagga     1080
ggccatgcct actgccggaa ccccgggggc cagatggaag gcccgtggtg ctttacgcag     1140
aataaaaacg tacgcgtgga actgtgtgac gtaccccgt gtagtccccg atatggcagc     1200
aagatgggg                                                            1209
```

<210> SEQ ID NO 24
<211> LENGTH: 403
<212> TYPE: PRT
<213> ORGANISM: Mus musculus

<400> SEQUENCE: 24

```
Met Ala Arg Gly Trp Val Arg Pro Ser Arg Val Pro Leu Cys Ala Arg
1               5                   10                  15

Ala Val Trp Thr Ala Ala Ala Leu Leu Leu Trp Thr Pro Trp Thr Ala
            20                  25                  30

Gly Glu Val Glu Asp Ser Glu Ala Ile Asp Thr Leu Gly Gln Pro Asp
        35                  40                  45

Gly Pro Asp Ser Pro Leu Pro Thr Leu Lys Gly Tyr Phe Leu Asn Phe
    50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Asn Val Arg Trp Leu
                85                  90                  95

Lys Asn Asp Ala Pro Val Val Gln Glu Pro Arg Arg Val Val Ile Arg
                100                 105                 110

Lys Thr Glu Tyr Gly Ser Arg Leu Arg Ile Gln Asp Leu Asp Thr Thr
            115                 120                 125

Asp Thr Gly Tyr Tyr Gln Cys Val Ala Thr Asn Gly Leu Lys Thr Ile
            130                 135                 140

Thr Ala Thr Gly Val Leu Tyr Val Arg Leu Gly Pro Thr His Ser Pro
145                 150                 155                 160

Asn His Asn Phe Gln Asp Asp Asp Gln Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr Gln Leu Ser Asp Gln Cys Ser
        210                 215                 220

Gln Phe Ala Ile Pro Ser Phe Cys His Phe Val Phe Pro Leu Cys Asp
225                 230                 235                 240
```

```
Ala Cys Ser Arg Ala Pro Lys Pro Arg Glu Leu Cys Arg Asp Glu Cys
                245                 250                 255

Glu Val Leu Glu Asn Asp Leu Cys Arg Gln Glu Tyr Thr Ile Ala Arg
            260                 265                 270

Ser Asn Pro Leu Ile Leu Met Arg Leu Gln Leu Pro Lys Cys Glu Ala
        275                 280                 285

Leu Pro Met Pro Glu Ser Pro Asp Ala Ala Asn Cys Met Arg Ile Gly
    290                 295                 300

Ile Pro Ala Glu Arg Leu Gly Arg Tyr His Gln Cys Tyr Asn Gly Ser
305                 310                 315                 320

Gly Ala Asp Tyr Arg Gly Met Ala Ser Thr Thr Lys Ser Gly His Gln
                325                 330                 335

Cys Gln Pro Trp Ala Leu Gln His Pro His Ser His Arg Leu Ser Ser
                340                 345                 350

Thr Glu Phe Pro Glu Leu Gly Gly Gly His Ala Tyr Cys Arg Asn Pro
            355                 360                 365

Gly Gly Gln Met Glu Gly Pro Trp Cys Phe Thr Gln Asn Lys Asn Val
    370                 375                 380

Arg Val Glu Leu Cys Asp Val Pro Pro Cys Ser Pro Arg Tyr Gly Ser
385                 390                 395                 400

Lys Met Gly
```

<210> SEQ ID NO 25
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 25

```
Gly Phe Thr Phe Ser Asn Tyr Gly
1               5
```

<210> SEQ ID NO 26
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 26

```
Ile Ser Ser Gly Gly Gly Tyr Thr
1               5
```

<210> SEQ ID NO 27
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 27

```
His Pro Arg Asp Phe Ser Tyr Ala Met Asp Tyr
1               5                   10
```

<210> SEQ ID NO 28
<211> LENGTH: 6
<212> TYPE: PRT
<213> ORGANISM: Artificial Sequence
<220> FEATURE:
<223> OTHER INFORMATION: Synthetic polypeptide

```
<400> SEQUENCE: 28

Gln Asp Val Gly His Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 29

Trp Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 30

Gln Gln Tyr Asn Ile Tyr Pro Trp Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 31

Gly Tyr Thr Phe Thr Asp Tyr Glu
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 32

Ile His Pro Gly Ser Gly Gly Thr
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 33

Arg Arg Pro Arg Phe Tyr Gly Met Asp Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 34
```

Lys Ser Leu Leu His Ser Asn Gly Asn Thr Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 35

Arg Met Ser
1

<210> SEQ ID NO 36
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 36

Met Gln His Leu Glu Tyr Pro Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 37

Gly Phe Thr Phe Ser Asn Tyr Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 38

Ile Ser Ser Gly Gly Gly Ser Thr
1               5

<210> SEQ ID NO 39
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 39

His Pro Tyr Asp Tyr Gly Tyr Tyr Phe Asp Tyr
1               5                   10

<210> SEQ ID NO 40
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 40

```
Gln Ser Ile Gly Thr Ser
1               5

<210> SEQ ID NO 41
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 41

Tyr Ala Ser
1

<210> SEQ ID NO 42
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 42

Gln Gln Ser Asp Ser Trp Pro Phe Pro
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 43

Gly Phe Thr Phe Asn Thr Tyr Ala
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 44

Ile Arg Ser Lys Ser Asn Asn Tyr Ala Thr
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 45

His Gly Ser Ser Leu Tyr Tyr Ala Met Asp Tyr
1               5                   10

<210> SEQ ID NO 46
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 46

Gln Glu Ile Ser Gly Tyr
```

```
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 47

Ala Ala Ser
1

<210> SEQ ID NO 48
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 48

Leu Gln Tyr Ala Ser Tyr Pro Tyr Thr
1               5

<210> SEQ ID NO 49
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 49

Glu Val Gln Leu Val Glu Ser Gly Gly Asp Leu Val Lys Pro Gly Gly
1               5                   10                  15

Ser Leu Lys Leu Ser Cys Ala Ala Ser
            20                  25

<210> SEQ ID NO 50
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 50

Met Ser Trp Val Arg Gln Thr Pro Asp Lys Arg Leu Glu Trp Val Ala
1               5                   10                  15

Thr

<210> SEQ ID NO 51
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 51

His Tyr Val Asp Ser Val Lys Gly Arg Phe Thr Ile Ser Arg Asp Asn
1               5                   10                  15

Ala Asn His Ile Leu Tyr Leu Gln Met Ser Ser Leu Asn Ser Glu Asp
            20                  25                  30

Thr Ala Met Tyr Tyr Cys Ala Arg
            35                  40
```

```
<210> SEQ ID NO 52
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 52

Trp Gly Gln Gly Thr Ser Val Thr Val Ser Ser
1               5                   10

<210> SEQ ID NO 53
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 53

Asp Ile Val Met Thr Gln Ser His Lys Phe Met Ser Thr Ser Ile Gly
1               5                   10                  15

Asp Arg Val Ser Ile Thr Cys Lys Ala Ser
            20                  25

<210> SEQ ID NO 54
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 54

Val Ala Trp Tyr Gln Gln Lys Pro Gly Gln Ser Pro Lys Leu Leu Ile
1               5                   10                  15

Tyr

<210> SEQ ID NO 55
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 55

Thr Arg His Thr Gly Val Pro Asp Arg Phe Thr Gly Ser Gly Ser Gly
1               5                   10                  15

Thr Asp Phe Thr Leu Thr Ile Ser Asn Val Gln Ser Glu Asp Leu Ala
            20                  25                  30

Asp Tyr Phe Cys
        35

<210> SEQ ID NO 56
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 56

Phe Gly Gly Gly Ser Lys Leu Ala Ile Lys
1               5                   10

<210> SEQ ID NO 57
<211> LENGTH: 25
<212> TYPE: PRT
```

<213> ORGANISM: Artificial Sequence
<220> FEATURE:
<223> OTHER INFORMATION: Synthetic polypeptide

<400> SEQUENCE: 57

Gln Val Gln Leu Gln Gln Ser Gly Ala Glu Leu Val Arg Pro Gly Ala
1               5                   10                  15

Ser Val Lys Leu Ser Cys Lys Ala Leu
            20                  25

<210> SEQ ID NO 58
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 58

Met His Trp Val Lys Gln Thr Pro Val His Gly Leu Glu Trp Ile Gly
1               5                   10                  15

Ala

<210> SEQ ID NO 59
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 59

Ala Tyr Asn Gln Lys Phe Lys Gly Lys Ala Thr Leu Thr Ala Asp Lys
1               5                   10                  15

Ser Ser Ser Thr Ala Tyr Met Glu Leu Ser Arg Leu Thr Ser Glu Asp
            20                  25                  30

Ser Ala Val Tyr Tyr Cys Thr Arg
        35                  40

<210> SEQ ID NO 60
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 60

Trp Gly Gln Gly Thr Ser Val Thr Val Ser Ser
1               5                   10

<210> SEQ ID NO 61
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 61

Asp Ile Val Met Thr Gln Ala Ala Pro Ser Val Pro Val Thr Pro Gly
1               5                   10                  15

Glu Ser Val Ser Ile Ser Cys Arg Ser Ser
            20                  25

<210> SEQ ID NO 62
<211> LENGTH: 17
<212> TYPE: PRT

-continued

<213> ORGANISM: Artificial Sequence
<220> FEATURE:
<223> OTHER INFORMATION: Synthetic polypeptide

<400> SEQUENCE: 62

Leu Tyr Trp Phe Leu Gln Arg Pro Gly Gln Ser Pro Gln Leu Leu Ile
1               5                   10                  15

Tyr

<210> SEQ ID NO 63
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 63

Asn Leu Ala Ser Gly Val Pro Asp Arg Phe Ser Gly Ser Gly Ser Gly
1               5                   10                  15

Thr Ala Phe Thr Leu Arg Ile Ser Arg Val Glu Ala Glu Asp Val Gly
            20                  25                  30

Val Tyr Tyr Cys
        35

<210> SEQ ID NO 64
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 64

Val Gly Ala Gly Thr Lys Leu Glu Leu Lys
1               5                   10

<210> SEQ ID NO 65
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 65

Glu Val Gln Leu Val Glu Ser Gly Gly Asp Leu Val Lys Pro Gly Gly
1               5                   10                  15

Ser Leu Lys Leu Ser Cys Ala Ala Ser
            20                  25

<210> SEQ ID NO 66
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 66

Met Ser Trp Val Arg Gln Thr Pro Asp Lys Arg Leu Glu Trp Val Ala
1               5                   10                  15

Thr

<210> SEQ ID NO 67
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 67

Tyr Tyr Pro Asp Ser Val Lys Gly Arg Phe Thr Ile Ser Arg Asp Asn
1               5                   10                  15

Ala Lys Asn Ser Leu Tyr Leu Gln Met Ser Ser Leu Lys Ser Glu Asp
            20                  25                  30

Thr Ala Met Tyr Tyr Cys Ala Arg
        35                  40

<210> SEQ ID NO 68
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 68

Trp Gly Gln Gly Thr Thr Leu Thr Val Ser Ser
1               5                   10

<210> SEQ ID NO 69
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 69

Asp Ile Leu Leu Thr Gln Ser Pro Asp Ile Leu Ser Val Ser Pro Gly
1               5                   10                  15

Glu Arg Val Ser Phe Ser Cys Arg Ala Ser
            20                  25

<210> SEQ ID NO 70
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 70

Ile His Trp Tyr Gln Gln Arg Thr Asn Gly Ser Pro Arg Leu Leu Ile
1               5                   10                  15

Lys

<210> SEQ ID NO 71
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 71

Glu Ser Ile Ser Gly Ile Pro Ser Arg Phe Ser Gly Ser Gly Ser Gly
1               5                   10                  15

Thr Asp Phe Thr Leu Ser Ile Asn Ser Val Glu Ser Glu Asp Ile Ala
            20                  25                  30

Asp Tyr Tyr Cys
        35

<210> SEQ ID NO 72

```
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 72

Phe Gly Ser Gly Thr Lys Leu Glu Lys Lys
1               5                   10

<210> SEQ ID NO 73
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 73

Glu Val Gln Leu Val Glu Ser Gly Gly Gly Leu Val Gln Pro Lys Gly
1               5                   10                  15

Ser Leu Lys Leu Ser Cys Ala Ala Ser
            20                  25

<210> SEQ ID NO 74
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 74

Met Asn Trp Val Arg Gln Ala Pro Gly Lys Gly Leu Glu Trp Val Ala
1               5                   10                  15

Arg

<210> SEQ ID NO 75
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 75

Tyr Tyr Ala Asp Ser Val Lys Asp Arg Phe Thr Ile Ser Arg Asp Asp
1               5                   10                  15

Ser Gln Ser Met Leu His Leu Gln Met Asn Asn Leu Lys Thr Glu Asp
            20                  25                  30

Thr Ala Met Tyr Tyr Cys Val Arg
        35                  40

<210> SEQ ID NO 76
<211> LENGTH: 11
<212> TYPE: PRT
<213> ORGANISM: Artificial Sequence
<220> FEATURE:
<223> OTHER INFORMATION: SEQ ID NO:77

<400> SEQUENCE: 76

Trp Gly Gln Gly Thr Ser Val Thr Val Ser Ser
1               5                   10

<210> SEQ ID NO 77
<211> LENGTH: 26
<212> TYPE: PRT
<213> ORGANISM: Artificial Sequence
```

```
<220> FEATURE:
<223> OTHER INFORMATION: Synthetic polypeptide

<400> SEQUENCE: 77

Asp Ile Gln Met Thr Gln Ser Pro Ser Ser Leu Ser Ala Ser Leu Gly
1               5                   10                  15

Glu Arg Val Ser Leu Thr Cys Arg Ala Ser
            20                  25

<210> SEQ ID NO 78
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 78

Leu Gly Trp Leu Gln Gln Lys Pro Asp Gly Thr Ile Lys Arg Leu Ile
1               5                   10                  15

Tyr

<210> SEQ ID NO 79
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 79

Thr Leu Asp Ser Gly Val Pro Lys Arg Phe Ser Gly Ser Arg Ser Gly
1               5                   10                  15

Ser Ala Tyr Ser Leu Thr Ile Ser Ser Leu Glu Ser Glu Asp Phe Ala
            20                  25                  30

Asp Tyr Tyr Cys
        35

<210> SEQ ID NO 80
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 80

Phe Gly Gly Gly Thr Lys Leu Glu Ile Lys
1               5                   10

<210> SEQ ID NO 81
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 81

Ala Thr Met Gly Trp Ser Cys Ile Ile Leu Phe Leu Val Ala Thr Ala
1               5                   10                  15

Thr Gly Val His Ser
            20

<210> SEQ ID NO 82
<211> LENGTH: 18
<212> TYPE: PRT
<213> ORGANISM: Artificial Sequence
```

<220> FEATURE:
<223> OTHER INFORMATION: Synthetic polypeptide

<400> SEQUENCE: 82

Gly Ser Thr Ser Gly Ser Gly Lys Pro Gly Ser Gly Glu Gly Ser Thr
1               5                   10                  15

Lys Gly

<210> SEQ ID NO 83
<211> LENGTH: 2
<212> TYPE: PRT
<213> ORGANISM: Artificial Sequence
<220> FEATURE:
<223> OTHER INFORMATION: Synthetic polypeptide

<400> SEQUENCE: 83

Glu Phe
1

<210> SEQ ID NO 84
<211> LENGTH: 206
<212> TYPE: PRT
<213> ORGANISM: Artificial Sequence
<220> FEATURE:
<223> OTHER INFORMATION: Synthetic polypeptide

<400> SEQUENCE: 84

Leu Phe Pro Pro Lys Pro Lys Asp Thr Leu Met Ile Ser Arg Thr Pro
1               5                   10                  15

Glu Val Thr Cys Val Val Val Asp Val Ser His Glu Asp Pro Glu Val
                20                  25                  30

Lys Phe Asn Trp Tyr Val Asp Gly Val Glu Val His Asn Ala Lys Thr
            35                  40                  45

Lys Pro Arg Glu Glu Gln Tyr Asn Ser Thr Tyr Arg Val Val Ser Val
        50                  55                  60

Leu Thr Val Leu His Gln Asp Trp Leu Asn Gly Lys Glu Tyr Lys Cys
65                  70                  75                  80

Lys Val Ser Asn Lys Ala Leu Pro Ala Pro Ile Glu Lys Thr Ile Ser
                85                  90                  95

Lys Ala Lys Gly Gln Pro Arg Glu Pro Gln Val Tyr Thr Leu Pro Pro
            100                 105                 110

Ser Arg Glu Glu Met Thr Lys Asn Gln Val Ser Leu Thr Cys Leu Val
        115                 120                 125

Lys Gly Phe Tyr Pro Ser Asp Ile Ala Val Glu Trp Glu Ser Asn Gly
    130                 135                 140

Gln Pro Glu Asn Asn Tyr Lys Thr Thr Pro Pro Val Leu Asp Ser Asp
145                 150                 155                 160

Gly Ser Phe Phe Leu Tyr Ser Lys Leu Thr Val Asp Glu Ser Arg Trp
                165                 170                 175

Gln Gln Gly Asn Val Phe Ser Cys Ser Val Met His Glu Ala Leu His
            180                 185                 190

Asn His Tyr Thr Gln Lys Ser Leu Ser Leu Ser Pro Gly Lys
        195                 200                 205

<210> SEQ ID NO 85
<211> LENGTH: 474
<212> TYPE: PRT
<213> ORGANISM: Artificial Sequence
<220> FEATURE:
<223> OTHER INFORMATION: Synthetic polypeptide

<400> SEQUENCE: 85

Ala Thr Met Gly Trp Ser Cys Ile Ile Leu Phe Leu Val Ala Thr Ala
1               5                   10                  15

Thr Gly Val His Ser Asp Ile Val Met Thr Gln Ser His Lys Phe Met
                20                  25                  30

Ser Thr Ser Ile Gly Asp Arg Val Ser Ile Thr Cys Lys Ala Ser Gln
            35                  40                  45

Asp Val Gly His Tyr Val Ala Trp Tyr Gln Gln Lys Pro Gly Gln Ser
        50                  55                  60

Pro Lys Leu Leu Ile Tyr Trp Ala Ser Thr Arg His Thr Gly Val Pro
65                  70                  75                  80

Asp Arg Phe Thr Gly Ser Gly Ser Gly Thr Asp Phe Thr Leu Thr Ile
                85                  90                  95

Ser Asn Val Gln Ser Glu Asp Leu Ala Asp Tyr Phe Cys Gln Gln Tyr
                100                 105                 110

Asn Ile Tyr Pro Trp Thr Phe Gly Gly Gly Ser Lys Leu Ala Ile Lys
            115                 120                 125

Gly Ser Thr Ser Gly Ser Gly Lys Pro Gly Ser Gly Glu Gly Ser Thr
        130                 135                 140

Lys Gly Glu Val Gln Leu Val Glu Ser Gly Gly Asp Leu Val Lys Pro
145                 150                 155                 160

Gly Gly Ser Leu Lys Leu Ser Cys Ala Ala Ser Gly Phe Thr Phe Ser
                165                 170                 175

Asn Tyr Gly Met Ser Trp Val Arg Gln Thr Pro Asp Lys Arg Leu Glu
            180                 185                 190

Trp Val Ala Thr Ile Ser Ser Gly Gly Gly Tyr Thr His Tyr Val Asp
        195                 200                 205

Ser Val Lys Gly Arg Phe Thr Ile Ser Arg Asp Asn Ala Asn His Ile
    210                 215                 220

Leu Tyr Leu Gln Met Ser Ser Leu Asn Ser Glu Asp Thr Ala Met Tyr
225                 230                 235                 240

Tyr Cys Ala Arg His Pro Arg Asp Phe Ser Tyr Ala Met Asp Tyr Trp
                245                 250                 255

Gly Gln Gly Thr Ser Val Thr Val Ser Ser Glu Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn

-continued

```
                      405                410                415
Asn Tyr Lys Thr Thr Pro Pro Val Leu Asp Ser Asp Gly Ser Phe Phe
              420                425                430

Leu Tyr Ser Lys Leu Thr Val Asp Glu Ser Arg Trp Gln Gln Gly Asn
          435                440                445

Val Phe Ser Cys Ser Val Met His Glu Ala Leu His Asn His Tyr Thr
      450                455                460

Gln Lys Ser Leu Ser Leu Ser Pro Gly Lys
465                470

<210> SEQ ID NO 86
<211> LENGTH: 478
<212> TYPE: PRT
<213> ORGANISM: Artificial Sequence
<220> FEATURE:
<223> OTHER INFORMATION: Synthetic polypeptide

<400> SEQUENCE: 86

Ala Thr Met Gly Trp Ser Cys Ile Ile Leu Phe Leu Val Ala Thr Ala
1               5                   10                  15

Thr Gly Val His Ser Asp Ile Val Met Thr Gln Ala Ala Pro Ser Val
            20                  25                  30

Pro Val Thr Pro Gly Glu Ser Val Ser Ile Ser Cys Arg Ser Ser Lys
        35                  40                  45

Ser Leu Leu His Ser Asn Gly Asn Thr Tyr Leu Tyr Trp Phe Leu Gln
    50                  55                  60

Arg Pro Gly Gln Ser Pro Gln Leu Leu Ile Tyr Arg Met Ser Asn Leu
65                  70                  75                  80

Ala Ser Gly Val Pro Asp Arg Phe Ser Gly Ser Gly Ser Gly Thr Ala
                85                  90                  95

Phe Thr Leu Arg Ile Ser Arg Val Glu Ala Glu Asp Val Gly Val Tyr
            100                 105                 110

Tyr Cys Met Gln His Leu Glu Tyr Pro Leu Thr Val Gly Ala Gly Thr
        115                 120                 125

Lys Leu Glu Leu Lys Gly Ser Thr Ser Gly Ser Gly Lys Pro Gly Ser
    130                 135                 140

Gly Glu Gly Ser Thr Lys Gly Gln Val Gln Leu Gln Gln Ser Gly Ala
145                 150                 155                 160

Glu Leu Val Arg Pro Gly Ala Ser Val Lys Leu Ser Cys Lys Ala Leu
                165                 170                 175

Gly Tyr Thr Phe Thr Asp Tyr Glu Met His Trp Val Lys Gln Thr Pro
            180                 185                 190

Val His Gly Leu Glu Trp Ile Gly Ala Ile His Pro Gly Ser Gly Gly
        195                 200                 205

Thr Ala Tyr Asn Gln Lys Phe Lys Gly Lys Ala Thr Leu Thr Ala Asp
    210                 215                 220

Lys Ser Ser Ser Thr Ala Tyr Met Glu Leu Ser Arg Leu Thr Ser Glu
225                 230                 235                 240

Asp Ser Ala Val Tyr Tyr Cys Thr Arg Arg Pro Arg Phe Tyr Gly
                245                 250                 255

Met Asp Tyr Trp Gly Gln Gly Thr Ser Val Thr Val Ser Ser Glu Phe
            260                 265                 270

Leu Phe Pro Pro Lys Pro Lys Asp Thr Leu Met Ile Ser Arg Thr Pro
        275                 280                 285

Glu Val Thr Cys Val Val Val Asp Val Ser His Glu Asp Pro Glu Val
```

-continued

```
        290              295              300

Lys Phe Asn Trp Tyr Val Asp Gly Val Glu Val His Asn Ala Lys Thr
305                  310                315                320

Lys Pro Arg Glu Glu Gln Tyr Asn Ser Thr Tyr Arg Val Val Ser Val
                325              330              335

Leu Thr Val Leu His Gln Asp Trp Leu Asn Gly Lys Glu Tyr Lys Cys
                340              345              350

Lys Val Ser Asn Lys Ala Leu Pro Ala Pro Ile Glu Lys Thr Ile Ser
            355              360              365

Lys Ala Lys Gly Gln Pro Arg Glu Pro Gln Val Tyr Thr Leu Pro Pro
        370              375              380

Ser Arg Glu Glu Met Thr Lys Asn Gln Val Ser Leu Thr Cys Leu Val
385                  390              395              400

Lys Gly Phe Tyr Pro Ser Asp Ile Ala Val Glu Trp Glu Ser Asn Gly
                405              410              415

Gln Pro Glu Asn Asn Tyr Lys Thr Thr Pro Pro Val Leu Asp Ser Asp
                420              425              430

Gly Ser Phe Phe Leu Tyr Ser Lys Leu Thr Val Asp Glu Ser Arg Trp
            435              440              445

Gln Gln Gly Asn Val Phe Ser Cys Ser Val Met His Glu Ala Leu His
        450              455              460

Asn His Tyr Thr Gln Lys Ser Leu Ser Leu Ser Pro Gly Lys
465                  470              475

<210> SEQ ID NO 87
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 87
gccaccatgg gatggtcatg tatcatcctt tttctagtag caactgcaac cggtgtacat      60
tcc                                                                    63

<210> SEQ ID NO 88
<211> LENGTH: 54
<212> TYPE: DNA
<213> ORGANISM: Artificial Sequence
<220> FEATURE:
<223> OTHER INFORMATION: Synthetic polynucleotide

<400> SEQUENCE: 88
ggctccacct ctggatccgg caagcccgga tctggcgagg gatccaccaa gggc            54

<210> SEQ ID NO 89
<211> LENGTH: 6
<212> TYPE: DNA
<213> ORGANISM: Artificial Sequence
<220> FEATURE:
<223> OTHER INFORMATION: Synthetic polynucleotide

<400> SEQUENCE: 89 gaattc                                                                  6

<210> SEQ ID NO 90
<211> LENGTH: 621
<212> TYPE: DNA
<213> ORGANISM: Artificial Sequence
<220> FEATURE:
```

<223> OTHER INFORMATION: Synthetic polynucleotide

<400> SEQUENCE: 90

```
ctcttccccc caaaacccaa ggacaccctc atgatctccc ggacccctga ggtcacatgc      60
gtggtggtgg acgtgagcca cgaagaccct gaggtcaagt tcaactggta cgtggacggc     120
gtggaggtgc ataatgccaa gacaaagccg cgggaggagc agtacaacag cacgtaccgt     180
gtggtcagcg tcctcaccgt cctgcaccag gactggctga atggcaagga gtacaagtgc     240
aaggtctcca acaaagccct cccagccccc atcgagaaaa ccatctccaa agccaaaggg     300
cagccccgag aaccacaggt gtacaccctg cccccatccc gggaggagat gaccaagaac     360
caggtcagcc tgacctgcct ggtcaaaggc ttctatccca gcgacatcgc cgtggagtgg     420
gagagcaatg ggcagccgga gaacaactac aagaccacgc ctcccgtgct ggactccgac     480
ggctccttct tcctctatag caagctcacc gtggacgaga gcaggtggca gcaggggaac     540
gtcttctcat gctccgtgat gcatgaggct ctgcacaacc actacacgca gaagagcctc     600
tccctgtctc cgggtaaatg a                                              621
```

<210> SEQ ID NO 91
<211> LENGTH: 1425
<212> TYPE: DNA
<213> ORGANISM: Artificial Sequence
<220> FEATURE:
<223> OTHER INFORMATION: Synthetic polynucleotide

<400> SEQUENCE: 91

```
gccaccatgg gatggtcatg tatcatcctt tttctagtag caactgcaac cggtgtacat      60
tccgacattg tgatgaccca gtctcacaaa ttcatgtcca catcaatagg agacagggtc     120
agcatcacct gcaaggccag tcaggatgtg ggtcattatg tggcctggta tcaacagaaa     180
ccaggtcaat ctcctaaact actgatttac tgggcatcca cccggcacac tggagtccct     240
gatcgcttca caggtagtgg atctgggaca gatttcactc tcaccattag caatgtgcag     300
tctgaagact ggcagatta tttctgtcag caatataaca tctatccgtg acgttcggt     360 ggaggctcca agctggcaat caaaggctcc acctctggat ccggcaagcc cggatctggc     420
gagggatcta ccaagggcga ggtgcagctg gtggagtctg ggggagactt agtgaagcct     480
ggagggtccc tgaaactctc ctgtgcagcc tctggattca ctttcagtaa ttatggcatg     540
tcttgggttc gccagactcc agacaagagg ctggagtggg tcgcaaccat tagtagtggt     600
ggtggttaca ctcactatgt agacagtgtg aaggggcgat tcaccatttc cagagacaat     660
gccaaccata tcctgtacct gcaaatgagc agtctgaact ctgaggacac agccatgtat     720
tattgtgcaa gacacccgag ggattttttcc tatgctatgg actactgggg tcagggaacc     780
tcagtcaccg tctcctcaga attcctcttc cccccaaaac ccaaggacac cctcatgatc     840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggagg agatgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct atagcaagct caccgtggac    1320
```

```
gagagcaggt ggcagcaggg gaacgtcttc tcatgctccg tgatgcatga ggctctgcac      1380
aaccactaca cgcagaagag cctctccctg tctccgggta aatga                       1425
```

<210> SEQ ID NO 92
<211> LENGTH: 1437
<212> TYPE: DNA
<213> ORGANISM: Artificial Sequence
<220> FEATURE:
<223> OTHER INFORMATION: Synthetic polynucleotide

<400> SEQUENCE: 92

```
gccaccatgg gatggtcatg tatcatcctt tttctagtag caactgcaac cggtgtacat       60
tccgatattg tgatgactca ggctgcaccc tctgtacctg tcactcctgg agagtcagta      120
tccatctcct gcaggtctag taagagtctc ctgcatagta atggcaacac ttacttgtat      180
tggttcctgc agaggccagg ccagtctcct cagctcctga tatatcggat gtccaacctt      240
gcctcaggag tcccagacag gttcagtggc agtgggtcag gaactgcttt cacactgaga      300
atcagtagag tggaggctga ggatgtgggt gtttattact gtatgcaaca tctagaatat      360
cctctcacgg tcggtgctgg gaccaagctg gagctgaaag ctccacctc tggatccggc       420 aagcccggat ctggcgaggg atctaccaag ggccaggttc aactgcaaca gtctggggct      480
gagctggtga ggcctggggc ttcagtgaag ctgtcctgca aggctttggg ctacacattt      540
actgactatg aaatgcactg ggtgaagcag acacctgtgc atggcctgga atggattgga      600
gctattcatc caggaagtgg tggtactgcc tataatcaga agttcaaggg caaggccaca      660
ctgactgcag acaaatcctc cagcacagcc tacatggagc tcagcaggct gacatctgag      720
gactctgctg tctattactg tacaagaagg aggcctaggt tctatggtat ggactactgg      780
ggtcaaggaa cctcagtcac cgtctcctca gaattcctct tccccccaaa acccaaggac      840
accctcatga tctcccggac ccctgaggtc acatgcgtgg tggtggacgt gagccacgaa      900
gaccctgagg tcaagttcaa ctggtacgtg gacggcgtgg aggtgcataa tgccaagaca      960
aagccgcggg aggagcagta caacagcacg taccgtgtgg tcagcgtcct caccgtcctg     1020
caccaggact ggctgaatgg caaggagtac aagtgcaagg tctccaacaa agccctccca     1080
gcccccatcg agaaaaccat ctccaaagcc aaagggcagc cccgagaacc acaggtgtac     1140
accctgcccc catcccggga ggagatgacc aagaaccagg tcagcctgac ctgcctggtc     1200
aaaggcttct atcccagcga catcgccgtg gagtgggaga gcaatgggca gccggagaac     1260
aactacaaga ccacgcctcc cgtgctggac tccgacggct ccttcttcct ctatagcaag     1320
ctcaccgtgg acgagagcag gtggcagcag gggaacgtct tctcatgctc cgtgatgcat     1380
gaggctctgc acaaccacta cacgcagaag agcctctccc tgtctccggg taaatga        1437
```

<210> SEQ ID NO 93
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 93

```
Met Gly Trp Ser Cys Ile Ile Leu Phe Leu Val Ala Thr Ala Thr Gly
1               5                   10                  15

Val His Ser
```

```
<210> SEQ ID NO 94
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 94

Val Asp Glu Ser Lys Tyr Gly Pro Pro Cys Pro Pro Cys Pro
1               5               10

<210> SEQ ID NO 95
<211> LENGTH: 147
<212> TYPE: PRT
<213> ORGANISM: Artificial Sequence
<220> FEATURE:
<223> OTHER INFORMATION: SEQ ID NO:96

<400> SEQUENCE: 95

Val Asp Glu Ser Lys Tyr Gly Pro Pro Cys Pro Pro Cys Pro Gly Lys
1               5               10              15

Glu Tyr Lys Cys Lys Val Ser Asn Lys Gly Leu Pro Ser Ser Ile Glu
            20              25              30

Lys Thr Ile Ser Lys Ala Lys Gly Gln Pro Arg Glu Pro Gln Val Tyr
        35              40              45

Thr Leu Pro Pro Ser Gln Glu Glu Met Thr Lys Asn Gln Val Ser Leu
    50              55              60

Thr Cys Leu Val Lys Gly Phe Tyr Pro Ser Asp Ile Ala Val Glu Trp
65              70              75              80

Glu Ser Asn Gly Gln Pro Glu Asn Asn Tyr Lys Thr Thr Pro Pro Val
            85              90              95

Leu Asp Ser Asp Gly Ser Phe Phe Leu Tyr Ser Arg Leu Thr Val Asp
            100             105             110

Lys Ser Arg Trp Gln Glu Gly Asn Val Phe Ser Cys Ser Val Met His
        115             120             125

Glu Ala Leu His Asn His Tyr Thr Gln Lys Ser Leu Ser Leu Ser Leu
    130             135             140

Gly Lys Met
145

<210> SEQ ID NO 96
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 96

Val Asp Glu Ser Lys Tyr Gly Pro Pro Cys Pro Pro Cys Pro Ala Pro
1               5               10              15

Glu Phe Leu Gly Gly Pro Ser Val Phe Leu Phe Pro Pro Lys Pro Lys
            20              25              30

Asp Thr Leu Met Ile Ser Arg Thr Pro Glu Val Thr Cys Val Val Val
        35              40              45

Asp Val Ser Gln Glu Asp Pro Glu Val Gln Phe Asn Trp Tyr Val Asp
    50              55              60

Gly Val Glu Val His Asn Ala Lys Thr Lys Pro Arg Glu Glu Gln Phe
65              70              75              80

Asn Ser Thr Tyr Arg Val Val Ser Val Leu Thr Val Leu His Gln Asp
            85              90              95
```

```
Trp Leu Asn Gly Lys Glu Tyr Lys Cys Lys Val Ser Asn Lys Gly Leu
            100                 105                 110

Pro Ser Ser Ile Glu Lys Thr Ile Ser Lys Ala Lys Gly Gln Pro Arg
            115                 120                 125

Glu Pro Gln Val Tyr Thr Leu Pro Pro Ser Gln Glu Glu Met Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Arg Leu Thr Val Asp Lys Ser Arg Trp Gln Glu Gly Asn Val Phe Ser
            195                 200                 205

Cys Ser Val Met His Glu Ala Leu His Asn His Tyr Thr Gln Lys Ser
    210                 215                 220

Leu Ser Leu Ser Leu Gly Lys Met
225                 230
```

<210> SEQ ID NO 97
<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 97

```
Phe Trp Val Leu Val Val Val Gly Gly Val Leu Ala Cys Tyr Ser Leu
1                   5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
    50                  55                  60

Ala Tyr Arg Ser
65
```

<210> SEQ ID NO 98
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 98

```
Lys Arg Gly Arg Lys Lys Leu Leu Tyr Ile Phe Lys Gln Pro Phe Met
1                   5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 99
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 99

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
            50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110
```

<210> SEQ ID NO 100
<211> LENGTH: 718
<212> TYPE: PRT
<213> ORGANISM: Artificial Sequence
<220> FEATURE:
<223> OTHER INFORMATION: Synthetic polypeptide

<400> SEQUENCE: 100

```
Met Gly Trp Ser Cys Ile Ile Leu Phe Leu Val Ala Thr Ala Thr Gly
1               5                   10                  15

Val His Ser Asp Ile Val Met Thr Gln Ser His Lys Phe Met Ser Thr
                20                  25                  30

Ser Ile Gly Asp Arg Val Ser Ile Thr Cys Lys Ala Ser Gln Asp Val
            35                  40                  45

Gly His Tyr Val Ala Trp Tyr Gln Gln Lys Pro Gly Gln Ser Pro Lys
            50                  55                  60

Leu Leu Ile Tyr Trp Ala Ser Thr Arg His Thr Gly Val Pro Asp Arg
65                  70                  75                  80

Phe Thr Gly Ser Gly Ser Gly Thr Asp Phe Thr Leu Thr Ile Ser Asn
                85                  90                  95

Val Gln Ser Glu Asp Leu Ala Asp Tyr Phe Cys Gln Gln Tyr Asn Ile
                100                 105                 110

Tyr Pro Trp Thr Phe Gly Gly Gly Ser Lys Leu Ala Ile Lys Gly Ser
            115                 120                 125

Thr Ser Gly Ser Gly Lys Pro Gly Ser Gly Glu Gly Ser Thr Lys Gly
            130                 135                 140

Glu Val Gln Leu Val Glu Ser Gly Gly Asp Leu Val Lys Pro Gly Gly
145                 150                 155                 160

Ser Leu Lys Leu Ser Cys Ala Ala Ser Gly Phe Thr Phe Ser Asn Tyr
                165                 170                 175

Gly Met Ser Trp Val Arg Gln Thr Pro Asp Lys Arg Leu Glu Trp Val
                180                 185                 190

Ala Thr Ile Ser Ser Gly Gly Gly Tyr Thr His Tyr Val Asp Ser Val
            195                 200                 205

Lys Gly Arg Phe Thr Ile Ser Arg Asp Asn Ala Asn His Ile Leu Tyr
            210                 215                 220

Leu Gln Met Ser Ser Leu Asn Ser Glu Asp Thr Ala Met Tyr Tyr Cys
225                 230                 235                 240
```

-continued

```
Ala Arg His Pro Arg Asp Phe Ser Tyr Ala Met Asp Tyr Trp Gly Gln
            245                 250                 255

Gly Thr Ser Val Thr Val Ser Ser Val Asp Glu Ser Lys Tyr Gly Pro
            260                 265                 270

Pro Cys Pro Pro Cys Pro Ala Pro Glu Phe Leu Gly Gly Pro Ser Val
            275                 280                 285

Phe Leu Phe Pro Pro Lys Pro Lys Asp Thr Leu Met Ile Ser Arg Thr
    290                 295                 300

Pro Glu Val Thr Cys Val Val Val Asp Val Ser Gln Glu Asp Pro Glu
305                 310                 315                 320

Val Gln Phe Asn Trp Tyr Val Asp Gly Val Glu Val His Asn Ala Lys
                325                 330                 335

Thr Lys Pro Arg Glu Glu Gln Phe Asn Ser Thr Tyr Arg Val Val Ser
            340                 345                 350

Val Leu Thr Val Leu His Gln Asp Trp Leu Asn Gly Lys Glu Tyr Lys
            355                 360                 365

Cys Lys Val Ser Asn Lys Gly Leu Pro Ser Ser Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Gln Glu Glu Met Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
            435                 440                 445

Asp Gly Ser Phe Phe Leu Tyr Ser Arg Leu Thr Val Asp Lys Ser Arg
    450                 455                 460

Trp Gln Glu Gly Asn Val Phe Ser Cys Ser Val Met His Glu Ala Leu
465                 470                 475                 480

His Asn His Tyr Thr Gln Lys Ser Leu Ser Leu Ser Leu Gly Lys Met
                485                 490                 495

Phe Trp Val Leu Val Val Val Gly Gly Val Leu Ala Cys Tyr Ser Leu
            500                 505                 510

Leu Val Thr Val Ala Phe Ile Ile Phe Trp Val Arg Ser Lys Arg Ser
            515                 520                 525

Arg Gly Gly His Ser Asp Tyr Met Asn Met Thr Pro Arg Arg Pro Gly
    530                 535                 540

Pro Thr Arg Lys His Tyr Gln Pro Tyr Ala Pro Pro Arg Asp Phe Ala
545                 550                 555                 560

Ala Tyr Arg Ser Lys Arg Gly Arg Lys Lys Leu Leu Tyr Ile Phe Lys
                565                 570                 575

Gln Pro Phe Met Arg Pro Val Gln Thr Thr Gln Glu Glu Asp Gly Cys
            580                 585                 590

Ser Cys Arg Phe Pro Glu Glu Glu Gly Gly Cys Glu Leu Arg Val
            595                 600                 605

Lys Phe Ser Arg Ser Ala Asp Ala Pro Ala Tyr Gln Gln Gly Gln Asn
    610                 615                 620

Gln Leu Tyr Asn Glu Leu Asn Leu Gly Arg Arg Glu Glu Tyr Asp Val
625                 630                 635                 640

Leu Asp Lys Arg Arg Gly Arg Asp Pro Glu Met Gly Gly Lys Pro Arg
                645                 650                 655

Arg Lys Asn Pro Gln Glu Gly Leu Tyr Asn Glu Leu Gln Lys Asp Lys
```

-continued

```
            660              665              670
Met Ala Glu Ala Tyr Ser Glu Ile Gly Met Lys Gly Glu Arg Arg Arg
        675              680              685

Gly Lys Gly His Asp Gly Leu Tyr Gln Gly Leu Ser Thr Ala Thr Lys
    690              695              700

Asp Thr Tyr Asp Ala Leu His Met Gln Ala Leu Pro Pro Arg
705              710              715
```

<210> SEQ ID NO 101
<211> LENGTH: 722
<212> TYPE: PRT
<213> ORGANISM: Artificial Sequence
<220> FEATURE:
<223> OTHER INFORMATION: Synthetic polypeptide

<400> SEQUENCE: 101

```
Met Gly Trp Ser Cys Ile Ile Leu Phe Leu Val Ala Thr Ala Thr Gly
1               5               10              15

Val His Ser Asp Ile Val Met Thr Gln Ala Ala Pro Ser Val Pro Val
            20              25              30

Thr Pro Gly Glu Ser Val Ser Ile Ser Cys Arg Ser Ser Lys Ser Leu
        35              40              45

Leu His Ser Asn Gly Asn Thr Tyr Leu Tyr Trp Phe Leu Gln Arg Pro
    50              55              60

Gly Gln Ser Pro Gln Leu Leu Ile Tyr Arg Met Ser Asn Leu Ala Ser
65              70              75              80

Gly Val Pro Asp Arg Phe Ser Gly Ser Gly Ser Gly Thr Ala Phe Thr
            85              90              95

Leu Arg Ile Ser Arg Val Glu Ala Glu Asp Val Gly Val Tyr Tyr Cys
        100             105             110

Met Gln His Leu Glu Tyr Pro Leu Thr Val Gly Ala Gly Thr Lys Leu
    115             120             125

Glu Leu Lys Gly Ser Thr Ser Gly Ser Gly Lys Pro Gly Ser Gly Glu
    130             135             140

Gly Ser Thr Lys Gly Gln Val Gln Leu Gln Gln Ser Gly Ala Glu Leu
145             150             155             160

Val Arg Pro Gly Ala Ser Val Lys Leu Ser Cys Lys Ala Leu Gly Tyr
            165             170             175

Thr Phe Thr Asp Tyr Glu Met His Trp Val Lys Gln Thr Pro Val His
            180             185             190

Gly Leu Glu Trp Ile Gly Ala Ile His Pro Gly Ser Gly Gly Thr Ala
    195             200             205

Tyr Asn Gln Lys Phe Lys Gly Lys Ala Thr Leu Thr Ala Asp Lys Ser
    210             215             220

Ser Ser Thr Ala Tyr Met Glu Leu Ser Arg Leu Thr Ser Glu Asp Ser
225             230             235             240

Ala Val Tyr Tyr Cys Thr Arg Arg Pro Arg Phe Tyr Gly Met Asp
            245             250             255

Tyr Trp Gly Gln Gly Thr Ser Val Thr Val Ser Ser Val Asp Glu Ser
            260             265             270

Lys Tyr Gly Pro Pro Cys Pro Pro Cys Pro Ala Pro Glu Phe Leu Gly
        275             280             285

Gly Pro Ser Val Phe Leu Phe Pro Pro Lys Pro Lys Asp Thr Leu Met
    290             295             300

Ile Ser Arg Thr Pro Glu Val Thr Cys Val Val Val Asp Val Ser Gln
```

-continued

```
305              310              315              320

Glu Asp Pro Glu Val Gln Phe Asn Trp Tyr Val Asp Gly Val Glu Val
                325              330              335

His Asn Ala Lys Thr Lys Pro Arg Glu Glu Gln Phe Asn Ser Thr Tyr
                340              345              350

Arg Val Val Ser Val Leu Thr Val Leu His Gln Asp Trp Leu Asn Gly
                355              360              365

Lys Glu Tyr Lys Cys Lys Val Ser Asn Lys Gly Leu Pro Ser Ser Ile
        370              375              380

Glu Lys Thr Ile Ser Lys Ala Lys Gly Gln Pro Arg Glu Pro Gln Val
385              390              395              400

Tyr Thr Leu Pro Pro Ser Gln Glu Glu Met Thr Lys Asn Gln Val Ser
                405              410              415

Leu Thr Cys Leu Val Lys Gly Phe Tyr Pro Ser Asp Ile Ala Val Glu
                420              425              430

Trp Glu Ser Asn Gly Gln Pro Glu Asn Asn Tyr Lys Thr Thr Pro Pro
        435              440              445

Val Leu Asp Ser Asp Gly Ser Phe Phe Leu Tyr Ser Arg Leu Thr Val
        450              455              460

Asp Lys Ser Arg Trp Gln Glu Gly Asn Val Phe Ser Cys Ser Val Met
465              470              475              480

His Glu Ala Leu His Asn His Tyr Thr Gln Lys Ser Leu Ser Leu Ser
                485              490              495

Leu Gly Lys Met Phe Trp Val Leu Val Val Val Gly Gly Val Leu Ala
                500              505              510

Cys Tyr Ser Leu Leu Val Thr Val Ala Phe Ile Ile Phe Trp Val Arg
                515              520              525

Ser Lys Arg Ser Arg Gly Gly His Ser Asp Tyr Met Asn Met Thr Pro
        530              535              540

Arg Arg Pro Gly Pro Thr Arg Lys His Tyr Gln Pro Tyr Ala Pro Pro
545              550              555              560

Arg Asp Phe Ala Ala Tyr Arg Ser Lys Arg Gly Arg Lys Lys Leu Leu
                565              570              575

Tyr Ile Phe Lys Gln Pro Phe Met Arg Pro Val Gln Thr Thr Gln Glu
                580              585              590

Glu Asp Gly Cys Ser Cys Arg Phe Pro Glu Glu Glu Glu Gly Gly Cys
                595              600              605

Glu Leu Arg Val Lys Phe Ser Arg Ser Ala Asp Ala Pro Ala Tyr Gln
        610              615              620

Gln Gly Gln Asn Gln Leu Tyr Asn Glu Leu Asn Leu Gly Arg Arg Glu
625              630              635              640

Glu Tyr Asp Val Leu Asp Lys Arg Arg Gly Arg Asp Pro Glu Met Gly
                645              650              655

Gly Lys Pro Arg Arg Lys Asn Pro Gln Glu Gly Leu Tyr Asn Glu Leu
                660              665              670

Gln Lys Asp Lys Met Ala Glu Ala Tyr Ser Glu Ile Gly Met Lys Gly
        675              680              685

Glu Arg Arg Arg Gly Lys Gly His Asp Gly Leu Tyr Gln Gly Leu Ser
        690              695              700

Thr Ala Thr Lys Asp Thr Tyr Asp Ala Leu His Met Gln Ala Leu Pro
705              710              715              720

Pro Arg
```

<210> SEQ ID NO 102
<211> LENGTH: 634
<212> TYPE: PRT
<213> ORGANISM: Artificial Sequence
<220> FEATURE:
<223> OTHER INFORMATION: Synthetic polypeptide

<400> SEQUENCE: 102

Met Ala Arg Gly Ser Ala Leu Pro Arg Pro Leu Leu Cys Ile Pro
1               5                   10                  15

Ala Val Trp Ala Ala Ala Leu Leu Leu Ser Val Ser Arg Thr Ser
                20                  25                  30

Gly Glu Val Glu Val Leu Asp Pro Asn Asp Pro Leu Gly Pro Leu Asp
            35                  40                  45

Gly Gln Asp Gly Pro Ile Pro Thr Leu Lys Gly Tyr Phe Leu Asn Phe
        50                  55                  60

Leu Glu Pro Val Asn Asn Ile Thr Ile Val Gln Gly Gln Thr Ala Ile
65                  70                  75                  80

Leu His Cys Lys Val Ala Gly Asn Pro Pro Pro Asn Val Arg Trp Leu
                85                  90                  95

Lys Asn Asp Ala Pro Val Val Gln Glu Pro Arg Arg Ile Ile Ile Arg
                100                 105                 110

Lys Thr Glu Tyr Gly Ser Arg Leu Arg Ile Gln Asp Leu Asp Thr Thr
                115                 120                 125

Asp Thr Gly Tyr Tyr Gln Cys Val Ala Thr Asn Gly Met Lys Thr Ile
            130                 135                 140

Thr Ala Thr Gly Val Leu Phe Val Arg Leu Gly Pro Thr His Ser Pro
145                 150                 155                 160

Asn His Asn Phe Gln Asp Asp Tyr His Glu Asp Gly Phe Cys Gln Pro
                165                 170                 175

Tyr Arg Gly Ile Ala Cys Ala Arg Phe Ile Gly Asn Arg Thr Ile Tyr
                180                 185                 190

Val Asp Ser Leu Gln Met Gln Gly Glu Ile Glu Asn Arg Ile Thr Ala
            195                 200                 205

Ala Phe Thr Met Ile Gly Thr Ser Thr His Leu Ser Asp Gln Cys Ser
        210                 215                 220

Gln Phe Ala Ile Pro Ser Phe Cys His Phe Val Phe Pro Leu Cys Asp
225                 230                 235                 240

Ala Arg Ser Arg Thr Pro Lys Pro Arg Glu Leu Cys Arg Asp Glu Cys
                245                 250                 255

Glu Val Leu Glu Ser Asp Leu Cys Arg Gln Glu Tyr Thr Ile Ala Arg
                260                 265                 270

Ser Asn Pro Leu Ile Leu Met Arg Leu Gln Leu Pro Lys Cys Glu Ala
            275                 280                 285

Leu Pro Met Pro Glu Ser Pro Asp Ala Ala Asn Cys Met Arg Ile Gly
        290                 295                 300

Ile Pro Ala Glu Arg Leu Gly Arg Tyr His Gln Cys Tyr Asn Gly Ser
305                 310                 315                 320

Gly Met Asp Tyr Arg Gly Thr Ala Ser Thr Thr Lys Ser Gly His Gln
                325                 330                 335

Cys Gln Pro Trp Ala Leu Gln His Pro His Ser His His Leu Ser Ser
            340                 345                 350

Thr Asp Phe Pro Glu Leu Gly Gly Gly His Ala Tyr Cys Arg Asn Pro
            355                 360                 365

```
Gly Gly Gln Met Glu Gly Pro Trp Cys Phe Thr Gln Asn Lys Asn Val
    370             375                 380

Arg Met Glu Leu Cys Asp Val Pro Ser Cys Ser Pro Arg Asp Ser Ser
385             390                 395                 400

Lys Met Gly Pro Lys Ser Cys Asp Lys Thr His Thr Cys Pro Pro Cys
                405                 410                 415

Pro Ala Pro Glu Leu Leu Gly Gly Pro Ser Val Phe Leu Phe Pro Pro
                420                 425                 430

Lys Pro Lys Asp Thr Leu Met Ile Ser Arg Thr Pro Glu Val Thr Cys
                435                 440                 445

Val Val Val Asp Val Ser His Glu Asp Pro Glu Val Lys Phe Asn Trp
    450                 455                 460

Tyr Val Asp Gly Val Glu Val His Asn Ala Lys Thr Lys Pro Arg Glu
465                 470                 475                 480

Glu Gln Tyr Asn Ser Thr Tyr Arg Val Val Ser Val Leu Thr Val Leu
                485                 490                 495

His Gln Asp Trp Leu Asn Gly Lys Glu Tyr Lys Cys Lys Val Ser Asn
                500                 505                 510

Lys Ala Leu Pro Ala Pro Ile Glu Lys Thr Ile Ser Lys Ala Lys Gly
                515                 520                 525

Gln Pro Arg Glu Pro Gln Val Tyr Thr Leu Pro Pro Ser Arg Asp Glu
    530                 535                 540

Leu Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
                580                 585                 590

Leu Tyr Ser Lys Leu Thr Val Asp Lys Ser Arg Trp Gln Gln Gly Asn
                595                 600                 605

Val Phe Ser Cys Ser Val Met His Glu Ala Leu His Asn His Tyr Thr
    610                 615                 620

Gln Lys Ser Leu Ser Leu Ser Pro Gly Lys
625                 630
```

```
<210> SEQ ID NO 103
<211> LENGTH: 634
<212> TYPE: PRT
<213> ORGANISM: Artificial Sequence
<220> FEATURE:
<223> OTHER INFORMATION: Synthetic polypeptide

<400> SEQUENCE: 103
```

```
Met His Arg Pro Arg Arg Arg Gly Thr Arg Pro Pro Leu Leu Ala Leu
1               5                   10                  15

Leu Ala Ala Leu Leu Leu Ala Ala Arg Gly Ala Ala Ala Gln Glu Thr
                20                  25                  30

Glu Leu Ser Val Ser Ala Glu Leu Val Pro Thr Ser Ser Trp Asn Ile
                35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Pro Thr Ile Arg Trp Phe Lys Asn Asp Ala
                85                  90                  95
```

```
Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
            115                 120                 125

Phe Gln Cys Val Ala Thr Asn Gly Lys Glu Val Val Ser Ser Thr Gly
            130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
            195                 200                 205

Ile Gly Thr Ser Ser His Leu Ser Asp Lys Cys Ser Gln Phe Ala Ile
            210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
            275                 280                 285

Glu Ser Pro Glu Ala Ala Asn Cys Ile Arg Ile Gly Ile Pro Met Ala
            290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
            355                 360                 365

Lys Glu Ala Pro Trp Cys Phe Thr Leu Asp Glu Asn Phe Lys Ser Asp
    370                 375                 380

Leu Cys Asp Ile Pro Ala Cys Asp Ser Lys Asp Ser Lys Glu Lys Asn
385                 390                 395                 400

Lys Met Glu Pro Lys Ser Cys Asp Lys Thr His Thr Cys Pro Pro Cys
                405                 410                 415

Pro Ala Pro Glu Leu Leu Gly Gly Pro Ser Val Phe Leu Phe Pro Pro
                420                 425                 430

Lys Pro Lys Asp Thr Leu Met Ile Ser Arg Thr Pro Glu Val Thr Cys
            435                 440                 445

Val Val Val Asp Val Ser His Glu Asp Pro Glu Val Lys Phe Asn Trp
            450                 455                 460

Tyr Val Asp Gly Val Glu Val His Asn Ala Lys Thr Lys Pro Arg Glu
465                 470                 475                 480

Glu Gln Tyr Asn Ser Thr Tyr Arg Val Val Ser Val Leu Thr Val Leu
                485                 490                 495

His Gln Asp Trp Leu Asn Gly Lys Glu Tyr Lys Cys Lys Val Ser Asn
            500                 505                 510

Lys Ala Leu Pro Ala Pro Ile Glu Lys Thr Ile Ser Lys Ala Lys Gly
```

```
            515                 520                 525

Gln Pro Arg Glu Pro Gln Val Tyr Thr Leu Pro Pro Ser Arg Asp Glu
    530                 535                 540

Leu Thr Lys Asn Gln Val Ser Leu Thr Cys Leu Val Lys Gly Phe Tyr
545                 550                 555                 560

Pro Ser Asp Ile Ala Val Glu Trp Glu Ser Asn Gly Gln Pro Glu Asn
                565                 570                 575

Asn Tyr Lys Thr Thr Pro Pro Val Leu Asp Ser Asp Gly Ser Phe Phe
                580                 585                 590

Leu Tyr Ser Lys Leu Thr Val Asp Lys Ser Arg Trp Gln Gln Gly Asn
            595                 600                 605

Val Phe Ser Cys Ser Val Met His Glu Ala Leu His Asn His Tyr Thr
    610                 615                 620

Gln Lys Ser Leu Ser Leu Ser Pro Gly Lys
625                 630
```

```
<210> SEQ ID NO 104
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 104
atgggatggt catgtatcat cctttttcta gtagcaactg caaccggtgt acattcc          57

<210> SEQ ID NO 105
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 105
gtcgacgagt ccaaatatgg tcccccatgc ccaccatgcc ca                          42

<210> SEQ ID NO 106
<211> LENGTH: 441
<212> TYPE: DNA
<213> ORGANISM: Artificial Sequence
<220> FEATURE:
<223> OTHER INFORMATION: Synthetic polynucleotide

<400> SEQUENCE: 106
gtcgacgagt ccaaatatgg tcccccatgc ccaccatgcc caggcaagga gtacaagtgc       60
aaggtctcca acaaaggcct cccgtcctcc atcgagaaaa ccatctccaa agccaaaggg      120
cagccccgag agccacaggt gtacaccctg cccccatccc aggaggagat gaccaagaac      180
caggtcagcc tgacctgcct ggtcaaaggc ttctacccca gcgacatcgc cgtggagtgg      240
gagagcaatg ggcagccgga gaacaactac aagaccacgc ctcccgtgct ggactccgac      300
ggctccttct tcctctacag caggctaacc gtggacaaga gcaggtggca ggaggggaat      360
gtcttctcat gctccgtgat gcatgaggct ctgcacaacc actacacaca gaagagcctc      420
tccctgtccc taggtaaaat g                                              441

<210> SEQ ID NO 107
<211> LENGTH: 696
<212> TYPE: DNA
<213> ORGANISM: Artificial Sequence
<220> FEATURE:
```

<223> OTHER INFORMATION: Synthetic polynucleotide

<400> SEQUENCE: 107
gtcgacgagt ccaaatatgg tcccccatgc ccaccatgcc cagcacctga gttcctgggg      60
ggaccatcag tcttcctgtt ccccccaaaa cccaaggaca ctctcatgat ctcccggacc     120
cctgaggtca cgtgcgtggt ggtggacgtg agccaggaag accccgaggt ccagttcaac     180
tggtacgtgg atggcgtgga ggtgcataat gccaagacaa agccgcggga ggagcagttc     240
aacagcacgt accgtgtggt cagcgtcctc accgtcctgc accaggactg gctgaacggc     300
aaggagtaca gtgcaaggt ctccaacaaa ggcctcccgt cctccatcga gaaaaccatc     360
tccaaagcca aagggcagcc ccgagagcca caggtgtaca ccctgccccc atcccaggag     420
gagatgacca gaaccaggt cagcctgacc tgcctggtca aaggcttcta ccccagcgac     480
atcgccgtgg agtgggagag caatgggcag ccggagaaca actacaagac cacgcctccc     540
gtgctggact ccgacggctc cttcttcctc tacagcaggc taaccgtgga caagagcagg     600
tggcaggagg ggaatgtctt ctcatgctcc gtgatgcatg aggctctgca caaccactac     660
acacagaaga gcctctccct gtccctaggt aaaatg                                696

<210> SEQ ID NO 108
<211> LENGTH: 204
<212> TYPE: DNA
<213> ORGANISM: Artificial Sequence
<220> FEATURE:
<223> OTHER INFORMATION: Synthetic polynucleotide

<400> SEQUENCE: 108
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc cccgccgccc cgggcccacc cgcaagcatt accagcccta tgccccacca     180
cgcgacttcg cagcctatcg ctcc                                             204

<210> SEQ ID NO 109
<211> LENGTH: 126
<212> TYPE: DNA
<213> ORGANISM: Artificial Sequence
<220> FEATURE:
<223> OTHER INFORMATION: Synthetic polynucleotide

<400> SEQUENCE: 109
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                 126

<210> SEQ ID NO 110
<211> LENGTH: 339
<212> TYPE: DNA
<213> ORGANISM: Artificial Sequence
<220> FEATURE:
<223> OTHER INFORMATION: Synthetic polynucleotide

<400> SEQUENCE: 110
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg agatgggggg aaagccgaga aggaagaacc ctcaggaagg cctgtacaat     180
gaactgcaga aagataagat ggcggaggcc tacagtgaga ttgggatgaa aggcgagcgc     240

-continued

```
cggaggggca aggggcacga tggcctttac cagggtctca gtacagccac caaggacacc      300
tacgacgccc ttcacatgca ggccctgccc cctcgctga                            339

<210> SEQ ID NO 111
<211> LENGTH: 2157
<212> TYPE: DNA
<213> ORGANISM: Artificial Sequence
<220> FEATURE:
<223> OTHER INFORMATION: Synthetic polynucleotide

<400> SEQUENCE: 111
atgggatggt catgtatcat cctttttcta gtagcaactg caaccggtgt acattccgac       60
attgtgatga cccagtctca caaattcatg tccacatcaa taggagacag ggtcagcatc      120
acctgcaagg ccagtcagga tgtgggtcat tatgtggcct ggtatcaaca gaaaccaggt      180
caatctccta aactactgat ttactgggca tccacccggc acactggagt ccctgatcgc      240
ttcacaggta gtggatctgg gacagatttc actctcacca ttagcaatgt gcagtctgaa      300
gacttggcag attatttctg tcagcaatat aacatctatc cgtggacgtt cggtggaggc      360
tccaagctgg caatcaaagg ctccacctct ggatccggca gcccggatc tggcgaggga      420 tccaccaagg gcgaggtgca gctggtggag tctgggggag acttagtgaa gcctggaggg      480
tccctgaaac tctcctgtgc agcctctgga ttcactttca gtaattatgg catgtcttgg      540
gttcgccaga ctccagacaa gaggctggag tgggtcgcaa ccattagtag tggtggtggt      600
tacactcact atgtagacag tgtgaagggg cgattcacca tttccagaga caatgccaac      660
catatcctgt acctgcaaat gagcagtctg aactctgagg acacagccat gtattattgt      720
gcaagacacc cgagggattt ttcctatgct atggactact ggggtcaggg aacctcagtc      780
accgtctcct cagtcgacga gtccaaatat ggtcccccat gcccaccatg cccagcacct      840
gagttcctgg gggaccatc agtcttcctg ttccccccaa acccaaggga cactctcatg      900
atctcccgga cccctgaggt cacgtgcgtg gtggtggacg tgagccagga gacccccgag      960
gtccagttca actggtacgt ggatggcgtg gaggtgcata atgccaagac aaagccgcgg     1020
gaggagcagt tcaacagcac gtaccgtgtg gtcagcgtcc tcaccgtcct gcaccaggac     1080
tggctgaacg gcaaggagta caagtgcaag gtctccaaca aaggcctccc gtcctccatc     1140
gagaaaacca tctccaaagc caaagggcag ccccgagagc cacaggtgta caccctgccc     1200
ccatcccagg aggagatgac caagaaccag gtcagcctga cctgcctggt caaaggcttc     1260
taccccagcg acatcgccgt ggagtgggag agcaatgggc agccggagaa caactacaag     1320
accacgcctc ccgtgctgga ctccgacggc tccttcttcc tctacagcag gctaaccgtg     1380
gacaagagca ggtggcagga ggggaatgtc ttctcatgct ccgtgatgca tgaggctctg     1440
cacaaccact acacacagaa gagcctctcc ctgtccctag gtaaaatgtt ttgggtgctg     1500
gtggtggttg gtggagtcct ggcttgctat agcttgctag taacagtggc ctttattatt     1560
ttctgggtga ggagtaagag gagcaggggc ggacacagtg actacatgaa catgactccc     1620
cgccgccctg ggcccacccg caagcattac cagccctatg ccccaccacg cgacttcgca     1680
gcctatcgct ccaaacgggg cagaaagaaa ctcctgtata tattcaaaca accatttatg     1740
agaccagtac aaactactca agaggaagat ggctgtagct gccgatttcc agaagaagaa     1800
gaaggaggat gtgaactgag agtgaagttc agcaggagcg cagacgcccc cgcgtaccag     1860
cagggccaga accagctcta taacgagctc aatctaggac gaagagagga gtacgatgtt     1920
```

```
ttggacaaga gacgtggccg ggaccctgag atggggggaa agccgagaag gaagaaccct    1980
caggaaggcc tgtacaatga actgcagaaa gataagatgg cggaggccta cagtgagatt    2040
gggatgaaag gcgagcgccg gaggggcaag gggcacgatg gcctttacca gggtctcagt    2100
acagccacca aggacaccta cgacgccctt cacatgcagg ccctgccccc tcgctga       2157
```

```
<210> SEQ ID NO 112
<211> LENGTH: 2169
<212> TYPE: DNA
<213> ORGANISM: Artificial Sequence
<220> FEATURE:
<223> OTHER INFORMATION: Synthetic polynucleotide

<400> SEQUENCE: 112
```

```
atgggatggt catgtatcat cctttttcta gtagcaactg caaccggtgt acattccgat      60
attgtgatga ctcaggctgc accctctgta cctgtcactc ctggagagtc agtatccatc     120
tcctgcaggt ctagtaagag tctcctgcat agtaatggca acacttactt gtattggttc     180
ctgcagaggc caggccagtc tcctcagctc ctgatatatc ggatgtccaa ccttgcctca     240
ggagtcccag acaggttcag tggcagtggg tcaggaactg ctttcacact gagaatcagt     300
agagtggagg ctgaggatgt gggtgtttat tactgtatgc aacatctaga atatcctctc     360
acggtcggtg ctgggaccaa gctggagctg aaaggctcca cctctggatc cggcaagccc     420
ggatctggcg agggatccac caagggccag gttcaactgc aacagtctgg ggctgagctg     480
gtgaggcctg gggcttcagt gaagctgtcc tgcaaggctt ggggctacac atttactgac     540
tatgaaatgc actgggtgaa gcagacacct gtgcatggcc tggaatggat tggagctatt     600
catccaggaa gtggtggtac tgcctataat cagaagttca agggcaaggc cacactgact     660
gcagacaaat cctccagcac agcctacatg gagctcagca ggctgacatc tgaggactct     720
gctgtctatt actgtacaag aaggaggcct aggttctatg gtatggacta ctggggtcaa     780
ggaacctcag tcaccgtctc ctcagtcgac gagtccaaat atggtccccc atgcccacca     840
tgcccagcac ctgagttcct ggggggacca tcagtcttcc tgttcccccc aaaacccaag     900
gacactctca tgatctcccg gacccctgag gtcacgtgcg tggtggtgga cgtgagccag     960
gaagaccccg aggtccagtt caactggtac gtggatggcg tggaggtgca taatgccaag    1020
acaaagccgc gggaggagca gttcaacagc acgtaccgtg tggtcagcgt cctcaccgtc    1080
ctgcaccagg actggctgaa cggcaaggag tacaagtgca aggtctccaa caaaggcctc    1140
ccgtcctcca tcgagaaaac catctccaaa gccaaagggc agccccgaga gccacaggtg    1200
tacaccctgc ccccatccca ggaggagatg accaagaacc aggtcagcct gacctgcctg    1260
gtcaaaggct tctaccccag cgacatcgcc gtggagtggg agagcaatgg gcagccggag    1320
aacaactaca agaccacgcc tcccgtgctg gactccgacg gctccttctt cctctacagc    1380
aggctaaccg tggacaagag caggtggcag gaggggaatg tcttctcatg ctccgtgatg    1440
catgaggctc tgcacaacca ctacacacag aagagcctct ccctgtccct aggtaaaatg    1500
ttttgggtgc tggtggtggt tggtggagtc ctggcttgct atagcttgct agtaacagtg    1560
gcctttatta ttttctgggt gaggagtaag aggagcaggg gcggacacag tgactacatg    1620
aacatgactc cccgccgccc tgggcccacc cgcaagcatt accagcccta tgccccacca    1680
cgcgacttcg cagcctatcg ctccaaacgg ggcagaaaga aactcctgta tatattcaaa    1740
caaccatttt tgagaccagt acaaactact caagaggaag atggctgtag ctgccgattt    1800
ccagaagaag aagaaggagg atgtgaactg agagtgaagt tcagcaggag cgcagacgcc    1860
```

-continued

```
cccgcgtacc agcagggcca gaaccagctc tataacgagc tcaatctagg acgaagagag    1920
gagtacgatg ttttggacaa gagacgtggc cgggaccctg agatggggggg aaagccgaga    1980 aggaagaacc ctcaggaagg cctgtacaat gaactgcaga aagataagat ggcggaggcc    2040
tacagtgaga ttgggatgaa aggcgagcgc cggaggggca aggggcacga tggcctttac    2100
cagggtctca gtacagccac caaggacacc tacgacgccc ttcacatgca ggccctgccc    2160
cctcgctga                                                            2169
```

<210> SEQ ID NO 113
<211> LENGTH: 82
<212> TYPE: PRT
<213> ORGANISM: Homo sapiens

<400> SEQUENCE: 113

```
His Gln Cys Tyr Asn Gly Ser Gly Met Asp Tyr Arg Gly Thr Ala Ser
1               5                   10                  15

Thr Thr Lys Ser Gly His Gln Cys Gln Pro Trp Ala Leu Gln His Pro
            20                  25                  30

His Ser His His Leu Ser Ser Thr Asp Phe Pro Glu Leu Gly Gly Gly
        35                  40                  45

His Ala Tyr Cys Arg Asn Pro Gly Gly Gln Met Glu Gly Pro Trp Cys
    50                  55                  60

Phe Thr Gln Asn Lys Asn Val Arg Met Glu Leu Cys Asp Val Pro Ser
65                  70                  75                  80

Cys Ser
```

<210> SEQ ID NO 114
<211> LENGTH: 69
<212> TYPE: PRT
<213> ORGANISM: Homo sapiens

<400> SEQUENCE: 114

```
Ala Ile Leu His Cys Lys Val Ala Gly Asn Pro Pro Pro Asn Val Arg
1               5                   10                  15

Trp Leu Lys Asn Asp Ala Pro Val Val Gln Glu Pro Arg Arg Ile Ile
            20                  25                  30

Ile Arg Lys Thr Glu Tyr Gly Ser Arg Leu Arg Ile Gln Asp Leu Asp
        35                  40                  45

Thr Thr Asp Thr Gly Tyr Tyr Gln Cys Val Ala Thr Asn Gly Met Lys
    50                  55                  60

Thr Ile Thr Ala Thr
65
```

<210> SEQ ID NO 115
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 115

```
Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45
```

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg

<210> SEQ ID NO 116
<211> LENGTH: 95
<212> TYPE: PRT
<213> ORGANISM: Artificial Sequence
<220> FEATURE:
<223> OTHER INFORMATION: Synthetic polypeptide

<400> SEQUENCE: 116

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro
                85                  90                  95

<210> SEQ ID NO 117
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 117

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg

<210> SEQ ID NO 118
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 118

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro
            100

<210> SEQ ID NO 119
<211> LENGTH: 95
<212> TYPE: PRT
<213> ORGANISM: Artificial Sequence
<220> FEATURE:
<223> OTHER INFORMATION: Synthetic polypeptide

<400> SEQUENCE: 119

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Asn Ser Trp Pro
                85                  90                  95

<210> SEQ ID NO 120
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 120

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
        50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Ser
```

-continued

```
        100

<210> SEQ ID NO 121
<211> LENGTH: 95
<212> TYPE: PRT
<213> ORGANISM: Artificial Sequence
<220> FEATURE:
<223> OTHER INFORMATION: Synthetic polypeptide

<400> SEQUENCE: 121

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro
                85                  90                  95

<210> SEQ ID NO 122
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 122

Met Arg Ile Gly Ile Pro Ala Glu Arg Leu Gly Arg Tyr His Gln Cys
1               5                   10                  15

Tyr Asn Gly Ser Gly Met Asp Tyr Arg Gly Thr Ala Ser Thr Thr Lys
            20                  25                  30

Ser Gly His Gln Cys Gln Pro Trp Ala Leu Gln His Pro His Ser His
        35                  40                  45

His Leu Ser Ser Thr Asp Phe Pro Glu Leu Gly Gly Gly His Ala Tyr
    50                  55                  60

Cys Arg Asn Pro Gly Gly Gln Met Glu Gly Pro Trp Cys Phe Thr Gln
65                  70                  75                  80

Asn Lys Asn Val Arg Met Glu Leu Cys Asp Val Pro Ser Cys Ser Pro
                85                  90                  95

Arg Asp Ser Ser Lys Met Gly
                100
```